United States Patent
Bogoev et al.

(10) Patent No.: US 9,733,212 B2
(45) Date of Patent: Aug. 15, 2017

(54) SHARPLY RESOLVING LABELED PROTEIN MOLECULAR WEIGHT STANDARDS

(71) Applicant: LIFE TECHNOLOGIES CORPORATION, Carlsbad, CA (US)

(72) Inventors: Roumen Bogoev, San Marcos, CA (US); Douglas Kang, Rancho Santa Margarita, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 13/715,812

(22) Filed: Dec. 14, 2012

(65) Prior Publication Data

US 2013/0207044 A1    Aug. 15, 2013

Related U.S. Application Data

(63) Continuation of application No. 12/263,672, filed on Nov. 3, 2008, now abandoned, which is a continuation of application No. 11/781,251, filed on Jul. 21, 2007, now abandoned.

(60) Provisional application No. 60/820,101, filed on Jul. 21, 2006, provisional application No. 60/870,252, filed on Dec. 15, 2006.

(51) Int. Cl.
| | | |
|---|---|---|
| *G01N 27/416* | (2006.01) | |
| *C07K 1/13* | (2006.01) | |
| *C07K 1/26* | (2006.01) | |

(52) U.S. Cl.
CPC .......... *G01N 27/4163* (2013.01); *C07K 1/13* (2013.01); *C07K 1/26* (2013.01); *Y10T 436/105831* (2015.01)

(58) Field of Classification Search
None
See application file for complete search history.

(56) References Cited

U.S. PATENT DOCUMENTS

| | | |
|---|---|---|
| 3,485,736 A | 12/1969 | Vesterberg et al. |
| 3,980,540 A | 9/1976 | Hoefer |
| 4,142,960 A | 3/1979 | Hahn et al. |
| 4,337,131 A | 6/1982 | Vesterberg |
| 4,339,327 A | 7/1982 | Tyler |
| 4,405,720 A | 9/1983 | Merril |
| 4,468,466 A | 8/1984 | Morrissey |
| 4,507,233 A | 3/1985 | Saito |
| 4,560,459 A | 12/1985 | Hoefer |
| 4,574,040 A | 3/1986 | Delony et al. |
| 4,575,452 A | 3/1986 | Lee et al. |
| 4,677,196 A | 6/1987 | Rausch et al. |
| 4,766,224 A | 8/1988 | Rausch |
| 4,782,027 A | 11/1988 | Lee |
| 4,920,059 A | 4/1990 | Moeremans et al. |
| 5,030,566 A | 7/1991 | Son et al. |
| 5,132,439 A | 7/1992 | Schultz |
| 5,173,906 A | 12/1992 | Dreibelbis et al. |
| 5,227,086 A | 7/1993 | Kacher et al. |
| 5,264,144 A | 11/1993 | Moroney et al. |
| 5,264,145 A | 11/1993 | French et al. |
| 5,268,080 A | 12/1993 | Kambara et al. |
| 5,270,181 A | 12/1993 | McCoy et al. |
| 5,273,906 A | 12/1993 | Shultz et al. |
| 5,279,792 A | 1/1994 | Moeremans et al. |
| 5,292,646 A | 3/1994 | McCoy et al. |
| 5,330,902 A | 7/1994 | Keck et al. |
| 5,340,492 A | 8/1994 | Kacher et al. |
| 5,425,892 A | 6/1995 | Taneri et al. |
| 5,449,758 A | 9/1995 | Hartley |
| 5,510,049 A | 4/1996 | Connor et al. |
| 5,582,702 A | 12/1996 | Cabilly et al. |
| 5,605,691 A | 2/1997 | Carroll |
| 5,616,502 A | 4/1997 | Haugland et al. |
| 5,705,649 A | 1/1998 | Shultz et al. |
| 5,785,832 A | 7/1998 | Chiari et al. |
| 5,834,286 A | 11/1998 | Nevalainen et al. |
| 5,865,974 A | 2/1999 | Cabilly et al. |
| 5,922,185 A | 7/1999 | Updyke et al. |
| 6,057,106 A | 5/2000 | Updyke |
| 6,059,948 A | 5/2000 | Updyke et al. |
| 6,096,182 A | 8/2000 | Updyke et al. |
| 6,113,766 A | 9/2000 | Steiner et al. |
| 6,143,154 A | 11/2000 | Updyke et al. |
| 6,156,182 A | 12/2000 | Olech et al. |
| 6,162,338 A | 12/2000 | Updyke et al. |
| 6,379,516 B1 | 4/2002 | Cabilly et al. |
| 6,495,017 B1 | 12/2002 | Islam et al. |

(Continued)

FOREIGN PATENT DOCUMENTS

| | | |
|---|---|---|
| EP | 0550771 | 7/1993 |
| EP | 0744614 | 11/1996 |

(Continued)

OTHER PUBLICATIONS

US 7,232,883, 06/2007, Chatterjee et al. (withdrawn)
US 7,232,884, 06/2007, Chatterjee et al. (withdrawn)
Setlow P. Purification and properties of some unique low molecular weight basic proteins degraded during germination of Bacillus megaterium spores. 1975. Journal of Biological Chemistry. 250:8168-8173.*
Yang C et al. Mechanisms of WNK1 and WNK4 interaction in the regulation of thiazide-sensitive NaCl cotransport. 2005. The Journal of Clinical Investigation. 115:1379-1387.*
Sigma Deutschland, Deisenhofen ""Biochemikalien Organische Verbindungen und Diagnostike Produktkatalog"", , XP002268149, 1996, 1898-1902.
Molecular Probes Product Information, ""Conjugation with Amine-Reactive Probes, 1996, 1-8.

(Continued)

*Primary Examiner* — Paul Holland

(57) ABSTRACT

Pre-labeled protein standards useful in electrophoresis that have sharp, consistent separation characteristics that are substantially the same as those of their unlabeled counterparts are provided. The invention provides pre-labeled protein standard sets that include a plurality of labeled proteins that are labeled on a first amino acid, in which side reactions of the label with amino acids not targeted for labeling are reduced.

4 Claims, 27 Drawing Sheets

(56) References Cited

U.S. PATENT DOCUMENTS

| | | | |
|---|---|---|---|
| 6,562,213 B1 | 5/2003 | Margalit et al. | |
| 6,599,410 B1 | 7/2003 | Steiner et al. | |
| 6,645,725 B2 | 11/2003 | Yeaman | |
| 6,703,484 B2 | 3/2004 | Chatterjee et al. | |
| 6,936,150 B2 | 8/2005 | Rooney et al. | |
| 7,132,520 B2 | 11/2006 | Hartley | |
| 7,223,566 B2 | 5/2007 | Chatterjee et al. | |
| 7,259,242 B2 | 8/2007 | Chatterjee et al. | |
| 7,265,206 B2 | 9/2007 | Chatterjee et al. | |
| 7,781,173 B2 | 8/2010 | Amshey et al. | |
| 2002/0115103 A1 | 8/2002 | Gad et al. | |
| 2002/0127330 A1 | 9/2002 | Jin et al. | |
| 2002/0134680 A1 | 9/2002 | Cabilly | |
| 2003/0015426 A1 | 1/2003 | Rooney et al. | |
| 2003/0093832 A1 | 5/2003 | Szarka et al. | |
| 2003/0121784 A1 | 7/2003 | Updyke et al. | |
| 2003/0127330 A1 | 7/2003 | Updyke et al. | |
| 2003/0138425 A1 | 7/2003 | Mather | |
| 2003/0232014 A1 | 12/2003 | Burke et al. | |
| 2004/0014082 A1* | 1/2004 | Tadayoni-Rebek et al. | 435/6 |
| 2004/0110186 A1 | 6/2004 | Aebersold et al. | |
| 2005/0239135 A1 | 10/2005 | Bogoev et al. | |
| 2006/0269992 A1 | 11/2006 | Chatterjee et al. | |
| 2006/0286633 A1 | 12/2006 | Chatterjee et al. | |
| 2007/0184527 A1 | 8/2007 | Chatterjee et al. | |
| 2007/0190606 A1 | 8/2007 | Chatterjee et al. | |
| 2009/0087873 A1 | 4/2009 | Bogoev et al. | |
| 2009/0178926 A1 | 7/2009 | Bogoev et al. | |
| 2011/0098447 A1 | 4/2011 | Amshey et al. | |
| 2011/0108420 A1 | 5/2011 | Chatterjee et al. | |
| 2012/0184712 A1 | 7/2012 | Amshey et al. | |

FOREIGN PATENT DOCUMENTS

| | | |
|---|---|---|
| EP | 98903438 | 7/1998 |
| JP | 03015752 | 1/1991 |
| JP | 08-509504 | 10/1996 |
| WO | WO-84/03103 | 8/1984 |
| WO | WO-88/07086 | 9/1988 |
| WO | WO-92/01707 | 2/1992 |
| WO | WO-92/13955 | 8/1992 |
| WO | WO-94/02502 | 2/1994 |
| WO | WO-95/19993 | 7/1995 |
| WO | WO-95/27197 | 10/1995 |
| WO | WO-96/08570 | 3/1996 |
| WO | WO-96/17942 | 6/1996 |
| WO | WO-96/30514 | 10/1996 |
| WO | WO-96/34276 | 10/1996 |
| WO | WO-97/28248 | 8/1997 |
| WO | WO-97/41070 | 11/1997 |
| WO | WO-98/57161 | 12/1998 |
| WO | WO-99/03872 | 1/1999 |
| WO | WO-99/37813 | 7/1999 |
| WO | WO-2005/030981 | 4/2005 |
| WO | WO-2006/138366 | 12/2006 |
| WO | WO-2008042495 | 4/2008 |

OTHER PUBLICATIONS

Allen, Robert C. et al., "Component Visualization", *Gel Electrophoresis of Proteins and Nucleic Acids: Selected Techniques,*, Walter De Gruyter, Berlin, New York,; XP002268148, ISBN: 3110138964, 1994, pp. 204-272.

Asermely, Karen E. et al., "Identification of a recombinant synaptobrevin-thioredoxin fusion protein by capillary zone electrophoresis using laser-induced fluorescence detection", *Journal of Chromatography B*, vol. 695, 1997, 67-75.

Ausubel, F. M. , "Protein Expression", *Current Protocols in Molecular Biology*, vol. 2,, 1994, pp. 16.4.1-16.8.14.

Ausubel, Frederick M. et al., "Current Protocols in Molecular Biology", John Wiley & Sons, Inc., Boston, MA, 1994-1998, 4.6.1-4.6.13.

Bachmair, Andreas et al., "In vivo half-life of a protein is a function of its amino-terminal residue", *Science*, vol. 234, Oct. 10, 1986, 179-189.

Barger, Bruce O. et al., "Estimation of Molecular Weight by Polyacrylamide Gel Electrophoresis Using Heat Stable Fluorophors", *Analytical Biochemistry*, vol. 70, 1976, 327-335.

Bates, Robert C. et al., "Autonomous Parvovirus LuIII encapsidates Equal Amounts of Plus and Minus DNA Strands.", *Journal of Virology*, vol. 49, No. 2, Feb. 1984, 319-324.

Berkelman, Tom et al., *2-D Electrophoresis using immobilized pH gradients—Principles and Methods*, Amersham Biosciences, Edition Ac; Freiburg, Germany, 1998, 7-100.

Betton, J.-M , "Rapid Translation Sysytem (RTS): a Promising Alternative for Recombinant Protein Production", *Current Protein and Peptide Science*, vol. 4, No. 1, 73-80, Feb. 2003.

Betton, Jean-Michel et al., "Folding of a mutant maltose binding protein of *E. coli* which forms inclusion bodies.", *The Journal of Biological Chemistry*, vol. 271, No. 14, Apr. 5, 1996, 8046-8052.

BIO-RAD Laboratories, , "Electrophoresis and Blotting Standards, Protein Standards", *BIORAD Catalog,*, 1993, p. 316.

BIO-RAD Laboratories, , "Introducing Kaleidoscope Prestained Standards", *BIO-RADiations,*, No. 87,, 1993, pp. 1-4.

BIO-RAD Laboratories, , "Recombinant Prestained and Unstained Standards", *Electrophoresis and Blotting: Standards and Reagents, Protein Standards,*, 2002, pp. 200-204.

Bosshard, Heinrich F. et al., "The Use of a New Reactive Dye for Quantitation of Prestained Proteins on Polyacrylamide Gels", *Analytical Biochemistry*, vol. 82, 1977, 327-333.

Bottari, et al., "Design and Synthesis of Visible Isotope-Coded Affinity Tags for the Absolute Quantification of Specific Proteins in Complex Mixtures", *Bioconjugate Chemistry,*, vol. 15, No. 2,, Sep. 22, 2003, 380-388.

Botti, Paolo et al., "Native chemical ligation using removable Nalpha-(1-phenyl-2-mercaptoethyl) auxiliaries", *Tetrahedron Letters*, vol. 42, 2001, 1831-1833.

Buchner, Johannes et al., "Renaturation Purification and Characterization of Recombinant F Fragments Produced in *Escherichia coli*", *Bio/Technology*, vol. 9, Feb. 1991, 157-162.

Carter, Paul , "Site-Specific Proteolysis of Fusion Proteins", *Protein Purification: From Molecular Mechanisms to Large-Scale Processes*, American Chemical Society Symposium Series, vol. 427, 1990, 181-193.

Champliaud, et al., "Posttranslational Modifications and / Chain Associations of Human Laminin 1 and Laminin 5 Chains: Purification of Laminin-3 from Placenta", *Experimental Cell Research*, vol. 259, Issue 2, Sep. 15, 2000, 326-335.

Chatterjee, Deb K. et al., "Cloning and overexpression of the gene encoding bacteriophage T5 DNA polymerase", *Gene*, vol. 97, 1991, 13-19.

Chatterjee, Deb K. et al., "Genetic Organization of the Kpr1 Restriction-Modification System", *Nucleic Acids Research*, vol. 19, No. 23, 1991, 6505-6509.

Coburn, Glen A. et al., "Overexpression, Purification, and Properties of *Escherichia coli* Ribonuclease II", *The Journal of Biological Chemistry*, vol. 271, No. 2, Jan. 12, 1996, 1048-1053.

Compton, Mark M. , "Generation of multicolored,prestained molecular weight markers for gel electrophoresis", *Electrophoresis*, vol. 23, 2002, 3262-3265.

Crawford, N. A. et al., "Evidence for Function of the Ferredoxin/Thioredoxin System in the Reductive Activation of Target Enzymes of Isolated Intact Chloroplasts", *Archives of Biochemistry and Biophysics*, vol. 271, No. 1, May 15, 1989, 223-39.

Dahlberg, Albert E. et al., "Electrophoretic Characterization of Bacterial Polyribosomes in Agarose-Acrylamide Composite Gels.", *J. Mol. Biol.*, vol. 41, 1969, 139-147.

Dalmia, Bipin K. et al., "Domain E. of Bacillus Macerans Cyclodextrin Glucanotransferase: An Independent Starch-Binding Domain", *Biotechnology and Bioengineering*, vol. 47, 1995, 575-584.

Datyner, Arved et al., "A Prestaining Method for the Quantitative Assay of Proteins on Polyacrylamide gels", *Analytical Biochemistry*, vol. 55, No. 2, 1973, 479-491.

(56) References Cited

OTHER PUBLICATIONS

Dekker, Niek et al., "In vitro folding of *Escherichia coli* outermembrane phospholipase A", *Eur. J. Biochem.*, vol. 232, 1995, 214-219.
Derman, Alan I. et al., "*Escherichia coli* Alkaline Phosphatase Localized to the Cytoplasm Slowly Acquires Enzymatic Activity in Cells Whose Growth Has Been Suspended: a Caution for Gene Fusion Studies", *Journal of Bacteriology*, vol. 177, No. 13, Jul. 1995, 3764-3770.
Dolnik, Vladislav, "Capillary zone electrophoresis of proteins", *Electrophoresis*, vol. 18, 1997, 2353-2361.
Edwards, Robert A. et al., "Cloning and Expression of a Murine Fascin Homolog from Mouse Brain", *Journal of Biological Chemistry*, vol. 270, No. 18, May 5, 1995, 10764-10770.
EP04785057.3 Supplementary European Search Report.
EP 07150494 European Search Report mailed Mar. 13, 2008.
EP07863380.7 European Search Report mailed on Sep. 24, 2009.
EP09180307.2 Extended European Search Report mailed May 7, 2010.
EP 98903438 Communication of a Notice of Opposition mailed Mar. 9, 2009.
EP 98903438 Supplementary European Search Report mailed Aug. 10, 2004.
EP 98903438 Supplementary Partial European Search Report mailed May 9, 2003.
EP10174765.7 Extended European Search Report Mailed Mar. 28, 2011.
Fehring, et al., "Physical markers for landmarkingk fluorescently stained gels that facilate automated spot-picking", *Electrophoresis*, vol. 22,, 2001, 2903-2907.
Fisher, M. P. et al., "Role of Molecular Conformation in Determining the Electrophoretic Properties of Polynucleotides in Agarose-Acrylamide Composite Gels.", *Biochemistry*, vol. 10, No. 10, 1971, 1895-1899.
Flynn, Elizabeth et al., "Protein Analysis with the BenchMark Protein Ladders", *Focus*, vol. 19, No. 2, 1997, 33-35.
Georgiou, George et al., "Localization of inclusion bodies in *Escherichia coli* overproducing beta-lactamase or alkaline phosphatase", *Applied and Environmental Microbiology*, vol. 52, No. 5, American Society of Microbiology, Nov. 1986, 1157-1161.
Griffith, I. P., "Immediate Visualization of Proteins in Dodecyl Sulfate-Polyacrylamide Gels by Prestaining with Remazol Dyes", *Analytical Biochemistry*, vol. 46; XP9014182,ISSN: 0003-2697; * p. 404, paragraph 3-p. 410, paragraph 1; figure 1, 1972, 402-412.
Guttman, A. et al., "Analytical and Micropreparative Ultrahigh Resolution of Oligonucleotides by Polyacrylamide Gel High-Performance Capillary Electrophoresis", *Anal. Chem.*, vol. 62, 1990, 137-141.
Haugland, Richard P. ""Handbook of Fluorescent Probes and Research Chemicals; Section 1.5 Dyes With Absorbtion Maxima between 500", and 540 nm" [Onl ine] Dec. 22, 1996 (Dec. 22, 1996), Molecular Probes, XP002268151 (Retrieved from the Internet: URL:http://web.archive.org/web/19970607210142/www. probes.com/acrobat/chOI-5.pdf [retrieved on Nov. 5, 2003] * *p. 25-29, 6th Edition, 1996).
Haugland, Richard P., ""Handbook of Fluorescent Probes and Research Chemicals; Section 1.6 Long-Wavelength Dyes" [Online]", Dec. 22, 1996 (Dec. 22, 1996), Molecular Probes, XP002268150 Retrieved from the Internet: URL:http://web.archive. org/web/19970607210142/www.probes.com/acrobat/chOI-5.pdf [retrieved on Nov. 5, 2003] * *p. 29-p. 35, Retrieved from the Internet: URL:http://web.archive.org/web/eb/19970607210142/ www.probes.com/acrobat/chOI-5.pdf *p. 32, left-hand column, paragraph 3 *, Dec. 22, 1996, 29-35.
Haugland, Richard P., "Handbook of Fluorescent Probes and Research Products", Ch 1-3.3, Molecular Probes, Inc/Invitrogen, 2002, 2002, 11-118.
Hermanson, Greg T., *Bioconjugate Techniques (Textbook)*, Pierce Chemical Company, Academic Press, 1996.

Hitomi, Y. et al., "High Efficiency Prokaryotic Expression and Purification of a Portion of the Hepatitis C Core Protein and Analysis of the Immune Response to Recombinant Protein in BALB/c Mice", *Viral Immunology*, vol. 8, No. 2, 1995, 109-119.
Hjerten, Stellan, "High-Performance Electrophoresis: the Electrophoretic Counterpart of High-Performance Liquid Chromatography", *Journal of Chromatography*, vol. 270, 1983, 1-6.
Hochuli, Erich, "Interaction of Hexahistidine Fusion Proteins with Nitrilotriacetic Acid-Chelated Ni2+ Ions", *Methods: A Companion to Methods in Enzymology*, vol. 4, 1992, 68-72.
Hoog, Jan-Olov et al., "Nucleotide sequence of the thioredoxin gene from *Escherichia coli*", *Bioscience Reports*, vol. 4, 1984, 917-923.
Horowitz, Paul M. et al., "Electrophoresis of Proteins and Nucleic Acids on Acrylamide Agarose Gels Lacking Covalent Cross-Linkings.", *Analytical Biochemistry*, vol. 143, 1984, 333-340.
Invitrogen, "Featuring the Gold Standards in Band Identification", *Protein Standards Brochure*, 2002, 12 pp.
Isono, Katsumi et al., "Lack of Ribosomal Protein S1 in Bacillus Sterothermophilus.", *Proceedings of the National Academy of Sciences (PNAS)*, vol. 73, No. 8, Mar. 1976, 767-770.
Kane, James F. et al., "Effects of rare codon clusters on high-level expression of heterologous proteins in *Escherichia coli*", *Current Opinion in Biotechnology*, vol. 6, 1995, pp. 494-500.
Kim, Sun-Ok et al., "High-Level Expression and Simple Purification of Recombinant Human Insulin-like Growth Factor 1", *Journal of Biotechnology*, vol. 48,, 1996, 97-105.
Krishna, R. G., *Techniques in Protein Chemistry 111*, Academic Press, San Diego, 1992, p. 77-84.
Kuhelj, Robert et al., "The preparation of catalytically active human cathepsin B from its precursor expressed in *Escherichia coli* in the form of inclusion bodies", *Eur. J. Biochem.*, vol. 229, 1995, 533-539.
Kurian, Ponnamma et al., "The use of Bacteriophage T-4 as a set of molecular weight and ISO electric point markers for 2 Dimensional Electrophoresis", *Electrophoresis*, vol. 2, No. 3, 1981, 184-187.
Laemmli, et al., "Cleavage of Structural Proteins during the Assembly of the Head of Bacteriophage T4", *Nature*, vol. 227, Issue 5259,, Aug. 15, 1970, 680-685.
Langsetmo, et al., "*Escherichia coli* thioredoxin folds into two compact forms of different stability to urea denaturation", *Biochemistry*, vol. 28, No. 8,pp. 3211-3220., 1989, 3211-3220.
Lavallie, Edward R. et al., "A Thioredoxin Gene Fusion Expression System That Circumvents Inclusion body Formation in the *E. coli* Cytoplasm", *Bio/Technology*, vol. 11, Feb. 1993, 187-193.
Lavallie, Edward R. et al., "Gene fusion expression systems in *Escherchia coli*", *Current Opinion in Biotechnology*, vol. 6,, 1995, 501-506.
Lindbladh, C. et al., "Standard Calibration Proteins for Western Blotting Obtained by Genetically Prepared Protein a Conjugates", *Analytical Biochemistry*, vol. 197, Issue 1, 1991, 187-190.
Lopez, Mary F., "Advantages of carrier Ampholyte IEF", *Methods Molecular Biology*, vol. 112, 2-D Proteome Analysis Protocols, 1999, 109-110.
Lunn, Charles A. et al., "Amplification and Purification of Plasmid-encoded Thioredoxin from *Escherichia coli* K12", *The Journal of Biological Chemistry*, vol. 259, No. 16, Aug. 25, 1984, 10469-10474.
Magin, Thomas M. et al., "Analysis of cytokeratin domains by Cloning and Expression of Intact and Deleted Polypeptides in *Escherichia coli*", *The EMBO Journal*, vol. 6, No. 9, 1987, 2607-2615.
Matsui, Neil M. et al., "Ch 23: Running preparative carrier ampholyte and immobilized pH gradient IEF gels for 2-D", *2-D Proteome Analysis Protocols*, vol. 112, Methods in Molecular Biology, 1999, 211-219.
McCoy, John, "*E. coli* Lysis Using a French Pressure Cell", *Current Protocols in Molecular Biology*, New York: John Wiley & Sons, Ausubel editor, 1995, 16.8.6-16.8.14.
Minter, et al., "Nucleic Acid and Polypeptide molecular weight markers", *Transcription and Translation: a practical approach*, Appendix, edited by BD Hames & SJ Higgins; XP001538042,, Jan. 1, 1984, 303-316.

(56) References Cited

OTHER PUBLICATIONS

Mitraki, et al., "Protein Folding Intermediates and Inclusion Body Formation", *BioTechnology*, vol. 7,, Jul. 1989, 690-697.

Molecular Probes, 1996, , "Amine-Reactive Probes", *Product Information Sheet*, MP0143, 1996.

Neophytou, Pavlos I. et al., "Development of a Procedure for the Direct Cloning of T-Cell Epitopes Using Bacterial Expression Systems", *Journal of Immunological Methods*, vol. 196, Issue 1, 1996, 63-72.

Oberfelder, R. W. et al., "Protein Expression by Inclusion", *The FASEB Journal*, vol. 11, No. 9, Abstract # 2007, Federation of American Societies for Experimental Biology, Jul. 31, 1997, A1200.

O'Farrell, Patrick H. et al., "High Resolution Two-Dimensional Electrophoresis of Proteins", *Journal of Biological Chemistry*, vol. 250, No. 10, May 25, 1975, 4007-4021.

PCT/US04/31535, , "International Search Report mailed Sep. 26, 2008".

PCT/US07/74058, , "International Preliminary Report on Patentability, Date of issuance Jan. 27, 2009".

PCT/US07/74058, , "International Search Report mailed May 9, 2008".

PCT/US07/74058, , "Written Opinion mailed May 9, 2008".

PCT/US98/00492, , "International Search Report mailed May 12, 1998".

Peacock, et al., "Molecular Weight Estimation and Separation of Ribonucleic Acid by Electrophoresis in Agarose-Acrylamide Composite Gels.", *Biochemistry*, vol. 7, Issue 2,, Feb. 1968, 668-674.

Poole, Catherine B. et al., "Cloning of a Caticular Antigen that contains multiple Tandem Repeats from the filarial Parasite Dirofilaria Immits", *Proceedings of the National Academy of Sciences (PNAS)*, vol. 89, Jul. 1992, 5986-90.

Ramus, et al., "An optimized strategy for ICAT quantification of membrane proteins", *MCP Papers in Press, The American Society for Biochemistry and Molecular Biology, Inc.*, Manuscript M500205-MCP200, Oct. 10, 2005, 1-36.

Rando, Robert R. , "Chemical biology of protein isoprenylation/methylation", *Biochimica et Biophysica Acta*, vol. 1300, 1996, 5-16.

Rashid, Mohammad A. et al., "Electrophoretic Extraction-Concentration of Ribonucleic Acid from Agarose-Acrylamide Composite Gels.", *Analytical Biochemistry*, vol. 127, 1982, 334-339.

Reddy, Prasad et al., "Hyperexpression and purification of *Escherichia coli* adenylate cyclase using a vector designed for expression of lethal gene products.", *Nucleic Acids Research*, vol. 17, No. 24, 1989, 10473-10488.

Reischl, Udo et al., "Preparative SDS-Page Electrophoresis of a Recombinant Epstein-Barr Virus Encoded Protein and Its Application in Serodiagnostic Test Systems", *Bio-Rad Laboratories, Inc., Bulletin 2024*, 2002, 1-4.

Righetti, Pier G. et al., "Immobilized Buffers for Isoelectric Focusing: From Gradient Gels to Membranes", *Electrophoresis*, vol. 15, 1994, 1040-1043.

Righetti, Pier G. et al., "Isoelectric Focusing in Gels", *Journal of Chromatography*, vol. 98, No. 2, Sep. 25, 1974, 271-321.

Righetti, Pier G. et al., "Isoelectric Focusing in Immobilized pH Gradients", *Methods in Enzymology*, vol. 270, 1996, 235-255.

Rinas, Ursula et al., "Overexpression of Bacterial Hemoglobin Causes Incorporation of Pre-B-Lactamase into Cytoplasmic Inclusion Bodies", *Applied and Environmental Microbiology*, vol. 59, No. 2, Feb. 1993, 561-566.

Ringborg, U et al., "Agarose-Acrylamide Composite Gels for Microfractionation of RNA", *Nature*, vol. 220, Dec. 7, 1968, 1037-1039.

Sambrook, J et al., "Expression of Cloned Genes in *Escherichia coli*", *Molecular Cloning: A Laboratory Manual*, 2nd Ed. Cold Spring Harbor Laboratory Press, Cold Spring Harbor, NY, 1989, 17.2-17.9.

Sambrook, J. et al., "Preparation of Protoplasts", *Molecular Cloning: A Laboratory Manual*, 2nd Ed., Sambrook, J. , et al. , eds. Cold Spring Harbor Laboratory Press, Cold Spring Harbor, NY, 1989, 16.49.

Saoji, et al., "Remazol Brilliant Blue as a Pre-Stain for the Immediate Visualization of Human Serum Proteins on Polyacrylamide Gel Disc Electrophoresis", *Clinical Chemistry, American Association for Clinical Chemistry*, Washington, DC,, vol. 29, No. 1,; XP009014263; ISSN: 0009-9147; * tables 1-3 *, Jan. 1, 1983, 42-44.

Sato, et al., "Site-Specific Modification of Interleukin-2 by the Combined Use of Genetic Engineering Techniques and Transglutaminase", *Biochemistry*, vol. 35, No. 40,, Oct. 8, 1996, 13072-13080.

Schagger, Hermann et al., "Analysis of Molecular masses and Oligomeric States of Protein Complexes by Blue Native Electrophoresis and Isolation of Membrane Protein Complexes by Two-Dimensional Native Electrophoresis.", *Analytical Biochemistry*, vol. 217, 1994, 220-230.

Schagger, Hermann , "Blue-Native Gels to Isolate Protein Complexes from Mitochondria", *Methods Cell Biol.*, vol. 65, 2001, 232-244.

Schein, Catherine H. , "Review: Production of Soluble Recombinant Proteins in Bacteria", *Bio/Technology*, vol. 7, Nov. 1989, 1141-1149.

Schneider, Erwin et al., "Functional Purification of a Bacterial ATP-Binding Cassette Transporter Protein (MalK) from the Cytoplasmic Fraction of an Overproducing Strain", *Protein Expression and Purification*, vol. 6, 1995, 10-14.

Schomburg, D et al., "EC 3.5.1.1-36 and 38-52, EC 3.5.2.1-7 and 9-12", *Enzyme Handbook 4*, (Springer Berlin), 1991, EC 3.5.1.1-36 and 38-52, EC 3.5.2.1-7 and 9-12.

Setlow, "Purification and Properties of Some Unique Low Molecular Weight Basic Proteins Degraded during Germination of Bacillus megaterium Spores", *The Journal of Biological Chemistry*, vol. 250, No. 20,, Oct. 25, 1975, 8168-8173.

Shimoni, Yuval et al., "Intramolecular Disulfide Bonds between Conserved Cysteines in Wheat Gliadins Control Their Deposition into Protein Bodies", *The Journal of Biological Chemistry*, vol. 271, No. 31, Aug. 2, 1996, 18869-18874.

Sigma, , "Sigma Catalog", Electrophoresis Reagents, 1994, 1751-1755.

Sigma Deustschland, "Electrophoresis Reagents", *Biochemikalien Organische Verbindungen und Diagnostike Produktkatalog*, 1996, 1898-1902.

Strandberg, L. et al., "Factors Influencing Inclusion Body Formation in the Production of a Fused Protein in *Escherichia coli*", *Applied and Environmental Microbiology*, vol. 57, No. 6, Jun. 1991, 1669-1674.

Studier, F. W. et al., "Use of Bacteriophage T7 RNA Polymerase to Direct Selective High-Level Expression of Cloned Genes", *Journal of Molecular Biology*, vol. 189,, 1986, 113-130.

Tokatlidis, Kostas et al., "High Activity of Inclusion Bodies Formed in *Escherichia coli* Overproducing Clostridium Thermocellum Endoglucanase D", *FEBS Lett.*, vol. 282, No. 1, Apr. 1991, 205-208.

Toledo, H et al., "Methylation of proteins from the translational apparatus: an overview", *Arch Biol Med Exp*, vol. 21 (Santiago), 1988, 219-229.

Toone, W. M. et al., "deaD, a new *Escherichia coli* gene encoding a presumed ATP-dependent RNA helicase, can suppress a mutation in rpsB, the gene encoding ribosomal protein S2", *Journal of Bacteriology*, vol. 173, No. 11, Jun. 1991, 3291-3302.

Tsang, Victor C. et al., "Calibration of Prestained Protein Molecular weight standards for use in the western or enzyme-linked immunoelectrotransfer blot techniques", *Analytical Biochemistry*, vol. 143, No. 2'; Academic Press Inc, New York LNK-DOI: 10.1016/0003-2697(84)90667-5; XP24830905,; ISSN: 0003-2697; * p. 304, right-hand column, paragraph 2; table 1*, Jan. 1, 1984, 304-307.

Ugozzoli, M., etal "Separation and Purification of High Molecular Weight Glycoproteins Using Agarose Gel Electrophoresis", *Biotechniques*, vol. 12(2), 1992, 187-190.

Vandenbroeck, Koen et al., "Refolding and single-step purification of procine interferon-gamma from *Escherichia coli* inclusion bodies", *Eur. J. Biochem.*, vol. 215, 1993, 481-486.

Ventura, S. et al., "Protein quality in bacterial inclusion bodies", *TRENDS in Biotechnology*, vol. 24(4), Apr. 2006, 179-185.

(56) References Cited

OTHER PUBLICATIONS

Wei, GE et al., "Formation of Inclusion Bodies May Be the Key Factor for the Stability of Expressed Products in *E. coli*", *Biochemistry and Molecular Biology International*, vol. 37, No. 5, Nov. 1995, 895-901.

Winnacker, Ernst L. et al., "Directed Mutagenesis", *From Genes to Clones: Introduction to Gene Technology*, 1987, 451-481.

Yasufuku, Katsuki et al., "High-Yield Production of Recombinant Endothelin-1", *Journal of Biochemistry*, vol. 112, 1992, 360-365.

Zueco, J. et al., "Protein a fusion proteins as molecular weight markers for use in immunoblotting", *Analytical Biochemistry*, vol. 207, No. 2, 1992, 348-349.

\* cited by examiner

BH SCRAMBLED FRAGS ALIGNMENT WITH Thio-wt                                                                    SECTION 1

```
                        1        10         20         30         40    47
10kd SIZE ADJ_FRAG 1 (1) ATGTGTGATCGTATTATTCACCTGACTGACGACTGCTTTGACACGGA
TrsFusPrl10sequ      (1) ATGAGCGATAAAATTATTCACCTGACTGACGACAGTTTTGACACGGA
CONSENSUS            (1) ATG G GAT  ATTATTCACCTGACTGACGAC G TTTGACACGGA
```

SECTION 2
```
                         48        60         70         80         90    94
10kd SIZE ADJ_FRAG 1 (48) TGTACTCCGCGGACGGGCGCGTCTCGTCGATTTCTGGGCAGAGT
TrsFusPrl10sequ     (48) TGTACTCAAAGCGACGGGGCGATCCTCGTCGATTTCTGGGCAGAGT
CONSENSUS           (48) TGTACTC  GCGGACGGGGCG   CTCGTCGATTTCTGGGCAGAGT
```

SECTION 3
```
                         95      100        110        120        130   141
10kd SIZE ADJ_FRAG 1 (95) GGTGCGGTCCGCGTATGTGTATCGCCCCGATTCTGGATGAACGTGCT
TrsFusPrl10sequ     (95) GGTGCGGTCCGTGCAAAATGATCGCCCCGATTCTGGATGAAATCGCT
CONSENSUS           (95) GGTGCGGTCCG G A    ATCGCCCCGATTCTGGATGAA    GCT
```

SECTION 4
```
                        142       150        160        170        180   188
10kd SIZE ADJ_FRAG 1 (142) GACGAATATCAGGGCCGCCTGACGTTGCACGTCTGAACATCGATCA
TrsFusPrl10sequ     (142) GACGAATATCAGGGCAAACTGACCGTTGCAAAACTGAACATCGATCA
CONSENSUS           (142) GACGAATATCAGGGC   CTGACCGTTGCA  CTGAACATCGATCA
```

SECTION 5
```
                        189       200        210        220        230   235
10kd SIZE ADJ_FRAG 1 (189) AAACCCTGGCACTGCGCCGCCTATGCGGTGGTATCCCGACTC
TrsFusPrl10sequ     (189) AAACCCTGGCACTGCGCGCCGAAATATGGCATCCGTGGTATCCCGACTC
CONSENSUS           (189) AAACCCTGGCACTGCGCGCCG     TATGGCATCCGTGGTATCCCGACTC
```

SECTION 6
```
                        238       250        260        270       279
10kd SIZE ADJ_FRAG 1 (238) TGCTGCTGTTCCGTAACGGTGAA-------------------
TrsFusPrl10sequ     (238) TGCTGCTGTTCAAAAACGGTGAACACCACCACCACCACTAA
CONSENSUS           (238) TGCTGCTGTTC    AACGGTGAA
```

(SEQ ID NO: 9, SEQ ID NO: 10)

FIG. 1A

```
                                       1         10        20        30        40        50        65
                                                                                                    ─── SECTION 1
TRANSLATION OF 10kd       (1)  (1)  MCDRIIHLTDDCFDTDVLRADGARLVDFWAEWCGPRMCIAPILDERADEYQGRLTVARLNIDQNP
SIZE ADJ_FRAG 1

TRANSLATION OF            (1)       MSDKIIHLTDDSFDTDVLKADGAILVDFWAEWCGPCKMIAPILDETADEYQGKLTVAKLNIDQNP
TrsFusPrl10sequ CONSENSUS                 (1)       M DKIIHLTDD FDTDVLKADGA LVDFWAEWCGP   IAPILDE ADEYQGKLTVAKLNIDQNP 66        80          93
                                                            ─── SECTION 2
TRANSLATION OF 10kd      (66) (66)  GTAPRYGIRGIPTLLLFKNGE------
SIZE ADJ_FRAG 1

TRANSLATION OF           (66)       GTAPKYGIRGIPTLLLFKNGEHHHHHH-
TrsFusPrl10sequ

CONSENSUS                (66)       GTAPKYGIRGIPTLLLFKNGE (SEQ ID NO: 12)
```

(SEQ ID NO: 11, SEQ ID NO: 12)

FIG. 1B

SEQUENCE OF THE BH6mer ORF

AGATCTATGTGTGATCGTATTATTCACCTGACTGACGACTGCTTTGACACGGA
TGTACTCCGCGCGGACGGGGCGCGTCTCGTCGATTTCTGGGCAGAGTGGTGC
GGTCCGCGTATGTGTATCGCCCCGATTCTGGATGAACGTGCTGACGAATATCA
GGGCCGCCTGACCGTTGCACGTCTGAACATCGATCAAAACCCTGGCACTAGC
GCTATGTGTGATCGTATTATTCATCTGACTGATGACTGCTTTGACACGGACGT
ACTCCGTGCGGACGGGGCGCGTCTCGTCGATTTCTGGGCAGAGTGGTGCGGT
CCACGTATGTGTATCGCGCCGATTCTGGATGAACGTGCAGACGAATATCAAG
GCCGCCTGACCGTTGCACGCCTGAACATCGATCAAAACCCTGGTACTGCGCC
GCGCTATGGCATCCGTGGCATCCCGACTCTGCTGCTGTTCCGTAACGGCGAA
GGTACCATGTGTGACCGTATTATCCACCTGACTGACGACTGCTTCGACACGGA
TGTACTCCGCGCGGATGGGGCGCGTCTCGTCGACTTCTGGGCAGAGTGGTGC
GGTCCTCGTATGTGTATCGCCCCTATTCTGGATGAGCGTGCTGACGAATATCA
GGGTCGCCTGACCGTTGCACGTCTGAATATCGATCAAAACCCTGGCACTGCA
CCGCGCTATGGCATCCGTGGTATCCCGACTCTCCTGCTGTTCCGTAACGGCGA
AGAATTCATGTGTGATCGTATCATTCACCTGACTGACGACTGTTTTGACACGG
ATGTTCTCCGCGCGGACGGGGCGCGTCTCGTAGATTTCTGGGCAGAGTGGTG
CGGCCCGCGTATGTGTATCGCCCCGATTCTCGATGAACGTGCTGACGAATATC
AGGGTCGCCTGACCGTTGCCCGTCTGAACATCGATCAAAACCCTGGCACTGC
ACCGCGCTATGGCATCCGTGGTATCCCAACTCTGCTGCTGTTCCGTAACGGCG
AAACCGGTATGTGCGATCGCATTATTCACCTGACTGATGACTGCTTTGACACG
GACGTACTCCGCGCGGACGGGGCGCGCCTCGTCGATTTCTGGGCAGAGTGGT
GCGGTCCGCGTATGTGTATCGCGCCGATTCTGGATGAACGTGCGGACGAATA
TCAGGGCCGCCTGACTGTTGCACGTCTGAACATCGACCAAAACCCTGGCACT
GCGCCTCGCTATGGCATCCGTGGTATCCCGACTCTGCTGCTCTTCCGTAACGG
CGAAGCCGGCATGTGTGATCGTATCATTCACCTGACTGATGACTGCTTCGACA
CGGATGTACTCCGCGCCGACGGGGCGATCCTCGTCGATTTCTGGGCAGAATG
GTGCGGTCCGCGTATGTGTATCGCTCCGATCCTGGATGAAATCGCTGATGAAT
ATCAGGGCCGCCTCACCGTTGCACGTCTGAATATCGATCAAAACCCTGGTAC
TGCGCCGCGCTATGGTATCCGTGGCATCCCGACTCTTCTGCTTTTCCGTAACG
GCGAAGCCGGCACCGGTGAATTCGGTACCAGCGCTCACCACCACCACCACCA
CCATCATCATCACGTTTAAAC (SEQ ID NO:13)

FIG. 2B

TRANSLATION OF pTrc BH 60kd CONSTRUCT

```
  1 MHGSMCDRII HLTDDCFDTD VLRADGARLV DFWAEWCGPR MCIAPILDER
 51 ADEYQGRLTV ARLNIDQNPG TSAMCDRIIH LTDDCFDTDV LRADGARLVD
101 FWAEWCGPRM CIAPILDERA DEYQGRLTVA RLNIDQNPGT APRYGIRGIP
151 TLLLFRNGEG TMCDRIIHLT DDCFDTDVLR ADGARLVDFW AEWCGPRMCI
201 APILDERADE YQGRLTVARL NIDQNPGTAP RYGIRGIPTL LLFRNGEEFM
251 CDRIIHLTDD CFDTDVLRAD GARLVDFWAE WCGPRMCIAP ILDERADEYQ
301 GRLTVARLNI DQNPGTAPRY GIRGIPTLLL FRNGETGMCD RIIHLTDDCF
351 DTDVLRADGA RLVDFWAEWC GPRMCIAPIL DERADEYQGR LTVARLNIDQ
401 NPGTAPRYGI RGIPTLLLFR NGEAGMCDRI IHLTDDCFDT DVLRADGAIL
451 VDFWAEWCGP RMCIAPILDE IADEYQGRLT VARLNIDQNP GTAPRYGIRG
501 IPTLLLFRNG EAGTGEFGTS AHHHHHHHHH HV
```

SEQ ID NO:8

*FIG. 3B*

TRANSLATION OF pTrc BH 30kd CONSTRUCT

|     |            |            |            |            |            |
|-----|------------|------------|------------|------------|------------|
| 1   | MHGSMCDRII | HLTDDCFDTD | VLRADGARLV | DFWAEWCGPR | MCIAPILDER |
| 51  | ADEYQGRLTV | ARLNIDQNPG | TSAMCDRIIH | LTDDCFDTDV | LRADGARLVD |
| 101 | FWAEWCGPRM | CIAPILDERA | DEYQGRLTVA | RLNIDQNPGT | APRYGIRGIP |
| 151 | TLLLFRNGEG | TMCDRIIHLT | DDCFDTDVLR | ADGARLVDFW | AEWCGPRMCI |
| 201 | APILDERADE | YQGRLTVARL | NIDQNPGTAP | RYGIRGIPTL | LLFRNGEEFG |
| 251 | TSAHHHHHHH | HHHV       |            |            |            |

SEQ ID NO: 15

FIG. 4B

TRANSLATION OF pTrc BH 40kd CONSTRUCT

| | | | | |
|---|---|---|---|---|
| 1   MHGSMCDRII | HLTDDCFDTD | VLRADGARLV | DFWAEWCGPR | MCIAPILDER |
| 51  ADEYQGRLTV | ARLNIDQNPG | TSAMCDRIIH | LTDDCFDTDV | LRADGARLVD |
| 101 FWAEWCGPRM | CIAPILDERA | DEYQGRLTVA | RLNIDQNPGT | APRYGIRGIP |
| 151 TLLLFRNGEG | TMCDRIIHLT | DDCFDTDVLR | ADGARLVDFW | AEWCGPRMCI |
| 201 APILDERADE | YQGRLTVARL | NIDQNPGTAP | RYGIRGIPTL | LLFRNGEEFM |
| 251 CDRIIHLTDD | CFDTDVLRAD | GARLVDFWAE | WCGPRMCIAP | ILDERADEYQ |
| 301 GRLTVARLNI | DQNPGTAPRY | GIRGIPTLLL | FRNGETGEFG | TSAHHHHHHH |
| 351 HHHV | | | | |

SEQ ID NO: 16

*FIG. 5B*

TRANSLATION OF pTrc BH 50kd CONSTRUCT

|  |  |  |  |  |  |
|---:|---|---|---|---|---|
| 1 | MHGSMCDRII | HLTDDCFDTD | VLRADGARLV | DFWAEWCGPR | MCIAPILDER |
| 51 | ADEYQGRLTV | ARLNIDQNPG | TSAMCDRIIH | LTDDCFDTDV | LRADGARLVD |
| 101 | FWAEWCGPRM | CIAPILDERA | DEYQGRLTVA | RLNIDQNPGT | APRYGIRGIP |
| 151 | TLLLFRNGEG | TMCDRIIHLT | DDCFDTDVLR | ADGARLVDFW | AEWCGPRMCI |
| 201 | APILDERADE | YQGRLTVARL | NIDQNPGTAP | RYGIRGIPTL | LLFRNGEEFM |
| 251 | CDRIIHLTDD | CFDTDVLRAD | GARLVDFWAE | WCGPRMCIAP | ILDERADEYQ |
| 301 | GRLTVARLNI | DQNPGTAPRY | GIRGIPTLLL | FRNGETGEFG | TSAHHHHHHH |
| 351 | DTDVLRADGA | RLVDFWAEWC | GPRMCIAPIL | DERADEYQGR | LTVARLNIDQ |
| 401 | NPGTAPRYGI | RGIPTLLLFR | NGEAGTGEFG | TSAHHHHHHH | HHHV |

SEQ ID NO: 17

*FIG. 6B*

SEQUENCE OF 50 kDa INSERT

ATGTGTGATCGTATTATTCATCTGACTGATGACTGCTTTGACACGGACGTACT
CCGTGCGGACGGGGCGCGTCTCGTCGATTTCTGGGCAGAGTGGTGCGGTCCA
CGTATGTGTATCGCGCCGATTCTGGATGAACGTGCAGACGAATATCAAGGCC
GCCTGACCGTTGCACGCCTGAACATCGATCAAAACCCTGGTACTGCGCCGCG
CTATGGCATCCGTGGCATCCCGACTCTGCTGCTGTTCCGTAACGGCGAAGGTA
CCATGTGTGACCGTATTATCCACCTGACTGACGACTGCTTCGACACGGATGTA
CTCCGCGCGGATGGGGCGCGTCTCGTCGACTTCTGGGCAGAGTGGTGCGGTC
CTCGTATGTGTATCGCCCCTATTCTGGATGAGCGTGCTGACGAATATCAGGGT
CGCCTGACCGTTGCACGTCTGAATATCGATCAAACCCTGGCACTGCACCGC
GCTATGGCATCCGTGGTATCCCGACTCTCCTGCTGTTCCGTAACGGCGAAGAA
TTCATGTGTGATCGTATCATTCACCTGACTGACGACTGTTTTGACACGGATGT
TCTCCGCGCGGACGGGGCGCGTCTCGTAGATTTCTGGGCAGAGTGGTGCGGC
CCGCGTATGTGTATCGCCCCGATTCTCGATGAACGTGCTGACGAATATCAGG
GTCGCCTGACCGTTGCCCGTCTGAACATCGATCAAAACCCTGGCACTGCACC
GCGCTATGGCATCCGTGGTATCCCAACTCTGCTGCTGTTCCGTAACGGCGAAA
CCGGTATGTGCGATCGCATTATTCACCTGACTGATGACTGCTTTGACACGGAC
GTACTCCGCGCGGACGGGGCGCGCCTCGTCGATTTCTGGGCAGAGTGGTGCG
GTCCGCGTATGTGTATCGCGCCGATTCTGGATGAACGTGCGGACGAATATCA
GGGCCGCCTGACTGTTGCACGTCTGAACATCGACCAAAACCCTGGCACTGCG
CCTCGCTATGGCATCCGTGGTATCCCGACTCTGCTGCTCTTCCGTAACGGCGA
AGCCGGCATGTGTGATCGTATCATTCACCTGACTGATGACTGCTTCGACACGG
ATGTACTCCGCGCCGACGGGGCGATCCTCGTCGATTTCTGGGCAGAATGGTG
CGGTCCGCGTATGTGTATCGCTCCGATCCTGGATGAAATCGCTGATGAATATC
AGGGCCGCCTCACCGTTGCACGTCTGAATATCGATCAAAACCCTGGTACTGC
GCCGCGCTATGGTATCCGTGGCATCCCGACTCTTCTGCTTTTCCGTAACGGCG
AA

SEQ ID NO:37

*FIG. 7*

TRANSLATION OF pTrc 110kd

```
  1 MHGSMCDRII HLTDDCFDTD VLRADGARLV DFWAEWCGPR MCIAPILDER
 51 ADEYQGRLTV ARLNIDQNPG TAPRYGIRGI PTLLLFRNGE GTMCDRIIHL
101 TDDCFDTDVL RADGARLVDF WAEWCGPRMC IAPILDERAD EYQGRLTVAR
151 LNIDQNPGTA PRYGIRGIPT LLLFRNGEEF MCDRIIHLTD DCFDTDVLRA
201 DGARLVDFWA EWCGPRMCIA PILDERADEY QGRLTVARLN IDQNPGTAPR
251 YGIRGIPTLL LFRNGETGMC DRIIHLTDDC FDTDVLRADG ARLVDFWAEW
301 CGPRMCIAPI LDERADEYQG RLTVARLNID QNPGTAPRYG IRGIPTLLLF
351 RNGEAGMCDR IIHLTDDCFD TDVLRADGAI LVDFWAEWCG PRMCIAPILD
401 EIADEYQGRL TVARLNIDQN PGTAPRYGIR GIPTLLLFRN GELEMCDRII
451 HLTDDCFDTD VLRADGARLV DFWAEWCGPR MCIAPILDER ADEYQGRLTV
501 ARLNIDQNPG TAPRYGIRGI PTLLLFRNGE GTMCDRIIHL TDDCFDTDVL
551 RADGARLVDF WAEWCGPRMC IAPILDERAD EYQGRLTVAR LNIDQNPGTA
601 PRYGIRGIPT LLLFRNGEEF MCDRIIHLTD DCFDTDVLRA DGARLVDFWA
651 EWCGPRMCIA PILDERADEY QGRLTVARLN IDQNPGTAPR YGIRGIPTLL
701 LFRNGETGMC DRIIHLTDDC FDTDVLRADG ARLVDF1JAEW CGPRMCIAPI
751 LDERADEYQG RLTVARLNID QNPGTAPRYG IRGIPTLLLF RNGEAGMCDR
801 IIHLTDDCFD TDVLRADGAI LVDFWAEWCG PRMCIAPILD EIADEYQGRL
851 TVARLNIDQN PGTAPRYGIR GIPTLLLFRN GEHHHHHHHH HHV
```

SEQ ID NO: 38

*FIG. 8B*

TRANSLATION OF pTrc 160kd

```
   1 MHGSMCDRII HLTDDCFDTD VLRADGARLV DFWAEWCGPR MCIAPILDER
  51 ADEYQGRLTV ARLNIDQNPG TAPRYGIRGI PTLLLFRNGE GTMCDRIIHL
 101 TDDCFDTDVL RADGARLVDF WAEWCGPRMC IAPILDERAD EYQGRLTVAR
 151 LNIDQNPGTA PRYGIRGIPT LLLFRNGEEF MCDRIIHLTD DCFDTDVLRA
 201 DGARLVDFWA EWCGPRMCIA PILDERADEY QGRLTVARLN IDQNPGTAPR
 251 YGIRGIPTLL LFRNGETGMC DRIIHLTDDC FDTDVLRADG ARLVDFWAEW
 301 CGPRMCIAPI LDERADEYQG RLTVARLNID QNPGTAPRYG IRGIPTLLLF
 351 RNGEAGMCDR IIHLTDDCFD TDVLRADGAI LVDFWAEWCG PRMCIAPILD
 401 EIADEYQGRL TVARLNIDQN PGTAPRYGIR GIPTLLLFRN GELEMCDRII
 451 HLTDDCFDTD VLRADGARLV DFWAEWCGPR MCIAPILDER ADEYQGRLTV
 501 ARLNIDQNPG TAPRYGIRGI PTLLLFRNGE GTMCDRIIHL TDDCFDTDVL
 551 RADGARLVDF WAEWCGPRMC IAPILDERAD EYQGRLTVAR LNIDQNPGTA
 601 PRYGIRGIPT LLLFRNGEEF MCDRIIHLTD DCFDTDVLRA DGARLVDFWA
 651 EWCGPRMCIA PILDERADEY QGRLTVARLN IDQNPGTAPR YGIRGIPTLL
 701 LFRNGETGMC DRIIHLTDDC FDTDVLRADG ARLVDF1JAEW CGPRMCIAPI
 751 LDERADEYQG RLTVARLNID QNPGTAPRYG IRGIPTLLLF RNGEAGMCDR
 801 IIHLTDDCFD TDVLRADGAI LVDFWAEWCG PRMCIAPILD EIADEYQGRL
 851 TVARLNIDQN PGTAPRYGIR GIPTLLLFRN GEPRMCDRII HLTDDCFDTD
 901 VLRADGARLV DFWAEWCGPR MCIAPILDER ADEYQGRLTV ARLNIDQNPG
 951 TAPRYGIRGI PTLLLFRNGE GTMCDRIIHL TDDCFDTDVL RADGARLVDF
1001 WAEWCGPRMC IAPILDERAD EYQGRLTVAR LNIDQNPGTA PRYGIRGIPT
1051 LLLFRNGEEF MCDRIIHLTD DCFDTDVLRA DGARLVDFWA EWCGPRMCIA
1101 PILDERADEY QGRLTVARLN IDQNPGTAPR YGIRGIPTLL LFRNGETGMC
1151 DRIIHLTDDC FDTDVLRADG ARLVDFWAEW CGPRMCIAPI LDERADEYQG
1201 RLTVARLNID QNPGTAPRYG IRGIPTLLLF RNGEAGMCDR IIHLTDDCFD
1251 TDVLRADGAI LVDFWAEWCG PRMCIAPILD EIADEYQGRL TVARLNIDQN
1301 PGTAPRYGIR GIPTLLLFRN GEHHHHHHHH HHV
```

SEQ ID NO: 39

FIG. 9B

```
CCTAGGATGATAGATCCCGTCGTTTTACAACGTCGTGACTGGGAAAACCCTGGCGTT
ACCCAACTTAATCGCCTTGCAGCACATCCCCCTTTCGCCAGCTGGCGTAATAGCGAA
GAGGCCCGCACCGATCGCCCTTCCCAACAGTTGCGCAGCCTGAATGGCGAATGGCGC
TTTGCCTGGTTTCCGGTACCAGAAGCGGTGCCGGAAAGCTGGCTGGAGTGCGATCTT
CCTGAGGCCGATACTGTCGTCGTCCCCTCAAACTGGCAGATGCACGGTTACGATGCG
CCCATCTACACCAACGTAACCTATCCCATTACGGTCAATCCGCCGTTTGTTCCCACGG
AGAATCCGACGGGTTGTTACTCGCTCACATTTAATGTTGATGAAAGCTGGCTACAGG
AAGGCCAGACGCGAATTATTTTGATGGCGTTAACTCGGCGTTTCATCTGTGGTGCA
ACGGGCGCTGGGTCGGTTACGGCCAGGACAGTCGTTTGCCGTCTGAATTTGACCTGA
GCGCATTTTTACGCGCCGGAGAAAACCGCCTCGCGGTGATGGTGCTGCGTTGGAGTG
ACGGCAGTTATCTGGAAGATCAGGATATGTGGCGGATGAGCGGCATTTTCCGTGACG
TCTCGTTGCTGCATAAACCGACTACACAAATCAGCGATTTCCATGTTGCCACTCGCTT
TAATGATGATTTCAGCCGCGCTGTACTGGAGGCTGAAGTTCAGATGTGCGGCGAGTT
GCGTGACTACCTACGGGTAACAGTTTCTTTATGGCAGGGTGAAACGCAGGTCGCCAG
CGGCACCGCGCCTTTCGGCGGTGAAATTATCGATGAGCGTGGTGGTTATGCCGATCG
CGTCACACTACGTCTGAACGTCGAAAACCCGAAACTGTGGAGCGCCGAAATCCCGA
ATCTCTATCGTGCGGTGGTTGAACTGCACACCGCCGACGGCACGCTGATTGAAGCAG
AAGCCTGCGATGTCGGTTTCCGCGAGGTGCGGATTGAAAATGGTCTGCTGCTGCTGA
ACGGCAAGCCGTTGCTGATTCGAGGCGTTAACCGTCACGAGCATCATCCTCTGCATG
GTCAGGTCATGGATGAGCAGACGATGGTGCAGGATATCCTGCTGATGAAGCAGAAC
AACTTTAACGCCGTGCGCTGTTCGCATTATCCGAACCATCCGCTGTGGTACACGCTGT
GCGACCGCTACGGCCTGTATGTGGTGGATGAAGCCAATATTGAAACCCACGGCATGG
TGCCAATGAATCGTCTGACCGATGATCCGCGCTGGCTACCGGCGATGAGCGAACGCG
TAACGCGAATGGTGCAGCGCGATCGTAATCACCCGAGTGTGATCATCTGGTCGCTGG
GGAATGAATCAGGCCACGGCGCTAATCACGACGCGCTGTATCGCTGGATCAAATCTG
TCGATCCTTCCCGCCCGGTGCAGTATGAAGGCGGCGGAGCCGACACCACGGCCACCG
ATATTATTTGCCCGATGTACGCGCGCGTGGATGAAGACCAGCCCTTCCCGGCTGTGC
CGAAATGGTCCATCAAAAAATGGCTTTCGCTACCTGGAGAGACGCGCCCGCTGATCC
TTTGCGAATACGCCCACGCGATGGGTAACAGTCTTGGCGGTTTCGCTAAATACTGGC
AGGCGTTTCGTCAGTATCCCCGTTTACAGGGCGGCTTCGTCTGGGACTGGGTGGATC
AGTCGCTGATTAAATATGATGAAAACGGCAACCCGTGGTCGGCTTACGGCGGTGATT
TTGGCGATACGCCGAACGATCGCCAGTTCTGTATGAACGGTCTGGTCTTTGCCGACC
GCACGCCGCATCCAGCGCTGACGGAAGCAAAACACCAGCAGCAGTTTTTCCAGTTCC
GTTTATCCGGGCAAACCATCGAAGTGACCAGCGAATACCTGTTCCGTCATAGCGATA
ACGAGCTCCTGCACTGGATGGTGGCGCTGGATGGTAAGCCGCTGGCAAGCGGTGAA
GTGCCTCTGGATGTCGCTCCACAAGGTAAACAGTTGATTGAACTGCCTGAACTACCG
CAGCCGGAGAGCGCCGGGCAACTCTGGCTCACAGTACGCGTAGTGCAACCGAACGC
GACCGCATGGTCAGAAGCCGGGCACATCAGCGCCTGGCAGCAGTGGCGTCTGGCGG
AAAACCTCAGTGTGACGCTCCCCGCCGCGTCCCACGCCATCCCGCATCTGACCACCA
GCGAAATGGATTTTTGCATCGAGCTGGGTAATAAGCGTTGGCAATTTAACCGCCAGT
CAGGCTTTCTTTCACAGATGTGGATTGGCGATAAAAAACAACTGCTGACGCCGCTGC
GCGATCAGTTCACCCGTGCACCGCTGGATAACGACATTGGCGTAAGTGAAGCGACCC
GCATTGACCCTAACGCCTGGGTCGAACGCTGGAAGGCGGCGGGCCATTACCAGGCC
GAAGCAGCGTTGTTGCAGTGCACGGCAGATACACTTGCTGATGCGGTGCTGATTACG
ACCGCTCACGCGTGGCAGCATCAGGGGAAAACCTTATTTATCAGCCGGAAAACCTAC
CGGATTGATGGTAGTGGTCAAATGGCGATTACCGTTGATGTTGAAGTGGCGAGCGAT
ACACCGCATCCGGCGCGGATTGGCCTGAACTGCCAGCTGGCGCAGGTAGCAGAGCG
GGTAAACTGGCTCGGATTAGGGCCGCAAGAAAACTATCCCCCTAGG
```
SEQ ID NO:40

*FIG. 10*

```
MHGSMCDRIIHLTDDCFDTDVLRADGARLVDFWAEWCGPRMCIAPILDERADEYQGRL
TVARLNIDQNPGTAPRYGIRGIPTLLLFRNGEGTMCDRIIHLTDDCFDTDVLRADGARLV
DFWAEWCGPRMCIAPILDERADEYQGRLTVARLNIDQNPGTAPRYGIRGIPTLLLFRNGE
EFMCDRIIHLTDDCFDTDVLRADGARLVDFWAEWCGPRMCIAPILDERADEYQGRLTVA
RLNIDQNPGTAPRYGIRGIPTLLLFRNGETGMCDRIIHLTDDCFDTDVLRADGARLVDFW
AEWCGPRMCIAPILDERADEYQGRLTVARLNIDQNPGTAPRYGIRGIPTLLLFRNGEAGM
CDRIIHLTDDCFDTDVLRADGAILVDFWAEWCGPRMCIAPILDEIADEYQGRLTVARLNI
DQNPGTAPRYGIRGIPTLLLFRNGELEMCDRIIHLTDDCFDTDVLRADGARLVDFWAEW
CGPRMCIAPILDERADEYQGRLTVARLNIDQNPGTAPRYGIRGIPTLLLFRNGEGTMCDRI
IHLTDDCFDTDVLRADGARLVDFWAEWCGPRMCIAPILDERADEYQGRLTVARLNIDQN
PGTAPRYGIRGIPTLLLFRNGEEFMCDRIIHLTDDCFDTDVLRADGARLVDFWAEWCGPR
MCIAPILDERADEYQGRLTVARLNIDQNPGTAPRYGIRGIPTLLLFRNGETGMCDRIIHLT
DDCFDTDVLRADGARLVDFWAEWCGPRMCIAPILDERADEYQGRLTVARLNIDQNPGT
APRYGIRGIPTLLLFRNGEAGMCDRIIHLTDDCFDTDVLRADGAILVDFWAEWCGPRMCI
APILDEIADEYQGRLTVARLNIDQNPGTAPRYGIRGIPTLLLFRNGEPRMIDPVVLQRRDW
ENPGVTQLNRLAAHPPFASWRNSEEARTDRPSQQLRSLNGEWRFAWFPVPEAVPESWLE
CDLPEADTVVVPSNWQMHGYDAPIYTNVTYPITVNPPFVPTENPTGCYSLTFNVDESWL
QEGQTRIIFDGVNSAFHLWCNGRWVGYGQDSRLPSEFDLSAFLRAGENRLAVMVLRWS
DGSYLEDQDMWRMSGIFRDVSLLHKPTTQISDFHVATRFNDDFSRAVLEAEVQMCGELR
DYLRVTVSLWQGETQVASGTAPFGGEIIDERGGYADRVTLRLNVENPKLWSAEIPNLYR
AVVELHTADGTLIEAEACDVGFREVRIENGLLLLNGKPLLIRGVNREHHPLHGQVMDE
QTMVQDILLMKQNNFNAVRCSHYPNHPLWYTLCDRYGLYVVDEANIETHGMVPMNRL
TDDPRWLPAMSERVTRMVQRDRNHPSVIIWSLGNESGHGANHDALYRWIKSVDPSRPV
QYEGGGADTTATDIICPMYARVDEDQPFPAVPKWSIKKWLSLPGETRPLILCEYAHAMG
NSLGGFAKYWQAFRQYPRLQGGFVWDWVDQSLIKYDENGNPWSAYGGDFGDTPNDR
QFCMNGLVFADRTPHPALTEAKHQQQFFQFRLSGQTIEVTSEYLFRHSDNELLHWMVAL
DGKPLASGEVPLDVAPQGKQLIELPELPQPESAGQLWLTVRVVQPNATAWSEAGHISAW
QQWRLAENLSVTLPAASHAIPHLTTSEMDFCIELGNKRWQFNRQSGFLSQMWIGDKKQL
LTPLRDQFTRAPLDNDIGVSEATRIDPNAWVERWKAAGHYQAEAALLQCTADTLADAV
LITTAHAWQHQGKTLFISRI(TYRIDGSGQMAITVDVEVASDTPHPARIGLNCQLAQVAER
VNWLGLGPQENYPPRMCDRIIHLTDDCFDTDVLRADGARLVDFWAEWCGPRMCIAPIL
DERADEYQGRLTVARLNIDQNPGTAPRYGIRGIPTLLLFRNGEGTMCDRIIHLTDDCFDT
DVLRADGARLVDFWAEWCGPRMCIAPILDERADEYQGRLTVARLNIDQNPGTAPRYGIR
GIPTLLLFRNGEEFMCDRIIHLTDDCFDTDVLRADGARLVDFWAEWCGPRMCIAPILDER
ADEYQGRLTVARLNIDQNPGTAPRYGIRGIPTLLLFRNGETGMCDRIIHLTDDCFDTDVL
RADGARLVDFWAEWCGPRMCIAPILDERADEYQGRLTVARLNIDQNPGTAPRYGIRGIP
TLLLFRNGEAGMCDRIIHLTDDCFDTDVLRADGAILVDFWAEWCGPRMCIAPILDEIADE
YQGRTVARLNIDQNPGTAPRYGIRGIPTLLLFRNGEHHHHHHHHHV
```

SEQ ID NO:41

*FIG. 11B*

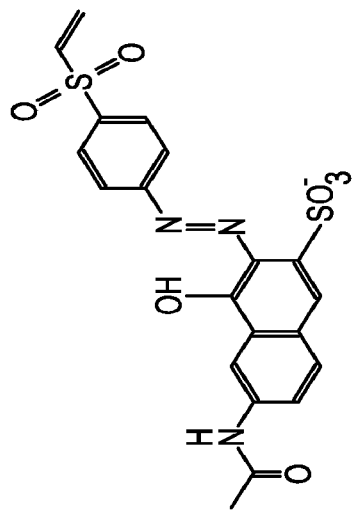
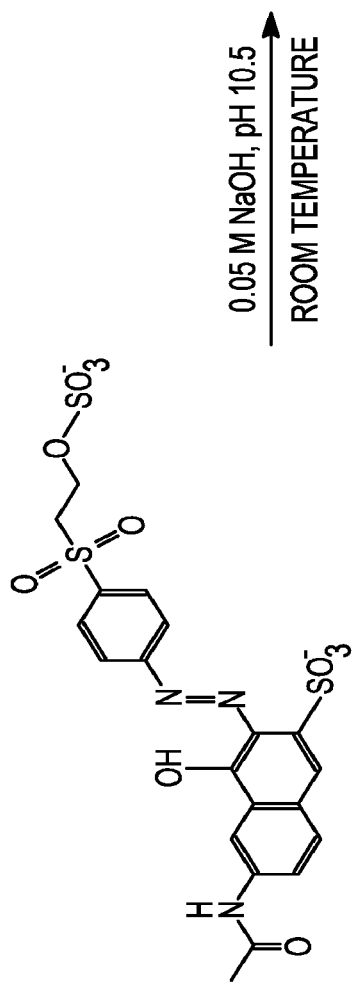
FIG. 13

SEQUENCE LISTING

<160> NUMBER OF SEQ ID NOS: 41

<210> SEQ ID NO 1
<211> LENGTH: 109
<212> TYPE: PRT
<213> ORGANISM: Artificial
<220> FEATURE:
<223> OTHER INFORMATION: Escherchia coli

<400> SEQUENCE: 1

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
                100                 105

<210> SEQ ID NO 2
<211> LENGTH: 105
<212> TYPE: PRT
<213> ORGANISM: Artificial
<220> FEATURE:
<223> OTHER INFORMATION: Homo sapiens

<400> SEQUENCE: 2

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
                20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
                100                 105

<210> SEQ ID NO 3
<211> LENGTH: 85
<212> TYPE: PRT
<213> ORGANISM: Artificial
<220> FEATURE:
<223> OTHER INFORMATION: Escherchia coli

<400> SEQUENCE: 3

Met Gln Thr Val Ile Phe Gly Arg Ser Gly Cys Pro Tyr Cys Val Arg
1               5                   10                  15

Ala Lys Asp Leu Ala Glu Lys Leu Ser Asn Glu Arg Asp Asp Phe Gln
                20                  25                  30

```
Tyr Gln Tyr Val Asp Ile Arg Ala Glu Gly Ile Thr Lys Glu Asp Leu
            35                  40                  45

Gln Gln Lys Ala Gly Lys Pro Val Glu Thr Val Pro Gln Ile Phe Val
 50                  55                  60

Asp Gln Gln His Ile Gly Gly Tyr Thr Asp Phe Ala Ala Trp Val Lys
 65                  70                  75                  80

Glu Asn Leu Asp Ala
                85

<210> SEQ ID NO 4
<211> LENGTH: 215
<212> TYPE: PRT
<213> ORGANISM: Artificial
<220> FEATURE:
<223> OTHER INFORMATION: Escherchia coli

<400> SEQUENCE: 4

Met Lys Leu Tyr Ile Tyr Asp His Cys Pro Tyr Cys Leu Lys Ala Arg
 1               5                  10                  15

Met Ile Phe Gly Leu Lys Asn Ile Pro Val Glu Leu His Val Leu Leu
            20                  25                  30

Asn Asp Asp Ala Glu Thr Pro Thr Arg Met Val Gly Gln Lys Gln Val
        35                  40                  45

Pro Ile Leu Gln Lys Asp Ser Arg Tyr Met Pro Glu Ser Met Asp
 50                  55                  60

Ile Val His Tyr Val Asp Lys Leu Asp Gly Lys Pro Leu Leu Thr Gly
 65                  70                  75                  80

Lys Arg Ser Pro Ala Ile Glu Glu Trp Leu Arg Lys Val Asn Gly Tyr
                85                  90                  95

Ala Asn Lys Leu Leu Leu Pro Arg Phe Ala Lys Ser Ala Phe Asp Glu
            100                 105                 110

Phe Ser Thr Pro Ala Ala Arg Lys Tyr Phe Val Asp Lys Lys Glu Ala
        115                 120                 125

Ser Ala Gly Asn Phe Ala Asp Leu Leu Ala His Ser Asp Gly Leu Ile
    130                 135                 140

Lys Asn Ile Ser Asp Asp Leu Arg Ala Leu Asp Lys Leu Ile Val Lys
145                 150                 155                 160

Pro Asn Ala Val Asn Gly Glu Leu Ser Glu Asp Ile Gln Leu Phe
                165                 170                 175

Pro Leu Leu Arg Asn Leu Thr Leu Val Ala Gly Ile Asn Trp Pro Ser
            180                 185                 190

Arg Val Ala Asp Tyr Arg Asp Asn Met Ala Lys Gln Thr Gln Ile Asn
        195                 200                 205

Leu Leu Ser Ser Met Ala Ile
    210                 215

<210> SEQ ID NO 5
<211> LENGTH: 450
<212> TYPE: PRT
<213> ORGANISM: Artificial
<220> FEATURE:
<223> OTHER INFORMATION: Escherchia coli

<400> SEQUENCE: 5

Met Thr Lys His Tyr Asp Tyr Ile Ala Ile Gly Gly Gly Ser Gly Gly
 1               5                  10                  15

Ile Ala Ser Ile Asn Arg Ala Ala Met Tyr Gly Gln Lys Cys Ala Leu
```

```
            20                  25                  30
Ile Glu Ala Lys Glu Leu Gly Gly Thr Cys Val Asn Val Gly Cys Val
            35                  40                  45
Pro Lys Lys Val Met Trp His Ala Ala Gln Ile Arg Glu Ala Ile His
        50                  55                  60
Met Tyr Gly Pro Asp Tyr Gly Phe Asp Thr Thr Ile Asn Lys Phe Asn
65                  70                  75                  80
Trp Glu Thr Leu Ile Ala Ser Arg Thr Ala Tyr Ile Asp Arg Ile His
                85                  90                  95
Thr Ser Tyr Glu Asn Val Leu Gly Lys Asn Asn Val Asp Val Ile Lys
            100                 105                 110
Gly Phe Ala Arg Phe Val Asp Ala Lys Thr Leu Glu Val Asn Gly Glu
            115                 120                 125
Thr Ile Thr Ala Asp His Ile Leu Ile Ala Thr Gly Gly Arg Pro Ser
            130                 135                 140
His Pro Asp Ile Pro Gly Val Glu Tyr Gly Ile Asp Ser Asp Gly Phe
145                 150                 155                 160
Phe Ala Leu Pro Ala Leu Pro Glu Arg Val Ala Val Val Gly Ala Gly
                165                 170                 175
Tyr Ile Ala Val Glu Leu Ala Gly Val Ile Asn Gly Leu Gly Ala Lys
            180                 185                 190
Thr His Leu Phe Val Arg Lys His Ala Pro Leu Arg Ser Phe Asp Pro
        195                 200                 205
Met Ile Ser Glu Thr Leu Val Glu Val Met Asn Ala Glu Gly Pro Gln
    210                 215                 220
Leu His Thr Asn Ala Ile Pro Lys Ala Val Val Lys Asn Thr Asp Gly
225                 230                 235                 240
Ser Leu Thr Leu Glu Leu Glu Asp Gly Arg Ser Glu Thr Val Asp Cys
                245                 250                 255
Leu Ile Trp Ala Ile Gly Arg Glu Pro Ala Asn Asp Asn Ile Asn Leu
            260                 265                 270
Glu Ala Ala Gly Val Lys Thr Asn Glu Lys Gly Tyr Ile Val Val Asp
            275                 280                 285
Lys Tyr Gln Asn Thr Asn Ile Glu Gly Ile Tyr Ala Val Gly Asp Asn
        290                 295                 300
Thr Gly Ala Val Glu Leu Thr Pro Val Ala Val Ala Ala Gly Arg Arg
305                 310                 315                 320
Leu Ser Glu Arg Leu Phe Asn Asn Lys Pro Asp Glu His Leu Asp Tyr
                325                 330                 335
Ser Asn Ile Pro Thr Val Val Phe Ser His Pro Pro Ile Gly Thr Val
            340                 345                 350
Gly Leu Thr Glu Pro Gln Ala Arg Glu Gln Tyr Gly Asp Asp Gln Val
            355                 360                 365
Lys Val Tyr Lys Ser Ser Phe Thr Ala Met Tyr Thr Ala Val Thr Thr
        370                 375                 380
His Arg Gln Pro Cys Arg Met Lys Leu Val Cys Val Gly Ser Glu Glu
385                 390                 395                 400
Lys Ile Val Gly Ile His Gly Ile Gly Phe Gly Met Asp Glu Met Leu
                405                 410                 415
Gln Gly Phe Ala Val Ala Leu Lys Met Gly Ala Thr Lys Lys Asp Phe
            420                 425                 430
Asp Asn Thr Val Ala Ile His Pro Thr Ala Ala Glu Glu Phe Val Thr
        435                 440                 445
```

Met Arg
    450

<210> SEQ ID NO 6
<211> LENGTH: 522
<212> TYPE: PRT
<213> ORGANISM: Artificial
<220> FEATURE:
<223> OTHER INFORMATION: Homo sapiens

<400> SEQUENCE: 6

Met Ala Leu Leu Pro Arg Ala Leu Ser Ala Gly Ala Gly Pro Ser Trp
1               5                   10                  15

Arg Arg Ala Ala Arg Ala Phe Arg Gly Phe Leu Leu Leu Leu Pro Glu
                20                  25                  30

Pro Ala Ala Leu Thr Arg Ala Leu Ser Arg Ala Met Ala Cys Arg Gln
            35                  40                  45

Glu Pro Gln Pro Gln Gly Pro Pro Ala Ala Gly Ala Val Ala Ser
    50                  55                  60

Tyr Asp Tyr Leu Val Ile Gly Gly Ser Gly Leu Ala Ser Ala
65                  70                  75                  80

Arg Arg Ala Ala Glu Leu Gly Ala Arg Ala Ala Val Val Glu Ser His
                85                  90                  95

Lys Leu Gly Gly Thr Cys Val Asn Val Gly Cys Val Pro Lys Lys Val
            100                 105                 110

Met Trp Asn Thr Ala Val His Ser Glu Phe Met His Asp His Ala Asp
        115                 120                 125

Tyr Gly Phe Pro Ser Cys Glu Gly Lys Phe Asn Trp Arg Val Ile Lys
    130                 135                 140

Glu Lys Arg Asp Ala Tyr Val Ser Arg Leu Asn Ala Ile Tyr Gln Asn
145                 150                 155                 160

Asn Leu Thr Lys Ser His Ile Glu Ile Ile Arg Gly His Ala Ala Phe
                165                 170                 175

Thr Ser Asp Pro Lys Pro Thr Ile Glu Val Ser Gly Lys Lys Tyr Thr
            180                 185                 190

Ala Pro His Ile Leu Ile Ala Thr Gly Gly Met Pro Ser Thr Pro His
        195                 200                 205

Glu Ser Gln Ile Pro Gly Ala Ser Leu Gly Ile Thr Ser Asp Gly Phe
    210                 215                 220

Phe Gln Leu Glu Glu Leu Pro Gly Arg Ser Val Ile Val Gly Ala Gly
225                 230                 235                 240

Tyr Ile Ala Val Glu Met Ala Gly Ile Leu Ser Ala Leu Gly Ser Lys
                245                 250                 255

Thr Ser Leu Met Ile Arg His Asp Lys Val Leu Arg Ser Phe Asp Ser
            260                 265                 270

Met Ile Ser Thr Asn Cys Thr Glu Glu Leu Glu Asn Ala Gly Val Glu
        275                 280                 285

Val Leu Lys Phe Ser Gln Val Lys Glu Val Lys Lys Thr Leu Ser Gly
    290                 295                 300

Leu Glu Val Ser Met Val Thr Ala Val Pro Gly Arg Leu Pro Val Met
305                 310                 315                 320

Thr Met Ile Pro Asp Val Asp Cys Leu Leu Trp Ala Ile Gly Arg Val
                325                 330                 335

Pro Asn Thr Lys Asp Leu Ser Leu Asn Lys Leu Gly Ile Gln Thr Asp
            340                 345                 350

Asp Lys Gly His Ile Ile Val Asp Glu Phe Gln Asn Thr Asn Val Lys
            355                 360                 365

Gly Ile Tyr Ala Val Gly Asp Val Cys Gly Lys Ala Leu Leu Thr Pro
        370                 375                 380

Val Ala Ile Ala Ala Gly Arg Lys Leu Ala His Arg Leu Phe Glu Tyr
385                 390                 395                 400

Lys Glu Asp Ser Lys Leu Asp Tyr Asn Asn Ile Pro Thr Val Phe
                405                 410                 415

Ser His Pro Pro Ile Gly Thr Val Gly Leu Thr Glu Asp Glu Ala Ile
                420                 425                 430

His Lys Tyr Gly Ile Glu Asn Val Lys Thr Tyr Ser Thr Ser Phe Thr
            435                 440                 445

Pro Met Tyr His Ala Val Thr Lys Arg Lys Thr Lys Cys Val Met Lys
        450                 455                 460

Met Val Cys Ala Asn Lys Glu Lys Val Val Gly Ile His Met Gln
465                 470                 475                 480

Gly Leu Gly Cys Asp Glu Met Leu Gln Gly Phe Ala Val Ala Val Lys
                485                 490                 495

Met Gly Ala Thr Lys Ala Asp Phe Asp Asn Thr Val Ala Ile His Pro
                500                 505                 510

Thr Ser Ser Glu Glu Leu Val Thr Leu Arg
            515                 520

<210> SEQ ID NO 7
<211> LENGTH: 474
<212> TYPE: PRT
<213> ORGANISM: Artificial
<220> FEATURE:
<223> OTHER INFORMATION: Escherchia coli

<400> SEQUENCE: 7

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
        50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

```
Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 8
<211> LENGTH: 509
<212> TYPE: PRT
<213> ORGANISM: Artificial
<220> FEATURE:
<223> OTHER INFORMATION: Homo sapiens

<400> SEQUENCE: 8

Met Gln Ser Trp Ser Arg Val Tyr Cys Ser Leu Ala Lys Arg Gly His
1               5                   10                  15

Phe Asn Arg Ile Ser His Gly Leu Gln Gly Leu Ser Ala Val Pro Leu
            20                  25                  30

Arg Thr Tyr Ala Asp Gln Pro Ile Asp Ala Asp Val Thr Val Ile Gly
        35                  40                  45

Ser Gly Pro Gly Gly Tyr Val Ala Ala Ile Lys Ala Ala Gln Leu Gly
    50                  55                  60

Phe Lys Thr Val Cys Ile Glu Lys Asn Glu Thr Leu Gly Gly Thr Cys
65                  70                  75                  80
```

```
Leu Asn Val Gly Cys Ile Pro Ser Lys Ala Leu Leu Asn Asn Ser His
                85                  90                  95

Tyr Tyr His Met Ala His Gly Lys Asp Phe Ala Ser Arg Gly Ile Glu
            100                 105                 110

Met Ser Glu Val Arg Leu Asn Leu Asp Lys Met Met Glu Gln Lys Ser
        115                 120                 125

Thr Ala Val Lys Ala Leu Thr Gly Gly Ile Ala His Leu Phe Lys Gln
    130                 135                 140

Asn Lys Val Val His Val Asn Gly Tyr Gly Lys Ile Thr Gly Lys Asn
145                 150                 155                 160

Gln Val Thr Ala Thr Lys Ala Asp Gly Gly Thr Gln Val Ile Asp Thr
                165                 170                 175

Lys Asn Ile Leu Ile Ala Thr Gly Ser Glu Val Thr Pro Phe Pro Gly
            180                 185                 190

Ile Thr Ile Asp Glu Asp Thr Ile Val Ser Ser Thr Gly Ala Leu Ser
        195                 200                 205

Leu Lys Lys Val Pro Glu Lys Met Val Val Ile Gly Ala Gly Val Ile
    210                 215                 220

Gly Val Glu Leu Gly Ser Val Trp Gln Arg Leu Gly Ala Asp Val Thr
225                 230                 235                 240

Ala Val Glu Phe Leu Gly His Val Gly Gly Val Gly Ile Asp Met Glu
                245                 250                 255

Ile Ser Lys Asn Phe Gln Arg Ile Leu Gln Lys Gln Gly Phe Lys Phe
            260                 265                 270

Lys Leu Asn Thr Lys Val Thr Gly Ala Thr Lys Lys Ser Asp Gly Lys
        275                 280                 285

Ile Asp Val Ser Ile Glu Ala Ala Ser Gly Gly Lys Ala Glu Val Ile
    290                 295                 300

Thr Cys Asp Val Leu Leu Val Cys Ile Gly Arg Arg Pro Phe Thr Lys
305                 310                 315                 320

Asn Leu Gly Leu Glu Glu Leu Gly Ile Glu Leu Asp Pro Arg Gly Arg
                325                 330                 335

Ile Pro Val Asn Thr Arg Phe Gln Thr Lys Ile Pro Asn Ile Tyr Ala
            340                 345                 350

Ile Gly Asp Val Val Ala Gly Pro Met Leu Ala His Lys Ala Glu Asp
        355                 360                 365

Glu Gly Ile Ile Cys Val Glu Gly Met Ala Gly Gly Ala Val His Ile
    370                 375                 380

Asp Tyr Asn Cys Val Pro Ser Val Ile Tyr Thr His Pro Glu Val Ala
385                 390                 395                 400

Trp Val Gly Lys Ser Glu Glu Gln Leu Lys Glu Glu Gly Ile Glu Tyr
                405                 410                 415

Lys Val Gly Lys Phe Pro Phe Ala Ala Asn Ser Arg Ala Lys Thr Asn
            420                 425                 430

Ala Asp Thr Asp Gly Met Val Lys Ile Leu Gly Gln Lys Ser Thr Asp
        435                 440                 445

Arg Val Leu Gly Ala His Ile Leu Gly Pro Gly Ala Gly Glu Met Val
    450                 455                 460

Asn Glu Ala Ala Leu Ala Leu Glu Tyr Gly Ala Ser Cys Glu Asp Ile
465                 470                 475                 480

Ala Arg Val Cys His Ala His Pro Thr Leu Ser Glu Ala Phe Arg Glu
                485                 490                 495
```

```
Ala Asn Leu Ala Ala Ser Phe Gly Lys Ser Ile Asn Phe
            500                 505
```

```
<210> SEQ ID NO 9
<211> LENGTH: 279
<212> TYPE: DNA
<213> ORGANISM: Artificial
<220> FEATURE:
<223> OTHER INFORMATION: Truncated E. coli thioredoxin ORF with
      C-terminal his tag

<400> SEQUENCE: 9
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaaca ccaccaccac caccactaa                          279
```

```
<210> SEQ ID NO 10
<211> LENGTH: 279
<212> TYPE: DNA
<213> ORGANISM: Artificial
<220> FEATURE:
<223> OTHER INFORMATION: Modified truncated E. coli thioredoxin ORF
      lacking lysine with C-terminal his tag

<400> SEQUENCE: 10
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaaca ccaccaccac caccactaa                          279
```

```
<210> SEQ ID NO 11
<211> LENGTH: 92
<212> TYPE: PRT
<213> ORGANISM: Artificial
<220> FEATURE:
<223> OTHER INFORMATION: Truncated E. coli thioredoxin ORF with
      C-terminal his tag

<400> SEQUENCE: 11

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu His His His His His
                85                  90
```

```
<210> SEQ ID NO 12
<211> LENGTH: 92
<212> TYPE: PRT
<213> ORGANISM: Artificial
```

<220> FEATURE:
<223> OTHER INFORMATION: Modified truncated E. coli thioredoxin ORF lacking lysine with C-terminal his tag

<400> SEQUENCE: 12

```
Met Ser Asp Arg Ile Ile His Leu Thr Asp Asp Ser Phe Asp Thr Asp
1               5                   10                  15

Val Leu Arg Ala Asp Gly Ala Ile Leu Val Asp Phe Trp Ala Glu Trp
                20                  25                  30

Cys Gly Pro Arg Met Cys Ile Ala Pro Ile Leu Asp Glu Arg Ala Asp
            35                  40                  45

Glu Tyr Gln Gly Arg Leu Thr Val Ala Arg Leu Asn Ile Asp Gln Asn
        50                  55                  60

Pro Gly Thr Ala Pro Arg Tyr Gly Ile Arg Gly Ile Pro Thr Leu Leu
65                  70                  75                  80

Leu Phe Arg Asn Gly Glu His His His His His
                85                  90
```

<210> SEQ ID NO 13
<211> LENGTH: 1595
<212> TYPE: DNA
<213> ORGANISM: Artificial
<220> FEATURE:
<223> OTHER INFORMATION: BH 6mer ORF having six repeats of modified truncated E. coli thioredoxin ORF lacking lysine and C-terminal his tag

<400> SEQUENCE: 13

| | | | | | |
|---|---|---|---|---|---|
| agatctatgt | gtgatcgtat | tattcacctg | actgacgact | gctttgacac | ggatgtactc | 60 |
| cgcgcggacg | gggcgcgtct | cgtcgatttc | tgggcagagt | ggtgcggtcc | gcgtatgtgt | 120 |
| atcgccccga | ttctggatga | acgtgctgac | gaatatcagg | gccgcctgac | cgttgcacgt | 180 |
| ctgaacatcg | atcaaaaccc | tggcactagc | gctatgtgtg | atcgtattat | tcatctgact | 240 |
| gatgactgct | tgacacggga | cgtactccgc | gcgacgggg | cgcgtctcgt | cgatttctgg | 300 |
| gcagagtggt | gcggtccacg | tatgtgtatc | gcgccgattc | tggatgaacg | tgcagacgaa | 360 |
| tatcaaggcc | gcctgaccgt | tgcacgcctg | aacatcgatc | aaaaccctgg | tactgcgccg | 420 |
| cgctatggca | tccgtggcat | cccgactctg | ctgctgttcc | gtaacggcga | aggtaccatg | 480 |
| tgtgaccgta | ttatccacct | gactgacgac | tgcttgaca | cggatgtact | ccgcgcggat | 540 |
| ggggcgcgtc | tcgtcgactt | ctgggcagag | tggtgcggtc | ctcgtatgtg | tatcgcccct | 600 |
| attctggatg | agcgtgctga | cgaatatcag | ggtcgcctga | ccgttgcacg | tctgaatatc | 660 |
| gatcaaaacc | ctggcactgc | accgcgctat | ggcatccgtg | gtatcccgac | tctcctgctg | 720 |
| ttccgtaacg | gcgaagaatt | catgtgtgat | cgtatcattc | acctgactga | cgactgtttt | 780 |
| gacacggatg | ttctccgcgc | ggacggggcg | cgtctcgtag | atttctgggc | agagtggtgc | 840 |
| ggcccgcgta | tgtgtatcgc | cccgattctc | gatgaacgtg | ctgacgaata | tcagggtcgc | 900 |
| ctgaccgttg | cccgtctgaa | catcgatcaa | accctggca | ctgcaccgcg | ctatggcatc | 960 |
| cgtggtatcc | caactctgct | gctgttccgt | aacggcgaaa | ccggtatgtg | cgatcgcatt | 1020 |
| attcacctga | ctgatgactg | ctttgacacg | gacgtactcc | gcgcggacgg | ggcgcgcctc | 1080 |
| gtcgatttct | gggcagagtg | gtgcggtccg | cgtatgtgta | tcgcgccgat | tctggatgaa | 1140 |
| cgtgcggacg | aatatcaggg | ccgcctgact | gttgcacgtc | tgaacatcga | ccaaaaccct | 1200 |
| ggcactgcgc | tcgctatgg | catccgtggt | atcccgactc | tgctgctctt | ccgtaacggc | 1260 |
| gaagccggca | tgtgtgatcg | tatcattcac | ctgactgatg | actgcttcga | cacggatgta | 1320 |

-continued

```
ctccgcgccg acggggcgat cctcgtcgat ttctgggcag aatggtgcgg tccgcgtatg    1380
tgtatcgctc cgatcctgga tgaaatcgct gatgaatatc agggccgcct caccgttgca    1440
cgtctgaata tcgatcaaaa ccctggtact gcgccgcgct atggtatccg tggcatcccg    1500
actcttctgc ttttccgtaa cggcgaagcc ggcaccggtg aattcggtac cagcgctcac    1560
caccaccacc accaccatca tcatcacgtt taaac                                1595
```

<210> SEQ ID NO 14
<211> LENGTH: 532
<212> TYPE: PRT
<213> ORGANISM: Artificial
<220> FEATURE:
<223> OTHER INFORMATION: pTRC BH 60 kDa expression product

<400> SEQUENCE: 14

Met His Gly Ser Met Cys Asp Arg Ile Ile His Leu Thr Asp Asp Cys
1               5                   10                  15

Phe Asp Thr Asp Val Leu Arg Ala Asp Gly Ala Arg Leu Val Asp Phe
                20                  25                  30

Trp Ala Glu Trp Cys Gly Pro Arg Met Cys Ile Ala Pro Ile Leu Asp
            35                  40                  45

Glu Arg Ala Asp Glu Tyr Gln Gly Arg Leu Thr Val Ala Arg Leu Asn
        50                  55                  60

Ile Asp Gln Asn Pro Gly Thr Ser Ala Met Cys Asp Arg Ile Ile His
65                  70                  75                  80

Leu Thr Asp Asp Cys Phe Asp Thr Asp Val Leu Arg Ala Asp Gly Ala
                85                  90                  95

Arg Leu Val Asp Phe Trp Ala Glu Trp Cys Gly Pro Arg Met Cys Ile
            100                 105                 110

Ala Pro Ile Leu Asp Glu Arg Ala Asp Glu Tyr Gln Gly Arg Leu Thr
        115                 120                 125

Val Ala Arg Leu Asn Ile Asp Gln Asn Pro Gly Thr Ala Pro Arg Tyr
    130                 135                 140

Gly Ile Arg Gly Ile Pro Thr Leu Leu Leu Phe Arg Asn Gly Glu Gly
145                 150                 155                 160

Thr Met Cys Asp Arg Ile Ile His Leu Thr Asp Asp Cys Phe Asp Thr
                165                 170                 175

Asp Val Leu Arg Ala Asp Gly Ala Arg Leu Val Asp Phe Trp Ala Glu
            180                 185                 190

Trp Cys Gly Pro Arg Met Cys Ile Ala Pro Ile Leu Asp Glu Arg Ala
        195                 200                 205

Asp Glu Tyr Gln Gly Arg Leu Thr Val Ala Arg Leu Asn Ile Asp Gln
    210                 215                 220

Asn Pro Gly Thr Ala Pro Arg Tyr Gly Ile Arg Gly Ile Pro Thr Leu
225                 230                 235                 240

Leu Leu Phe Arg Asn Gly Glu Glu Phe Met Cys Asp Arg Ile Ile His
                245                 250                 255

Leu Thr Asp Asp Cys Phe Asp Thr Asp Val Leu Arg Ala Asp Gly Ala
            260                 265                 270

Arg Leu Val Asp Phe Trp Ala Glu Trp Cys Gly Pro Arg Met Cys Ile
        275                 280                 285

Ala Pro Ile Leu Asp Glu Arg Ala Asp Glu Tyr Gln Gly Arg Leu Thr
    290                 295                 300

Val Ala Arg Leu Asn Ile Asp Gln Asn Pro Gly Thr Ala Pro Arg Tyr

```
              305                 310                 315                 320
        Gly Ile Arg Gly Ile Pro Thr Leu Leu Leu Phe Arg Asn Gly Glu Thr
                        325                 330                 335

Gly Met Cys Asp Arg Ile Ile His Leu Thr Asp Asp Cys Phe Asp Thr
                        340                 345                 350

Asp Val Leu Arg Ala Asp Gly Ala Arg Leu Val Asp Phe Trp Ala Glu
                        355                 360                 365

Trp Cys Gly Pro Arg Met Cys Ile Ala Pro Ile Leu Asp Glu Arg Ala
                        370                 375                 380

Asp Glu Tyr Gln Gly Arg Leu Thr Val Ala Arg Leu Asn Ile Asp Gln
        385                 390                 395                 400

Asn Pro Gly Thr Ala Pro Arg Tyr Gly Ile Arg Gly Ile Pro Thr Leu
                        405                 410                 415

Leu Leu Phe Arg Asn Gly Glu Ala Gly Met Cys Asp Arg Ile Ile His
                        420                 425                 430

Leu Thr Asp Asp Cys Phe Asp Thr Asp Val Leu Arg Ala Asp Gly Ala
                        435                 440                 445

Ile Leu Val Asp Phe Trp Ala Glu Trp Cys Gly Pro Arg Met Cys Ile
                        450                 455                 460

Ala Pro Ile Leu Asp Glu Ile Ala Asp Glu Tyr Gln Gly Arg Leu Thr
        465                 470                 475                 480

Val Ala Arg Leu Asn Ile Asp Gln Asn Pro Gly Thr Ala Pro Arg Tyr
                        485                 490                 495

Gly Ile Arg Gly Ile Pro Thr Leu Leu Leu Phe Arg Asn Gly Glu Ala
                        500                 505                 510

Gly Thr Gly Glu Phe Gly Thr Ser Ala His His His His His His
                        515                 520                 525

His His His Val
                530

<210> SEQ ID NO 15
<211> LENGTH: 264
<212> TYPE: PRT
<213> ORGANISM: Artificial
<220> FEATURE:
<223> OTHER INFORMATION: pTRC BH 30 kDa expression product

<400> SEQUENCE: 15

Met His Gly Ser Met Cys Asp Arg Ile Ile His Leu Thr Asp Asp Cys
1               5                   10                  15

Phe Asp Thr Asp Val Leu Arg Ala Asp Gly Ala Arg Leu Val Asp Phe
                20                  25                  30

Trp Ala Glu Trp Cys Gly Pro Arg Met Cys Ile Ala Pro Ile Leu Asp
            35                  40                  45

Glu Arg Ala Asp Glu Tyr Gln Gly Arg Leu Thr Val Ala Arg Leu Asn
        50                  55                  60

Ile Asp Gln Asn Pro Gly Thr Ser Ala Met Cys Asp Arg Ile Ile His
65                  70                  75                  80

Leu Thr Asp Asp Cys Phe Asp Thr Asp Val Leu Arg Ala Asp Gly Ala
                85                  90                  95

Arg Leu Val Asp Phe Trp Ala Glu Trp Cys Gly Pro Arg Met Cys Ile
                100                 105                 110

Ala Pro Ile Leu Asp Glu Arg Ala Asp Glu Tyr Gln Gly Arg Leu Thr
                115                 120                 125

Val Ala Arg Leu Asn Ile Asp Gln Asn Pro Gly Thr Ala Pro Arg Tyr
```

```
            130                 135                 140
Gly Ile Arg Gly Ile Pro Thr Leu Leu Leu Phe Arg Asn Gly Glu Gly
145                 150                 155                 160

Thr Met Cys Asp Arg Ile Ile His Leu Thr Asp Asp Cys Phe Asp Thr
                165                 170                 175

Asp Val Leu Arg Ala Asp Gly Ala Arg Leu Val Asp Phe Trp Ala Glu
            180                 185                 190

Trp Cys Gly Pro Arg Met Cys Ile Ala Pro Ile Leu Asp Glu Arg Ala
                195                 200                 205

Asp Glu Tyr Gln Gly Arg Leu Thr Val Ala Arg Leu Asn Ile Asp Gln
        210                 215                 220

Asn Pro Gly Thr Ala Pro Arg Tyr Gly Ile Arg Gly Ile Pro Thr Leu
225                 230                 235                 240

Leu Phe Arg Asn Gly Glu Glu Phe Gly Thr Ser Ala His His His
            245                 250                 255

His His His His His His Val
            260

<210> SEQ ID NO 16
<211> LENGTH: 354
<212> TYPE: PRT
<213> ORGANISM: Artificial
<220> FEATURE:
<223> OTHER INFORMATION: pTRC BH 40 kDa expression product

<400> SEQUENCE: 16

Met His Gly Ser Met Cys Asp Arg Ile Ile His Leu Thr Asp Asp Cys
1               5                   10                  15

Phe Asp Thr Asp Val Leu Arg Ala Asp Gly Ala Arg Leu Val Asp Phe
            20                  25                  30

Trp Ala Glu Trp Cys Gly Pro Arg Met Cys Ile Ala Pro Ile Leu Asp
        35                  40                  45

Glu Arg Ala Asp Glu Tyr Gln Gly Arg Leu Thr Val Ala Arg Leu Asn
    50                  55                  60

Ile Asp Gln Asn Pro Gly Thr Ser Ala Met Cys Asp Arg Ile Ile His
65                  70                  75                  80

Leu Thr Asp Asp Cys Phe Asp Thr Asp Val Leu Arg Ala Asp Gly Ala
                85                  90                  95

Arg Leu Val Asp Phe Trp Ala Glu Trp Cys Gly Pro Arg Met Cys Ile
            100                 105                 110

Ala Pro Ile Leu Asp Glu Arg Ala Asp Glu Tyr Gln Gly Arg Leu Thr
        115                 120                 125

Val Ala Arg Leu Asn Ile Asp Gln Asn Pro Gly Thr Ala Pro Arg Tyr
    130                 135                 140

Gly Ile Arg Gly Ile Pro Thr Leu Leu Leu Phe Arg Asn Gly Glu Gly
145                 150                 155                 160

Thr Met Cys Asp Arg Ile Ile His Leu Thr Asp Asp Cys Phe Asp Thr
                165                 170                 175

Asp Val Leu Arg Ala Asp Gly Ala Arg Leu Val Asp Phe Trp Ala Glu
            180                 185                 190

Trp Cys Gly Pro Arg Met Cys Ile Ala Pro Ile Leu Asp Glu Arg Ala
        195                 200                 205

Asp Glu Tyr Gln Gly Arg Leu Thr Val Ala Arg Leu Asn Ile Asp Gln
    210                 215                 220

Asn Pro Gly Thr Ala Pro Arg Tyr Gly Ile Arg Gly Ile Pro Thr Leu
```

```
225                 230                 235                 240

Leu Leu Phe Arg Asn Gly Glu Glu Phe Met Cys Asp Arg Ile Ile His
                245                 250                 255

Leu Thr Asp Asp Cys Phe Asp Thr Asp Val Leu Arg Ala Asp Gly Ala
                260                 265                 270

Arg Leu Val Asp Phe Trp Ala Glu Trp Cys Gly Pro Arg Met Cys Ile
                275                 280                 285

Ala Pro Ile Leu Asp Glu Arg Ala Asp Glu Tyr Gln Gly Arg Leu Thr
                290                 295                 300

Val Ala Arg Leu Asn Ile Asp Gln Asn Pro Gly Thr Ala Pro Arg Tyr
305                 310                 315                 320

Gly Ile Arg Gly Ile Pro Thr Leu Leu Leu Phe Arg Asn Gly Glu Thr
                325                 330                 335

Gly Glu Phe Gly Thr Ser Ala His His His His His His His His
                340                 345                 350

His Val

<210> SEQ ID NO 17
<211> LENGTH: 444
<212> TYPE: PRT
<213> ORGANISM: Artificial
<220> FEATURE:
<223> OTHER INFORMATION: pTRC BH 50 kDa expression product

<400> SEQUENCE: 17

Met His Gly Ser Met Cys Asp Arg Ile Ile His Leu Thr Asp Asp Cys
1               5                   10                  15

Phe Asp Thr Asp Val Leu Arg Ala Asp Gly Ala Arg Leu Val Asp Phe
                20                  25                  30

Trp Ala Glu Trp Cys Gly Pro Arg Met Cys Ile Ala Pro Ile Leu Asp
                35                  40                  45

Glu Arg Ala Asp Glu Tyr Gln Gly Arg Leu Thr Val Ala Arg Leu Asn
            50                  55                  60

Ile Asp Gln Asn Pro Gly Thr Ser Ala Met Cys Asp Arg Ile Ile His
65                  70                  75                  80

Leu Thr Asp Asp Cys Phe Asp Thr Asp Val Leu Arg Ala Asp Gly Ala
                85                  90                  95

Arg Leu Val Asp Phe Trp Ala Glu Trp Cys Gly Pro Arg Met Cys Ile
                100                 105                 110

Ala Pro Ile Leu Asp Glu Arg Ala Asp Glu Tyr Gln Gly Arg Leu Thr
                115                 120                 125

Val Ala Arg Leu Asn Ile Asp Gln Asn Pro Gly Thr Ala Pro Arg Tyr
130                 135                 140

Gly Ile Arg Gly Ile Pro Thr Leu Leu Leu Phe Arg Asn Gly Glu Gly
145                 150                 155                 160

Thr Met Cys Asp Arg Ile Ile His Leu Thr Asp Asp Cys Phe Asp Thr
                165                 170                 175

Asp Val Leu Arg Ala Asp Gly Ala Arg Leu Val Asp Phe Trp Ala Glu
                180                 185                 190

Trp Cys Gly Pro Arg Met Cys Ile Ala Pro Ile Leu Asp Glu Arg Ala
                195                 200                 205

Asp Glu Tyr Gln Gly Arg Leu Thr Val Ala Arg Leu Asn Ile Asp Gln
                210                 215                 220

Asn Pro Gly Thr Ala Pro Arg Tyr Gly Ile Arg Gly Ile Pro Thr Leu
225                 230                 235                 240
```

Leu Leu Phe Arg Asn Gly Glu Glu Phe Met Cys Asp Arg Ile Ile His
                245                 250                 255

Leu Thr Asp Asp Cys Phe Asp Thr Asp Val Leu Arg Ala Asp Gly Ala
            260                 265                 270

Arg Leu Val Asp Phe Trp Ala Glu Trp Cys Gly Pro Arg Met Cys Ile
        275                 280                 285

Ala Pro Ile Leu Asp Glu Arg Ala Asp Glu Tyr Gln Gly Arg Leu Thr
    290                 295                 300

Val Ala Arg Leu Asn Ile Asp Gln Asn Pro Gly Thr Ala Pro Arg Tyr
305                 310                 315                 320

Gly Ile Arg Gly Ile Pro Thr Leu Leu Leu Phe Arg Asn Gly Glu Thr
                325                 330                 335

Gly Met Cys Asp Arg Ile Ile His Leu Thr Asp Asp Cys Phe Asp Thr
            340                 345                 350

Asp Val Leu Arg Ala Asp Gly Ala Arg Leu Val Asp Phe Trp Ala Glu
        355                 360                 365

Trp Cys Gly Pro Arg Met Cys Ile Ala Pro Ile Leu Asp Glu Arg Ala
    370                 375                 380

Asp Glu Tyr Gln Gly Arg Leu Thr Val Ala Arg Leu Asn Ile Asp Gln
385                 390                 395                 400

Asn Pro Gly Thr Ala Pro Arg Tyr Gly Ile Arg Gly Ile Pro Thr Leu
                405                 410                 415

Leu Leu Phe Arg Asn Gly Glu Ala Gly Thr Gly Glu Phe Gly Thr Ser
            420                 425                 430

Ala His His His His His His His His Val
        435                 440

<210> SEQ ID NO 18
<211> LENGTH: 21
<212> TYPE: DNA
<213> ORGANISM: Artificial
<220> FEATURE:
<223> OTHER INFORMATION: pTrCHisFOR forward primer

<400> SEQUENCE: 18
gaggtatata ttaatgtatc g                                           21

<210> SEQ ID NO 19
<211> LENGTH: 18
<212> TYPE: DNA
<213> ORGANISM: Artificial
<220> FEATURE:
<223> OTHER INFORMATION: pBAD_Rev reverse primer

<400> SEQUENCE: 19
gatttaatct gtatcagg                                               18

<210> SEQ ID NO 20
<211> LENGTH: 30
<212> TYPE: DNA
<213> ORGANISM: Artificial
<220> FEATURE:
<223> OTHER INFORMATION: 50.1_F   forward primer

<400> SEQUENCE: 20
ccggagatct atgtgtgatc gtattattca                                  30

<210> SEQ ID NO 21
<211> LENGTH: 30

<212> TYPE: DNA
<213> ORGANISM: Artificial
<220> FEATURE:
<223> OTHER INFORMATION: 50.1_R reverse primer

<400> SEQUENCE: 21
ccggctcgag ttcgccgtta cggaaaagca                              30

<210> SEQ ID NO 22
<211> LENGTH: 36
<212> TYPE: DNA
<213> ORGANISM: Artificial
<220> FEATURE:
<223> OTHER INFORMATION: 50.2_F forward primer

<400> SEQUENCE: 22
ccggctcgag atgtgtgatc gtattattca tctgac                       36

<210> SEQ ID NO 23
<211> LENGTH: 30
<212> TYPE: DNA
<213> ORGANISM: Artificial
<220> FEATURE:
<223> OTHER INFORMATION: 50.2_R reverse primer

<400> SEQUENCE: 23
ccggcctagg ttcgccgtta cggaaaagca                              30

<210> SEQ ID NO 24
<211> LENGTH: 62
<212> TYPE: DNA
<213> ORGANISM: Artificial
<220> FEATURE:
<223> OTHER INFORMATION: 50.2_10HIS-Pme_R reverse primer

<400> SEQUENCE: 24
gtttaaacgt gatgatgatg gtggtggtgg tggtggtgtt cgccgttacg gaaaagcaga    60
ag                                                                  62

<210> SEQ ID NO 25
<211> LENGTH: 36
<212> TYPE: DNA
<213> ORGANISM: Artificial
<220> FEATURE:
<223> OTHER INFORMATION: 50.3_F forward primer

<400> SEQUENCE: 25
ccggcctagg atgtgtgatc gtattattca tctgac                       36

<210> SEQ ID NO 26
<211> LENGTH: 30
<212> TYPE: DNA
<213> ORGANISM: Artificial
<220> FEATURE:
<223> OTHER INFORMATION: 50.3_R reverse primer

<400> SEQUENCE: 26
ccggcggccg ttcgccgtta cggaaaagca                              30

<210> SEQ ID NO 27
<211> LENGTH: 62
<212> TYPE: DNA
<213> ORGANISM: Artificial
<220> FEATURE:
<223> OTHER INFORMATION: 50.3_10HIS-Pme_R reverse primer

```
<400> SEQUENCE: 27
gtttaaacgt gatgatgatg gtggtggtgg tggtggtgtt cgccgttacg gaaaagcaga      60
ag                                                                    62

<210> SEQ ID NO 28
<211> LENGTH: 31
<212> TYPE: DNA
<213> ORGANISM: Artificial
<220> FEATURE:
<223> OTHER INFORMATION: 50.4_F forward primer

<400> SEQUENCE: 28
ccggcggccg atgtgtgatc gtattattca t                                    31

<210> SEQ ID NO 29
<211> LENGTH: 62
<212> TYPE: DNA
<213> ORGANISM: Artificial
<220> FEATURE:
<223> OTHER INFORMATION: 50.4_10HIS-Pme_R reverse primer

<400> SEQUENCE: 29
gtttaaacgt gatgatgatg gtggtggtgg tggtggtgtt cgccgttacg gaaaagcaga      60
ag                                                                    62

<210> SEQ ID NO 30
<211> LENGTH: 18
<212> TYPE: DNA
<213> ORGANISM: Artificial
<220> FEATURE:
<223> OTHER INFORMATION: TA50kd_1F primer

<400> SEQUENCE: 30
gtgcggtcca cgtatgtg                                                   18

<210> SEQ ID NO 31
<211> LENGTH: 16
<212> TYPE: DNA
<213> ORGANISM: Artificial
<220> FEATURE:
<223> OTHER INFORMATION: TA50kd_2F primer

<400> SEQUENCE: 31
ggcgcgtctc gtcgac                                                     16

<210> SEQ ID NO 32
<211> LENGTH: 19
<212> TYPE: DNA
<213> ORGANISM: Artificial
<220> FEATURE:
<223> OTHER INFORMATION: TA50kd_2R primer

<400> SEQUENCE: 32
actctgccca gaagtcgac                                                  19

<210> SEQ ID NO 33
<211> LENGTH: 17
<212> TYPE: DNA
<213> ORGANISM: Artificial
<220> FEATURE:
<223> OTHER INFORMATION: TA50kd_3F primer

<400> SEQUENCE: 33
cgaaaccggt atgtgcg                                                    17
```

<210> SEQ ID NO 34
<211> LENGTH: 16
<212> TYPE: DNA
<213> ORGANISM: Artificial
<220> FEATURE:
<223> OTHER INFORMATION: TA50kd_3R primer

<400> SEQUENCE: 34
cgatcgcaca taccgg                                                    16

<210> SEQ ID NO 35
<211> LENGTH: 20
<212> TYPE: DNA
<213> ORGANISM: Artificial
<220> FEATURE:
<223> OTHER INFORMATION: T7#6 primer

<400> SEQUENCE: 35
taatacgact cactataggg                                                20

<210> SEQ ID NO 36
<211> LENGTH: 20
<212> TYPE: DNA
<213> ORGANISM: Artificial
<220> FEATURE:
<223> OTHER INFORMATION: PCRII200F#738 primer

<400> SEQUENCE: 36
cacacaggaa acagctatga                                                20

<210> SEQ ID NO 37
<211> LENGTH: 1314
<212> TYPE: DNA
<213> ORGANISM: Artificial
<220> FEATURE:
<223> OTHER INFORMATION: pTRC BH 50 kDa ORF

<400> SEQUENCE: 37

| | |
|---|---|
| atgtgtgatc gtattattca tctgactgat gactgctttg acacggacgt actccgtgcg | 60 |
| gacggggcgc gtctcgtcga tttctgggca gagtggtgcg gtccacgtat gtgtatcgcg | 120 |
| ccgattctgg atgaacgtgc agacgaatat caaggccgcc tgaccgttgc acgcctgaac | 180 |
| atcgatcaaa accctggtac tgcgccgcgc tatggcatcc gtggcatccc gactctgctg | 240 |
| ctgttccgta acggcgaagg taccatgtgt gaccgtatta tccacctgac tgacgactgc | 300 |
| ttcgacacgg atgtactccg cgcggatggg gcgcgtctcg tcgacttctg gcagagtggg | 360 |
| tgcggtcctc gtatgtgtat cgcccctatt ctggatgagc gtgctgacga atatcagggt | 420 |
| cgcctgaccg ttgcacgtct gaatatcgat caaaaccctg gcactgcacc gcgctatggc | 480 |
| atccgtggta tcccgactct cctgctgttc cgtaacggcg aagaattcat gtgtgatcgt | 540 |
| atcattcacc tgactgacga ctgttttgac acggatgttc tccgcgcgga cggggcgcgt | 600 |
| ctcgtagatt tctgggcaga gtggtgcggc cgcgtatgt gtatcgcccc gattctcgat | 660 |
| gaacgtgctg acgaatatca gggtcgcctg accgttgccc gtctgaacat cgatcaaaac | 720 |
| cctggcactg caccgcgcta tggcatccgt ggtatcccaa ctctgctgct gttccgtaac | 780 |
| ggcgaaaccg gtatgtgcga tcgcattatt cacctgactg atgactgctt tgacacggac | 840 |
| gtactccgcg cggacggggc gcgcctcgtc gatttctggg cagagtggtg cggtccgcgt | 900 |
| atgtgtatcg cgccgattct ggatgaacgt gcggacgaat atcagggccg cctgactgtt | 960 |

```
gcacgtctga acatcgacca aaaccctggc actgcgcctc gctatggcat ccgtggtatc    1020
ccgactctgc tgctcttccg taacggcgaa gccggcatgt gtgatcgtat cattcacctg    1080
actgatgact gcttcgacac ggatgtactc cgcgccgacg gggcgatcct cgtcgatttc    1140
tgggcagaat ggtgcggtcc gcgtatgtgt atcgctccga tcctggatga aatcgctgat    1200
gaatatcagg gccgcctcac cgttgcacgt ctgaatatcg atcaaaaccc tggtactgcg    1260
ccgcgctatg gtatccgtgg catcccgact cttctgcttt tccgtaacgg cgaa          1314
```

<210> SEQ ID NO 38
<211> LENGTH: 893
<212> TYPE: PRT
<213> ORGANISM: Artificial
<220> FEATURE:
<223> OTHER INFORMATION: pTRC 110 kDa expression product

<400> SEQUENCE: 38

```
Met His Gly Ser Met Cys Asp Arg Ile Ile His Leu Thr Asp Asp Cys
1               5                   10                  15

Phe Asp Thr Asp Val Leu Arg Ala Asp Gly Ala Arg Leu Val Asp Phe
            20                  25                  30

Trp Ala Glu Trp Cys Gly Pro Arg Met Cys Ile Ala Pro Ile Leu Asp
        35                  40                  45

Glu Arg Ala Asp Glu Tyr Gln Gly Arg Leu Thr Val Ala Arg Leu Asn
    50                  55                  60

Ile Asp Gln Asn Pro Gly Thr Ala Pro Arg Tyr Gly Ile Arg Gly Ile
65                  70                  75                  80

Pro Thr Leu Leu Leu Phe Arg Asn Gly Glu Thr Met Cys Asp Arg
                85                  90                  95

Ile Ile His Leu Thr Asp Asp Cys Phe Asp Thr Asp Val Leu Arg Ala
            100                 105                 110

Asp Gly Ala Arg Leu Val Asp Phe Trp Ala Glu Trp Cys Gly Pro Arg
        115                 120                 125

Met Cys Ile Ala Pro Ile Leu Asp Glu Arg Ala Asp Glu Tyr Gln Gly
    130                 135                 140

Arg Leu Thr Val Ala Arg Leu Asn Ile Asp Gln Asn Pro Gly Thr Ala
145                 150                 155                 160

Pro Arg Tyr Gly Ile Arg Gly Ile Pro Thr Leu Leu Leu Phe Arg Asn
                165                 170                 175

Gly Glu Glu Phe Met Cys Asp Arg Ile Ile His Leu Thr Asp Asp Cys
            180                 185                 190

Phe Asp Thr Asp Val Leu Arg Ala Asp Gly Ala Arg Leu Val Asp Phe
        195                 200                 205

Trp Ala Glu Trp Cys Gly Pro Arg Met Cys Ile Ala Pro Ile Leu Asp
    210                 215                 220

Glu Arg Ala Asp Glu Tyr Gln Gly Arg Leu Thr Val Ala Arg Leu Asn
225                 230                 235                 240

Ile Asp Gln Asn Pro Gly Thr Ala Pro Arg Tyr Gly Ile Arg Gly Ile
                245                 250                 255

Pro Thr Leu Leu Leu Phe Arg Asn Gly Glu Thr Gly Met Cys Asp Arg
            260                 265                 270

Ile Ile His Leu Thr Asp Asp Cys Phe Asp Thr Asp Val Leu Arg Ala
        275                 280                 285

Asp Gly Ala Arg Leu Val Asp Phe Trp Ala Glu Trp Cys Gly Pro Arg
    290                 295                 300
```

```
Met Cys Ile Ala Pro Ile Leu Asp Glu Arg Ala Asp Glu Tyr Gln Gly
305                 310                 315                 320

Arg Leu Thr Val Ala Arg Leu Asn Ile Asp Gln Asn Pro Gly Thr Ala
                325                 330                 335

Pro Arg Tyr Gly Ile Arg Gly Ile Pro Thr Leu Leu Leu Phe Arg Asn
            340                 345                 350

Gly Glu Ala Gly Met Cys Asp Arg Ile Ile His Leu Thr Asp Asp Cys
            355                 360                 365

Phe Asp Thr Asp Val Leu Arg Ala Asp Gly Ala Ile Leu Val Asp Phe
    370                 375                 380

Trp Ala Glu Trp Cys Gly Pro Arg Met Cys Ile Ala Pro Ile Leu Asp
385                 390                 395                 400

Glu Ile Ala Asp Glu Tyr Gln Gly Arg Leu Thr Val Ala Arg Leu Asn
                405                 410                 415

Ile Asp Gln Asn Pro Gly Thr Ala Pro Arg Tyr Gly Ile Arg Gly Ile
                420                 425                 430

Pro Thr Leu Leu Leu Phe Arg Asn Gly Glu Leu Glu Met Cys Asp Arg
            435                 440                 445

Ile Ile His Leu Thr Asp Asp Cys Phe Asp Thr Asp Val Leu Arg Ala
    450                 455                 460

Asp Gly Ala Arg Leu Val Asp Phe Trp Ala Glu Trp Cys Gly Pro Arg
465                 470                 475                 480

Met Cys Ile Ala Pro Ile Leu Asp Glu Arg Ala Asp Glu Tyr Gln Gly
                485                 490                 495

Arg Leu Thr Val Ala Arg Leu Asn Ile Asp Gln Asn Pro Gly Thr Ala
                500                 505                 510

Pro Arg Tyr Gly Ile Arg Gly Ile Pro Thr Leu Leu Leu Phe Arg Asn
            515                 520                 525

Gly Glu Gly Thr Met Cys Asp Arg Ile Ile His Leu Thr Asp Asp Cys
            530                 535                 540

Phe Asp Thr Asp Val Leu Arg Ala Asp Gly Ala Arg Leu Val Asp Phe
545                 550                 555                 560

Trp Ala Glu Trp Cys Gly Pro Arg Met Cys Ile Ala Pro Ile Leu Asp
                565                 570                 575

Glu Arg Ala Asp Glu Tyr Gln Gly Arg Leu Thr Val Ala Arg Leu Asn
                580                 585                 590

Ile Asp Gln Asn Pro Gly Thr Ala Pro Arg Tyr Gly Ile Arg Gly Ile
                595                 600                 605

Pro Thr Leu Leu Leu Phe Arg Asn Gly Glu Gly Phe Met Cys Asp Arg
            610                 615                 620

Ile Ile His Leu Thr Asp Asp Cys Phe Asp Thr Asp Val Leu Arg Ala
625                 630                 635                 640

Asp Gly Ala Arg Leu Val Asp Phe Trp Ala Glu Trp Cys Gly Pro Arg
                645                 650                 655

Met Cys Ile Ala Pro Ile Leu Asp Glu Arg Ala Asp Glu Tyr Gln Gly
                660                 665                 670

Arg Leu Thr Val Ala Arg Leu Asn Ile Asp Gln Asn Pro Gly Thr Ala
                675                 680                 685

Pro Arg Tyr Gly Ile Arg Gly Ile Pro Thr Leu Leu Leu Phe Arg Asn
            690                 695                 700

Gly Glu Thr Gly Met Cys Asp Arg Ile Ile His Leu Thr Asp Asp Cys
705                 710                 715                 720

Phe Asp Thr Asp Val Leu Arg Ala Asp Gly Ala Arg Leu Val Asp Phe
```

```
                725                 730                 735
Trp Ala Glu Trp Cys Gly Pro Arg Met Cys Ile Ala Pro Ile Leu Asp
            740                 745                 750
Glu Arg Ala Asp Glu Tyr Gln Gly Arg Leu Thr Val Ala Arg Leu Asn
        755                 760                 765
Ile Asp Gln Asn Pro Gly Thr Ala Pro Arg Tyr Gly Ile Arg Gly Ile
    770                 775                 780
Pro Thr Leu Leu Leu Phe Arg Asn Gly Glu Ala Gly Met Cys Asp Arg
785                 790                 795                 800
Ile Ile His Leu Thr Asp Asp Cys Phe Asp Thr Asp Val Leu Arg Ala
            805                 810                 815
Asp Gly Ala Ile Leu Val Asp Phe Trp Ala Glu Trp Cys Gly Pro Arg
        820                 825                 830
Met Cys Ile Ala Pro Ile Leu Asp Glu Ile Ala Asp Glu Tyr Gln Gly
    835                 840                 845
Arg Leu Thr Val Ala Arg Leu Asn Ile Asp Gln Asn Pro Gly Thr Ala
850                 855                 860
Pro Arg Tyr Gly Ile Arg Gly Ile Pro Thr Leu Leu Leu Phe Arg Asn
            865                 870                 875                 880
Gly Glu His His His His His His His His Val
            885                 890
```

<210> SEQ ID NO 39
<211> LENGTH: 1333
<212> TYPE: PRT
<213> ORGANISM: Artificial
<220> FEATURE:
<223> OTHER INFORMATION: pTRC 160 kDa predicted expression product

<400> SEQUENCE: 39

```
Met His Gly Ser Met Cys Asp Arg Ile Ile His Leu Thr Asp Asp Cys
1               5                   10                  15
Phe Asp Thr Asp Val Leu Arg Ala Asp Gly Ala Arg Leu Val Asp Phe
            20                  25                  30
Trp Ala Glu Trp Cys Gly Pro Arg Met Cys Ile Ala Pro Ile Leu Asp
        35                  40                  45
Glu Arg Ala Asp Glu Tyr Gln Gly Arg Leu Thr Val Ala Arg Leu Asn
    50                  55                  60
Ile Asp Gln Asn Pro Gly Thr Ala Pro Arg Tyr Gly Ile Arg Gly Ile
65                  70                  75                  80
Pro Thr Leu Leu Leu Phe Arg Asn Gly Glu Gly Thr Met Cys Asp Arg
                85                  90                  95
Ile Ile His Leu Thr Asp Asp Cys Phe Asp Thr Asp Val Leu Arg Ala
            100                 105                 110
Asp Gly Ala Arg Leu Val Asp Phe Trp Ala Glu Trp Cys Gly Pro Arg
        115                 120                 125
Met Cys Ile Ala Pro Ile Leu Asp Glu Arg Ala Asp Glu Tyr Gln Gly
    130                 135                 140
Arg Leu Thr Val Ala Arg Leu Asn Ile Asp Gln Asn Pro Gly Thr Ala
145                 150                 155                 160
Pro Arg Tyr Gly Ile Arg Gly Ile Pro Thr Leu Leu Leu Phe Arg Asn
                165                 170                 175
Gly Glu Glu Phe Met Cys Asp Arg Ile Ile His Leu Thr Asp Asp Cys
            180                 185                 190
Phe Asp Thr Asp Val Leu Arg Ala Asp Gly Ala Arg Leu Val Asp Phe
```

```
            195                 200                 205
Trp Ala Glu Trp Cys Gly Pro Arg Met Cys Ile Ala Pro Ile Leu Asp
    210                 215                 220

Glu Arg Ala Asp Glu Tyr Gln Gly Arg Leu Thr Val Ala Arg Leu Asn
225                 230                 235                 240

Ile Asp Gln Asn Pro Gly Thr Ala Pro Arg Tyr Gly Ile Arg Gly Ile
                245                 250                 255

Pro Thr Leu Leu Leu Phe Arg Asn Gly Glu Thr Gly Met Cys Asp Arg
            260                 265                 270

Ile Ile His Leu Thr Asp Asp Cys Phe Asp Thr Asp Val Leu Arg Ala
        275                 280                 285

Asp Gly Ala Arg Leu Val Asp Phe Trp Ala Glu Trp Cys Gly Pro Arg
290                 295                 300

Met Cys Ile Ala Pro Ile Leu Asp Glu Arg Ala Asp Glu Tyr Gln Gly
305                 310                 315                 320

Arg Leu Thr Val Ala Arg Leu Asn Ile Asp Gln Asn Pro Gly Thr Ala
                325                 330                 335

Pro Arg Tyr Gly Ile Arg Gly Ile Pro Thr Leu Leu Leu Phe Arg Asn
            340                 345                 350

Gly Glu Ala Gly Met Cys Asp Arg Ile Ile His Leu Thr Asp Asp Cys
        355                 360                 365

Phe Asp Thr Asp Val Leu Arg Ala Asp Gly Ala Ile Leu Val Asp Phe
370                 375                 380

Trp Ala Glu Trp Cys Gly Pro Arg Met Cys Ile Ala Pro Ile Leu Asp
385                 390                 395                 400

Glu Ile Ala Asp Glu Tyr Gln Gly Arg Leu Thr Val Ala Arg Leu Asn
                405                 410                 415

Ile Asp Gln Asn Pro Gly Thr Ala Pro Arg Tyr Gly Ile Arg Gly Ile
            420                 425                 430

Pro Thr Leu Leu Leu Phe Arg Asn Gly Glu Leu Glu Met Cys Asp Arg
        435                 440                 445

Ile Ile His Leu Thr Asp Asp Cys Phe Asp Thr Asp Val Leu Arg Ala
450                 455                 460

Asp Gly Ala Arg Leu Val Asp Phe Trp Ala Glu Trp Cys Gly Pro Arg
465                 470                 475                 480

Met Cys Ile Ala Pro Ile Leu Asp Glu Arg Ala Asp Glu Tyr Gln Gly
                485                 490                 495

Arg Leu Thr Val Ala Arg Leu Asn Ile Asp Gln Asn Pro Gly Thr Ala
            500                 505                 510

Pro Arg Tyr Gly Ile Arg Gly Ile Pro Thr Leu Leu Leu Phe Arg Asn
        515                 520                 525

Gly Glu Gly Thr Met Cys Asp Arg Ile Ile His Leu Thr Asp Asp Cys
530                 535                 540

Phe Asp Thr Asp Val Leu Arg Ala Asp Gly Ala Arg Leu Val Asp Phe
545                 550                 555                 560

Trp Ala Glu Trp Cys Gly Pro Arg Met Cys Ile Ala Pro Ile Leu Asp
                565                 570                 575

Glu Arg Ala Asp Glu Tyr Gln Gly Arg Leu Thr Val Ala Arg Leu Asn
            580                 585                 590

Ile Asp Gln Asn Pro Gly Thr Ala Pro Arg Tyr Gly Ile Arg Gly Ile
        595                 600                 605

Pro Thr Leu Leu Leu Phe Arg Asn Gly Glu Glu Phe Met Cys Asp Arg
610                 615                 620
```

-continued

```
Ile Ile His Leu Thr Asp Asp Cys Phe Asp Thr Asp Val Leu Arg Ala
625                 630                 635                 640

Asp Gly Ala Arg Leu Val Asp Phe Trp Ala Glu Trp Cys Gly Pro Arg
                645                 650                 655

Met Cys Ile Ala Pro Ile Leu Asp Glu Arg Ala Asp Glu Tyr Gln Gly
            660                 665                 670

Arg Leu Thr Val Ala Arg Leu Asn Ile Asp Gln Asn Pro Gly Thr Ala
                675                 680                 685

Pro Arg Tyr Gly Ile Arg Gly Ile Pro Thr Leu Leu Leu Phe Arg Asn
        690                 695                 700

Gly Glu Thr Gly Met Cys Asp Arg Ile Ile His Leu Thr Asp Asp Cys
705                 710                 715                 720

Phe Asp Thr Asp Val Leu Arg Ala Asp Gly Ala Arg Leu Val Asp Phe
                725                 730                 735

Trp Ala Glu Trp Cys Gly Pro Arg Met Cys Ile Ala Pro Ile Leu Asp
            740                 745                 750

Glu Arg Ala Asp Glu Tyr Gln Gly Arg Leu Thr Val Ala Arg Leu Asn
                755                 760                 765

Ile Asp Gln Asn Pro Gly Thr Ala Pro Arg Tyr Gly Ile Arg Gly Ile
        770                 775                 780

Pro Thr Leu Leu Leu Phe Arg Asn Gly Glu Ala Gly Met Cys Asp Arg
785                 790                 795                 800

Ile Ile His Leu Thr Asp Asp Cys Phe Asp Thr Asp Val Leu Arg Ala
                805                 810                 815

Asp Gly Ala Ile Leu Val Asp Phe Trp Ala Glu Trp Cys Gly Pro Arg
            820                 825                 830

Met Cys Ile Ala Pro Ile Leu Asp Glu Ile Ala Asp Glu Tyr Gln Gly
                835                 840                 845

Arg Leu Thr Val Ala Arg Leu Asn Ile Asp Gln Asn Pro Gly Thr Ala
        850                 855                 860

Pro Arg Tyr Gly Ile Arg Gly Ile Pro Thr Leu Leu Leu Phe Arg Asn
865                 870                 875                 880

Gly Glu Pro Arg Met Cys Asp Arg Ile Ile His Leu Thr Asp Asp Cys
                885                 890                 895

Phe Asp Thr Asp Val Leu Arg Ala Asp Gly Ala Arg Leu Val Asp Phe
            900                 905                 910

Trp Ala Glu Trp Cys Gly Pro Arg Met Cys Ile Ala Pro Ile Leu Asp
                915                 920                 925

Glu Arg Ala Asp Glu Tyr Gln Gly Arg Leu Thr Val Ala Arg Leu Asn
        930                 935                 940

Ile Asp Gln Asn Pro Gly Thr Ala Pro Arg Tyr Gly Ile Arg Gly Ile
945                 950                 955                 960

Pro Thr Leu Leu Leu Phe Arg Asn Gly Glu Gly Thr Met Cys Asp Arg
                965                 970                 975

Ile Ile His Leu Thr Asp Asp Cys Phe Asp Thr Asp Val Leu Arg Ala
            980                 985                 990

Asp Gly Ala Arg Leu Val Asp Phe Trp Ala Glu Trp Cys Gly Pro Arg
                995                 1000                1005

Met Cys Ile Ala Pro Ile Leu Asp Glu Arg Ala Asp Glu Tyr Gln
        1010                1015                1020

Gly Arg Leu Thr Val Ala Arg Leu Asn Ile Asp Gln Asn Pro Gly
            1025                1030                1035
```

| | | | | | | | | | | | |
|---|---|---|---|---|---|---|---|---|---|---|---|
| Thr | Ala | Pro | Arg | Tyr | Gly | Ile | Arg | Gly | Ile | Pro | Thr | Leu Leu Leu |
| | 1040 | | | | 1045 | | | | 1050 | | |

```
Thr Ala Pro Arg Tyr Gly Ile Arg Gly Ile Pro Thr Leu Leu Leu
    1040                1045                1050

Phe Arg Asn Gly Glu Glu Phe Met Cys Asp Arg Ile Ile His Leu
    1055                1060                1065

Thr Asp Asp Cys Phe Asp Thr Asp Val Leu Arg Ala Asp Gly Ala
    1070                1075                1080

Arg Leu Val Asp Phe Trp Ala Glu Trp Cys Gly Pro Arg Met Cys
    1085                1090                1095

Ile Ala Pro Ile Leu Asp Glu Arg Ala Asp Glu Tyr Gln Gly Arg
    1100                1105                1110

Leu Thr Val Ala Arg Leu Asn Ile Asp Gln Asn Pro Gly Thr Ala
    1115                1120                1125

Pro Arg Tyr Gly Ile Arg Gly Ile Pro Thr Leu Leu Leu Phe Arg
    1130                1135                1140

Asn Gly Glu Thr Gly Met Cys Asp Arg Ile Ile His Leu Thr Asp
    1145                1150                1155

Asp Cys Phe Asp Thr Asp Val Leu Arg Ala Asp Gly Ala Arg Leu
    1160                1165                1170

Val Asp Phe Trp Ala Glu Trp Cys Gly Pro Arg Met Cys Ile Ala
    1175                1180                1185

Pro Ile Leu Asp Glu Arg Ala Asp Glu Tyr Gln Gly Arg Leu Thr
    1190                1195                1200

Val Ala Arg Leu Asn Ile Asp Gln Asn Pro Gly Thr Ala Pro Arg
    1205                1210                1215

Tyr Gly Ile Arg Gly Ile Pro Thr Leu Leu Leu Phe Arg Asn Gly
    1220                1225                1230

Glu Ala Gly Met Cys Asp Arg Ile Ile His Leu Thr Asp Asp Cys
    1235                1240                1245

Phe Asp Thr Asp Val Leu Arg Ala Asp Gly Ala Ile Leu Val Asp
    1250                1255                1260

Phe Trp Ala Glu Trp Cys Gly Pro Arg Met Cys Ile Ala Pro Ile
    1265                1270                1275

Leu Asp Glu Ile Ala Asp Glu Tyr Gln Gly Arg Leu Thr Val Ala
    1280                1285                1290

Arg Leu Asn Ile Asp Gln Asn Pro Gly Thr Ala Pro Arg Tyr Gly
    1295                1300                1305

Ile Arg Gly Ile Pro Thr Leu Leu Leu Phe Arg Asn Gly Glu His
    1310                1315                1320

His His His His His His His Val
    1325                1330
```

<210> SEQ ID NO 40
<211> LENGTH: 2721
<212> TYPE: DNA
<213> ORGANISM: Artificial
<220> FEATURE:
<223> OTHER INFORMATION: truncated lac Z gene sequence

<400> SEQUENCE: 40

```
cctaggatga tagatcccgt cgttttacaa cgtcgtgact gggaaaaccc tggcgttacc      60
caacttaatc gccttgcagc acatccccct ttcgccagct ggcgtaatag cgaagaggcc     120
cgcaccgatc gcccttccca acagttgcgc agcctgaatg gcgaatggcg ctttgcctgg     180
tttccggtac cagaagcggt gccggaaagc tggctggagt gcgatcttcc tgaggccgat     240
actgtcgtcg tcccctcaaa ctggcagatg cacggttacg atgcgcccat ctacaccaac     300
```

-continued

```
gtaacctatc ccattacggt caatccgccg tttgttccca cggagaatcc gacgggttgt    360
tactcgctca catttaatgt tgatgaaagc tggctacagg aaggccagac gcgaattatt    420
tttgatggcg ttaactcggc gtttcatctg tggtgcaacg ggcgctgggt cggttacggc    480
caggacagtc gtttgccgtc tgaatttgac ctgagcgcat ttttacgcgc cggagaaaac    540
cgcctcgcgg tgatggtgct gcgttggagt gacggcagtt atctggaaga tcaggatatg    600
tggcggatga gcggcatttt ccgtgacgtc tcgttgctgc ataaaccgac tacacaaatc    660
agcgatttcc atgttgccac tcgctttaat gatgatttca gccgcgctgt actggaggct    720
gaagttcaga tgtgcggcga gttgcgtgac tacctacggg taacagtttc tttatggcag    780
ggtgaaacgc aggtcgccag cggcaccgcg cctttcggcg gtgaaattat cgatgagcgt    840
ggtggttatg ccgatcgcgt cacactacgt ctgaacgtcg aaaacccgaa actgtggagc    900
gccgaaatcc gaatctcta tcgtgcggtg gttgaactgc acaccgccga cggcacgctg    960
attgaagcag aagcctgcga tgtcggtttc gcgcgaggtg cggattgaaaa tggtctgctg   1020 ctgctgaacg gcaagccgtt gctgattcga ggcgttaacc gtcacgagca tcatcctctg   1080
catggtcagg tcatggatga gcagacgatg gtgcaggata tcctgctgat gaagcagaac   1140
aactttaacg ccgtgcgctg ttcgcattat ccgaaccatc cgctgtggta cacgctgtgc   1200
gaccgctacg gcctgtatgt ggtggatgaa gccaatattg aaaccacgg catggtgcca    1260 atgaatcgtc tgaccgatga tccgcgctgg ctaccggcga tgagcgaacg cgtaacgcga   1320
atggtgcagc gcgatcgtaa tcacccgagt gtgatcatct ggtcgctggg gaatgaatca   1380
ggccacggcg ctaatcacga cgcgctgtat cgctggatca aatctgtcga tccttcccgc   1440
ccggtgcagt atgaaggcgg cggagccgac accacggcca ccgatattat ttgcccgatg   1500
tacgcgcgcg tggatgaaga ccagcccttc ccggctgtgc cgaaatggtc catcaaaaaa   1560
tggctttcgc tacctggaga gacgcgcccg ctgatccttt gcgaatacgc ccacgcgatg   1620
ggtaacagtc ttggcggttt cgctaaatac tggcaggcgt ttcgtcagta tccccgtttta  1680 cagggcggct tcgtctggga ctgggtggat cagtcgctga ttaaatatga tgaaaacggc   1740
aacccgtggt cggcttacgg cggtgatttt ggcgatacgc cgaacgatcg ccagttctgt   1800
atgaacggtc tggtctttgc cgaccgcacg ccgcatccag cgctgacgga agcaaaacac   1860
cagcagcagt ttttccagtt ccgtttatcc gggcaaacca tcgaagtgac cagcgaatac   1920
ctgttccgtc atagcgataa cgagctcctg cactggatgg tggcgctgga tggtaagccg   1980
ctggcaagcg gtgaagtgcc tctggatgtc gctccacaag gtaaacagtt gattgaactg   2040
cctgaactac cgcagccgga gagcgccggg caactctggc tcacagtacg cgtagtgcaa   2100
ccgaacgcga ccgcatggtc agaagccggg cacatcagcg cctggcagca gtggcgtctg   2160
gcggaaaacc tcagtgtgac gctccccgcc gcgtcccacg ccatcccgca tctgaccacc   2220
agcgaaatga tttttgcat cgagctgggt aataagcgtt ggcaatttaa ccgccagtca   2280
ggctttcttt cacagatgtg gattggcgat aaaaaacaac tgctgacgcc gctgcgcgat   2340
cagttcaccc gtgcaccgct ggataacgac attggcgtaa gtgaagcgac ccgcattgac   2400
cctaacgcct gggtcgaacg ctggaaggcg gcgggccatt accaggccga agcagcgttg   2460
ttgcagtgca cggcagatac acttgctgat gcggtgctga ttacgaccgc tcacgcgtgg   2520
cagcatcagg ggaaaaacctt atttatcagc cggaaaacct accggattga tggtagtggt   2580
caaatggcga ttaccgttga tgttgaagtg gcgagcgata caccgcatcc ggcgcggatt   2640
```

-continued

```
ggcctgaact gccagctggc gcaggtagca gagcgggtaa actggctcgg attagggccg      2700
caagaaaact atcccccctag g                                               2721

<210> SEQ ID NO 41
<211> LENGTH: 2238
<212> TYPE: PRT
<213> ORGANISM: Artificial
<220> FEATURE:
<223> OTHER INFORMATION: pTRC 260 kDa expression product

<400> SEQUENCE: 41
```

| | | | | | | | | | | | | | | |
|---|---|---|---|---|---|---|---|---|---|---|---|---|---|---|
| Met | His | Gly | Ser | Met | Cys | Asp | Arg | Ile | Ile | His | Leu | Thr | Asp | Asp | Cys |
| 1 | | | | 5 | | | | | 10 | | | | | 15 | |
| Phe | Asp | Thr | Asp | Val | Leu | Arg | Ala | Asp | Gly | Ala | Arg | Leu | Val | Asp | Phe |
| | | | 20 | | | | | 25 | | | | | 30 | | |
| Trp | Ala | Glu | Trp | Cys | Gly | Pro | Arg | Met | Cys | Ile | Ala | Pro | Ile | Leu | Asp |
| | | 35 | | | | | 40 | | | | | 45 | | | |
| Glu | Arg | Ala | Asp | Glu | Tyr | Gln | Gly | Arg | Leu | Thr | Val | Ala | Arg | Leu | Asn |
| | 50 | | | | | 55 | | | | | 60 | | | | |
| Ile | Asp | Gln | Asn | Pro | Gly | Thr | Ala | Pro | Arg | Tyr | Gly | Ile | Arg | Gly | Ile |
| 65 | | | | | 70 | | | | | 75 | | | | | 80 |
| Pro | Thr | Leu | Leu | Leu | Phe | Arg | Asn | Gly | Glu | Gly | Thr | Met | Cys | Asp | Arg |
| | | | | 85 | | | | | 90 | | | | | 95 | |
| Ile | Ile | His | Leu | Thr | Asp | Asp | Cys | Phe | Asp | Thr | Asp | Val | Leu | Arg | Ala |
| | | | 100 | | | | | 105 | | | | | 110 | | |
| Asp | Gly | Ala | Arg | Leu | Val | Asp | Phe | Trp | Ala | Glu | Trp | Cys | Gly | Pro | Arg |
| | | 115 | | | | | 120 | | | | | 125 | | | |
| Met | Cys | Ile | Ala | Pro | Ile | Leu | Asp | Glu | Arg | Ala | Asp | Glu | Tyr | Gln | Gly |
| | 130 | | | | | 135 | | | | | 140 | | | | |
| Arg | Leu | Thr | Val | Ala | Arg | Leu | Asn | Ile | Asp | Gln | Asn | Pro | Gly | Thr | Ala |
| 145 | | | | | 150 | | | | | 155 | | | | | 160 |
| Pro | Arg | Tyr | Gly | Ile | Arg | Gly | Ile | Pro | Thr | Leu | Leu | Leu | Phe | Arg | Asn |
| | | | | 165 | | | | | 170 | | | | | 175 | |
| Gly | Glu | Glu | Phe | Met | Cys | Asp | Arg | Ile | Ile | His | Leu | Thr | Asp | Asp | Cys |
| | | | 180 | | | | | 185 | | | | | 190 | | |
| Phe | Asp | Thr | Asp | Val | Leu | Arg | Ala | Asp | Gly | Ala | Arg | Leu | Val | Asp | Phe |
| | | 195 | | | | | 200 | | | | | 205 | | | |
| Trp | Ala | Glu | Trp | Cys | Gly | Pro | Arg | Met | Cys | Ile | Ala | Pro | Ile | Leu | Asp |
| | 210 | | | | | 215 | | | | | 220 | | | | |
| Glu | Arg | Ala | Asp | Glu | Tyr | Gln | Gly | Arg | Leu | Thr | Val | Ala | Arg | Leu | Asn |
| 225 | | | | | 230 | | | | | 235 | | | | | 240 |
| Ile | Asp | Gln | Asn | Pro | Gly | Thr | Ala | Pro | Arg | Tyr | Gly | Ile | Arg | Gly | Ile |
| | | | | 245 | | | | | 250 | | | | | 255 | |
| Pro | Thr | Leu | Leu | Leu | Phe | Arg | Asn | Gly | Glu | Thr | Gly | Met | Cys | Asp | Arg |
| | | | 260 | | | | | 265 | | | | | 270 | | |
| Ile | Ile | His | Leu | Thr | Asp | Asp | Cys | Phe | Asp | Thr | Asp | Val | Leu | Arg | Ala |
| | | 275 | | | | | 280 | | | | | 285 | | | |
| Asp | Gly | Ala | Arg | Leu | Val | Asp | Phe | Trp | Ala | Glu | Trp | Cys | Gly | Pro | Arg |
| | 290 | | | | | 295 | | | | | 300 | | | | |
| Met | Cys | Ile | Ala | Pro | Ile | Leu | Asp | Glu | Arg | Ala | Asp | Glu | Tyr | Gln | Gly |
| 305 | | | | | 310 | | | | | 315 | | | | | 320 |
| Arg | Leu | Thr | Val | Ala | Arg | Leu | Asn | Ile | Asp | Gln | Asn | Pro | Gly | Thr | Ala |
| | | | | 325 | | | | | 330 | | | | | 335 | |
| Pro | Arg | Tyr | Gly | Ile | Arg | Gly | Ile | Pro | Thr | Leu | Leu | Leu | Phe | Arg | Asn |
| | | | 340 | | | | | 345 | | | | | 350 | | |

-continued

```
Gly Glu Ala Gly Met Cys Asp Arg Ile Ile His Leu Thr Asp Asp Cys
            355                 360                 365

Phe Asp Thr Asp Val Leu Arg Ala Asp Gly Ala Ile Leu Val Asp Phe
    370                 375                 380

Trp Ala Glu Trp Cys Gly Pro Arg Met Cys Ile Ala Pro Ile Leu Asp
385                 390                 395                 400

Glu Ile Ala Asp Glu Tyr Gln Gly Arg Leu Thr Val Ala Arg Leu Asn
                405                 410                 415

Ile Asp Gln Asn Pro Gly Thr Ala Pro Arg Tyr Gly Ile Arg Gly Ile
            420                 425                 430

Pro Thr Leu Leu Leu Phe Arg Asn Gly Glu Leu Glu Met Cys Asp Arg
            435                 440                 445

Ile Ile His Leu Thr Asp Asp Cys Phe Asp Thr Asp Val Leu Arg Ala
450                 455                 460

Asp Gly Ala Arg Leu Val Asp Phe Trp Ala Glu Trp Cys Gly Pro Arg
465                 470                 475                 480

Met Cys Ile Ala Pro Ile Leu Asp Glu Arg Ala Asp Glu Tyr Gln Gly
                485                 490                 495

Arg Leu Thr Val Ala Arg Leu Asn Ile Asp Gln Asn Pro Gly Thr Ala
            500                 505                 510

Pro Arg Tyr Gly Ile Arg Gly Ile Pro Thr Leu Leu Leu Phe Arg Asn
            515                 520                 525

Gly Glu Gly Thr Met Cys Asp Arg Ile Ile His Leu Thr Asp Asp Cys
            530                 535                 540

Phe Asp Thr Asp Val Leu Arg Ala Asp Gly Ala Arg Leu Val Asp Phe
545                 550                 555                 560

Trp Ala Glu Trp Cys Gly Pro Arg Met Cys Ile Ala Pro Ile Leu Asp
                565                 570                 575

Glu Arg Ala Asp Glu Tyr Gln Gly Arg Leu Thr Val Ala Arg Leu Asn
            580                 585                 590

Ile Asp Gln Asn Pro Gly Thr Ala Pro Arg Tyr Gly Ile Arg Gly Ile
            595                 600                 605

Pro Thr Leu Leu Leu Phe Arg Asn Gly Glu Glu Phe Met Cys Asp Arg
            610                 615                 620

Ile Ile His Leu Thr Asp Asp Cys Phe Asp Thr Asp Val Leu Arg Ala
625                 630                 635                 640

Asp Gly Ala Arg Leu Val Asp Phe Trp Ala Glu Trp Cys Gly Pro Arg
                645                 650                 655

Met Cys Ile Ala Pro Ile Leu Asp Glu Arg Ala Asp Glu Tyr Gln Gly
                660                 665                 670

Arg Leu Thr Val Ala Arg Leu Asn Ile Asp Gln Asn Pro Gly Thr Ala
            675                 680                 685

Pro Arg Tyr Gly Ile Arg Gly Ile Pro Thr Leu Leu Leu Phe Arg Asn
            690                 695                 700

Gly Glu Thr Gly Met Cys Asp Arg Ile Ile His Leu Thr Asp Asp Cys
705                 710                 715                 720

Phe Asp Thr Asp Val Leu Arg Ala Asp Gly Ala Arg Leu Val Asp Phe
                725                 730                 735

Trp Ala Glu Trp Cys Gly Pro Arg Met Cys Ile Ala Pro Ile Leu Asp
            740                 745                 750

Glu Arg Ala Asp Glu Tyr Gln Gly Arg Leu Thr Val Ala Arg Leu Asn
            755                 760                 765
```

```
Ile Asp Gln Asn Pro Gly Thr Ala Pro Arg Tyr Gly Ile Arg Gly Ile
770                 775                 780

Pro Thr Leu Leu Leu Phe Arg Asn Gly Glu Ala Gly Met Cys Asp Arg
785                 790                 795                 800

Ile Ile His Leu Thr Asp Asp Cys Phe Asp Thr Asp Val Leu Arg Ala
            805                 810                 815

Asp Gly Ala Ile Leu Val Asp Phe Trp Ala Glu Trp Cys Gly Pro Arg
                820                 825                 830

Met Cys Ile Ala Pro Ile Leu Asp Glu Ile Ala Asp Tyr Gln Gly
            835                 840                 845

Arg Leu Thr Val Ala Arg Leu Asn Ile Asp Gln Asn Pro Gly Thr Ala
850                 855                 860

Pro Arg Tyr Gly Ile Arg Gly Ile Pro Thr Leu Leu Leu Phe Arg Asn
865                 870                 875                 880

Gly Glu Pro Arg Met Ile Asp Pro Val Val Leu Gln Arg Arg Asp Trp
                885                 890                 895

Glu Asn Pro Gly Val Thr Gln Leu Asn Arg Leu Ala Ala His Pro Pro
                900                 905                 910

Phe Ala Ser Trp Arg Asn Ser Glu Glu Ala Arg Thr Asp Arg Pro Ser
            915                 920                 925

Gln Gln Leu Arg Ser Leu Asn Gly Glu Trp Arg Phe Ala Trp Phe Pro
930                 935                 940

Val Pro Glu Ala Val Pro Glu Ser Trp Leu Glu Cys Asp Leu Pro Glu
945                 950                 955                 960

Ala Asp Thr Val Val Val Pro Ser Asn Trp Gln Met His Gly Tyr Asp
                965                 970                 975

Ala Pro Ile Tyr Thr Asn Val Thr Tyr Pro Ile Thr Val Asn Pro Pro
            980                 985                 990

Phe Val Pro Thr Glu Asn Pro Thr Gly Cys Tyr Ser Leu Thr Phe Asn
                995                 1000                1005

Val Asp Glu Ser Trp Leu Gln Glu Gly Gln Thr Arg Ile Ile Phe
    1010                1015                1020

Asp Gly Val Asn Ser Ala Phe His Leu Trp Cys Asn Gly Arg Trp
    1025                1030                1035

Val Gly Tyr Gly Gln Asp Ser Arg Leu Pro Ser Glu Phe Asp Leu
    1040                1045                1050

Ser Ala Phe Leu Arg Ala Gly Glu Asn Arg Leu Ala Val Met Val
    1055                1060                1065

Leu Arg Trp Ser Asp Gly Ser Tyr Leu Glu Asp Gln Asp Met Trp
    1070                1075                1080

Arg Met Ser Gly Ile Phe Arg Asp Val Ser Leu Leu His Lys Pro
    1085                1090                1095

Thr Thr Gln Ile Ser Asp Phe His Val Ala Thr Arg Phe Asn Asp
    1100                1105                1110

Asp Phe Ser Arg Ala Val Leu Glu Ala Glu Val Gln Met Cys Gly
    1115                1120                1125

Glu Leu Arg Asp Tyr Leu Arg Val Thr Val Ser Leu Trp Gln Gly
    1130                1135                1140

Glu Thr Gln Val Ala Ser Gly Thr Ala Pro Phe Gly Gly Glu Ile
    1145                1150                1155

Ile Asp Glu Arg Gly Gly Tyr Ala Asp Arg Val Thr Leu Arg Leu
    1160                1165                1170

Asn Val Glu Asn Pro Lys Leu Trp Ser Ala Glu Ile Pro Asn Leu
```

```
             1175                1180                1185

Tyr Arg Ala Val Val Glu Leu His Thr Ala Asp Gly Thr Leu Ile
        1190                1195                1200

Glu Ala Glu Ala Cys Asp Val Gly Phe Arg Glu Val Arg Ile Glu
        1205                1210                1215

Asn Gly Leu Leu Leu Leu Asn Gly Lys Pro Leu Leu Ile Arg Gly
        1220                1225                1230

Val Asn Arg His Glu His His Pro Leu His Gly Gln Val Met Asp
        1235                1240                1245

Glu Gln Thr Met Val Gln Asp Ile Leu Leu Met Lys Gln Asn Asn
        1250                1255                1260

Phe Asn Ala Val Arg Cys Ser His Tyr Pro Asn His Pro Leu Trp
        1265                1270                1275

Tyr Thr Leu Cys Asp Arg Tyr Gly Leu Tyr Val Val Asp Glu Ala
        1280                1285                1290

Asn Ile Glu Thr His Gly Met Val Pro Met Asn Arg Leu Thr Asp
        1295                1300                1305

Asp Pro Arg Trp Leu Pro Ala Met Ser Glu Arg Val Thr Arg Met
        1310                1315                1320

Val Gln Arg Asp Arg Asn His Pro Ser Val Ile Ile Trp Ser Leu
        1325                1330                1335

Gly Asn Glu Ser Gly His Gly Ala Asn His Asp Ala Leu Tyr Arg
        1340                1345                1350

Trp Ile Lys Ser Val Asp Pro Ser Arg Pro Val Gln Tyr Glu Gly
        1355                1360                1365

Gly Gly Ala Asp Thr Thr Ala Thr Asp Ile Ile Cys Pro Met Tyr
        1370                1375                1380

Ala Arg Val Asp Glu Asp Gln Pro Phe Pro Ala Val Pro Lys Trp
        1385                1390                1395

Ser Ile Lys Lys Trp Leu Ser Leu Pro Gly Glu Thr Arg Pro Leu
        1400                1405                1410

Ile Leu Cys Glu Tyr Ala His Ala Met Gly Asn Ser Leu Gly Gly
        1415                1420                1425

Phe Ala Lys Tyr Trp Gln Ala Phe Arg Gln Tyr Pro Arg Leu Gln
        1430                1435                1440

Gly Gly Phe Val Trp Asp Trp Val Asp Gln Ser Leu Ile Lys Tyr
        1445                1450                1455

Asp Glu Asn Gly Asn Pro Trp Ser Ala Tyr Gly Gly Asp Phe Gly
        1460                1465                1470

Asp Thr Pro Asn Asp Arg Gln Phe Cys Met Asn Gly Leu Val Phe
        1475                1480                1485

Ala Asp Arg Thr Pro His Pro Ala Leu Thr Glu Ala Lys His Gln
        1490                1495                1500

Gln Gln Phe Phe Gln Phe Arg Leu Ser Gly Gln Thr Ile Glu Val
        1505                1510                1515

Thr Ser Glu Tyr Leu Phe Arg His Ser Asp Asn Glu Leu Leu His
        1520                1525                1530

Trp Met Val Ala Leu Asp Gly Lys Pro Leu Ala Ser Gly Glu Val
        1535                1540                1545

Pro Leu Asp Val Ala Pro Gln Gly Lys Gln Leu Ile Glu Leu Pro
        1550                1555                1560

Glu Leu Pro Gln Pro Glu Ser Ala Gly Gln Leu Trp Leu Thr Val
        1565                1570                1575
```

-continued

```
Arg Val Val Gln Pro Asn Ala Thr Ala Trp Ser Glu Ala Gly His
    1580            1585                1590

Ile Ser Ala Trp Gln Gln Trp Arg Leu Ala Glu Asn Leu Ser Val
    1595            1600                1605

Thr Leu Pro Ala Ala Ser His Ala Ile Pro His Leu Thr Thr Ser
    1610            1615                1620

Glu Met Asp Phe Cys Ile Glu Leu Gly Asn Lys Arg Trp Gln Phe
    1625            1630                1635

Asn Arg Gln Ser Gly Phe Leu Ser Gln Met Trp Ile Gly Asp Lys
    1640            1645                1650

Lys Gln Leu Leu Thr Pro Leu Arg Asp Gln Phe Thr Arg Ala Pro
    1655            1660                1665

Leu Asp Asn Asp Ile Gly Val Ser Glu Ala Thr Arg Ile Asp Pro
    1670            1675                1680

Asn Ala Trp Val Glu Arg Trp Lys Ala Ala Gly His Tyr Gln Ala
    1685            1690                1695

Glu Ala Ala Leu Leu Gln Cys Thr Ala Asp Thr Leu Ala Asp Ala
    1700            1705                1710

Val Leu Ile Thr Thr Ala His Ala Trp Gln His Gln Gly Lys Thr
    1715            1720                1725

Leu Phe Ile Ser Arg Lys Thr Tyr Arg Ile Asp Gly Ser Gly Gln
    1730            1735                1740

Met Ala Ile Thr Val Asp Val Glu Val Ala Ser Asp Thr Pro His
    1745            1750                1755

Pro Ala Arg Ile Gly Leu Asn Cys Gln Leu Ala Gln Val Ala Glu
    1760            1765                1770

Arg Val Asn Trp Leu Gly Leu Gly Pro Gln Glu Asn Tyr Pro Pro
    1775            1780                1785

Arg Met Cys Asp Arg Ile Ile His Leu Thr Asp Asp Cys Phe Asp
    1790            1795                1800

Thr Asp Val Leu Arg Ala Asp Gly Ala Arg Leu Val Asp Phe Trp
    1805            1810                1815

Ala Glu Trp Cys Gly Pro Arg Met Cys Ile Ala Pro Ile Leu Asp
    1820            1825                1830

Glu Arg Ala Asp Glu Tyr Gln Gly Arg Leu Thr Val Ala Arg Leu
    1835            1840                1845

Asn Ile Asp Gln Asn Pro Gly Thr Ala Pro Arg Tyr Gly Ile Arg
    1850            1855                1860

Gly Ile Pro Thr Leu Leu Leu Phe Arg Asn Gly Glu Gly Thr Met
    1865            1870                1875

Cys Asp Arg Ile Ile His Leu Thr Asp Asp Cys Phe Asp Thr Asp
    1880            1885                1890

Val Leu Arg Ala Asp Gly Ala Arg Leu Val Asp Phe Trp Ala Glu
    1895            1900                1905

Trp Cys Gly Pro Arg Met Cys Ile Ala Pro Ile Leu Asp Glu Arg
    1910            1915                1920

Ala Asp Glu Tyr Gln Gly Arg Leu Thr Val Ala Arg Leu Asn Ile
    1925            1930                1935

Asp Gln Asn Pro Gly Thr Ala Pro Arg Tyr Gly Ile Arg Gly Ile
    1940            1945                1950

Pro Thr Leu Leu Leu Phe Arg Asn Gly Glu Glu Phe Met Cys Asp
    1955            1960                1965
```

-continued

```
Arg Ile Ile His Leu Thr Asp Asp Cys Phe Asp Thr Asp Val Leu
    1970            1975                1980

Arg Ala Asp Gly Ala Arg Leu Val Asp Phe Trp Ala Glu Trp Cys
    1985            1990                1995

Gly Pro Arg Met Cys Ile Ala Pro Ile Leu Asp Glu Arg Ala Asp
    2000            2005                2010

Glu Tyr Gln Gly Arg Leu Thr Val Ala Arg Leu Asn Ile Asp Gln
    2015            2020                2025

Asn Pro Gly Thr Ala Pro Arg Tyr Gly Ile Arg Gly Ile Pro Thr
    2030            2035                2040

Leu Leu Leu Phe Arg Asn Gly Glu Thr Gly Met Cys Asp Arg Ile
    2045            2050                2055

Ile His Leu Thr Asp Asp Cys Phe Asp Thr Asp Val Leu Arg Ala
    2060            2065                2070

Asp Gly Ala Arg Leu Val Asp Phe Trp Ala Glu Trp Cys Gly Pro
    2075            2080                2085

Arg Met Cys Ile Ala Pro Ile Leu Asp Glu Arg Ala Asp Glu Tyr
    2090            2095                2100

Gln Gly Arg Leu Thr Val Ala Arg Leu Asn Ile Asp Gln Asn Pro
    2105            2110                2115

Gly Thr Ala Pro Arg Tyr Gly Ile Arg Gly Ile Pro Thr Leu Leu
    2120            2125                2130

Leu Phe Arg Asn Gly Glu Ala Gly Met Cys Asp Arg Ile Ile His
    2135            2140                2145

Leu Thr Asp Asp Cys Phe Asp Thr Asp Val Leu Arg Ala Asp Gly
    2150            2155                2160

Ala Ile Leu Val Asp Phe Trp Ala Glu Trp Cys Gly Pro Arg Met
    2165            2170                2175

Cys Ile Ala Pro Ile Leu Asp Glu Ile Ala Asp Glu Tyr Gln Gly
    2180            2185                2190

Arg Leu Thr Val Ala Arg Leu Asn Ile Asp Gln Asn Pro Gly Thr
    2195            2200                2205

Ala Pro Arg Tyr Gly Ile Arg Gly Ile Pro Thr Leu Leu Leu Phe
    2210            2215                2220

Arg Asn Gly Glu His His His His His His His His His His Val
    2225            2230                2235
```

SHARPLY RESOLVING LABELED PROTEIN MOLECULAR WEIGHT STANDARDS

CROSS-REFERENCE TO RELATED APPLICATIONS

This application is a continuation of U.S. application Ser. No. 12/263,672 filed Nov. 3, 2008, which is a continuation of U.S. application Ser. No. 11/781,251 filed Jul. 21, 2007 (now abandoned), and claims priority to U.S. application Ser. No. 60/820,101 filed Jul. 21, 2006, and U.S. application Ser. No. 60/870,252 filed Dec. 15, 2006, which disclosures are herein incorporated by reference in their entirety.

REFERENCE TO A SEQUENCE LISTING

This application incorporates by reference a Sequence Listing submitted with this application as text file IVGN 563_WorkFile.txt created on Jul. 21, 2007 and having a size of 87.3 kilobytes.

BACKGROUND OF THE INVENTION

Field of the Invention

The invention relates generally to labeled protein standards for use in biochemical separations and more specifically to labeled protein standards for used in gel electrophoresis.

Background Information

Tools that aid in the development of new drugs and new medical diagnostics, as well as certain diagnostics themselves, require accurate and efficient analysis of protein samples. This in turn requires markers that accurately allow the identification of the size of proteins in a protein sample that is separated using separation methods. Separation methods that are commonly performed in biochemistry for the purification, identification, and characterization of proteins include chromatography, gel electrophoresis, and solution electrophoresis. These methods typically use standards for molecular weight or charge determination. Gel electrophoresis in particular is a common tool for the development of new drugs and medical diagnostics that is typically performed with molecular weight markers.

Pre-labeled protein standards for electrophoresis are notoriously less sharply resolving than unlabeled standards, and often the molecular weights of the labeled markers are inexact, differing from the unlabeled proteins by varying amounts. The bands of a pre-stained protein marker run in a denaturing polyacrylamide gel can be, for example, significantly wider and more diffuse than a band that results from the same protein that has not been pre-labeled, but instead is stained after electrophoresis is complete. This is largely due to the difficulties in uniformly labeling a particular protein standard.

Labeling of proteins is typically performed by attaching a label to a chemical group of one or more amino acid residues of the protein. The significant reactive groups of amino acids behave as nucleophiles in chemical reactions, for example, the sulfhydryl group of cysteine; the amino group of an N-terminal amino acid or of lysine, histidine, tryptophan, or arginine; the carboxyl group of aspartate and glutamate or a C-terminal amino acid; the phenolate of tyrosine; and the thioether of methionine. The selection of a particular reactive chemical group on the dye to be conjugated to a protein and manipulation of reaction conditions at which a chemical conjugation is performed (such as, for example, pH) will typically favor conjugation of a dye to one or more particular amino acids.

Although reaction conditions can be adjusted to reduce side reactions with one or more amino acids that are not targeted for labeling, side reactions are difficult to completely eliminate or control. The addition of label to a variable number of sites of a particular protein through side reactions reduces the uniformity in the amount of label attached to the protein, such that a given labeled protein standard comprises a population of labeled protein molecules in which different members of the population have different migration characteristics. Pre-labeled standards therefore typically do not resolve as well as unlabeled proteins in separations, producing bands on electrophoresis gels, for example, that are much less sharp than the bands produced by the same proteins electrophoresed in unlabeled form. The variability of labeling of pre-labeled standards often makes molecular weight determination using pre-labeled standards unreliable.

Another factor contributing to poor resolution of pre-labeled proteins on electrophoresis gels is protein-to-protein variability in the ratio of the number of attached dye molecules to molecular weight. Because a protein standard set uses different marker proteins to represent different molecular weights, and the different proteins of the set have variable ratios of the number of target amino acid residues to molecular weight, it is often necessary to mix different amounts of individual labeled protein standards to provide a pre-labeled marker set having proteins with similar intensity for visualization of the marker proteins. In many cases, this requires that one or more labeled proteins will be "overloaded" in a gel lane with respect to protein amount to achieve a desirable intensity for the resulting band on an electrophoresis gel. The overloading of proteins of the standard set leads to bands on the gel that are broad and not sharply delineated, making it difficult to assess the migration distance of the protein of a particular molecular weight.

SUMMARY OF THE INVENTION

Provided herein are labeled protein standards useful in electrophoresis or chromatography that have consistent separation characteristics that are substantially the same as the separation characteristics of their unlabeled counterparts. The invention provides pre-labeled protein standard sets that include a plurality of labeled proteins, in which one or more of the labeled proteins is selectively labeled on a first amino acid. A protein that is selectively labeled with a labeling compound on a first, or target, amino acid has a labeling compound conjugated to the first amino acid and is either: depleted in residues of a second, or non-target, amino acid that can react with the labeling compound; or: includes an amino acid sequence having homology to a naturally-occurring protein, in which the sequence has fewer residues of a second amino acid that is capable of reacting with the labeling compound than the wild-type protein sequence from which it is derived.

By reducing the number of residues of amino acids that can bind a labeling compound in side reactions, variability in the amount of labeling compound attached to a given protein molecule is reduced. The reduction in multiple species of a labeled protein that would otherwise result from this labeling variability provides for more precise separation characteristics. The present invention provides pre-labeled protein standard sets that when electrophoresed give sharp bands that have migration distances consistent with the migration distances of the proteins of the standard set electrophoresed in unlabeled form.

In certain embodiments, a labeling compound conjugated to a first amino acid is a dye. The dye can comprise a chromophore or fluorophore. Reducing or eliminating the attachment of a dye to residues of one or more amino acids not targeted for labeling decreases variability in the amount and position of dye attached to a marker protein. The specificity of labeling achieved using the methods provided in the invention produces labeled proteins that are highly-resolving in separation procedures, such as electrophoresis on denaturing gels.

In one aspect, the invention provides a pre-labeled protein standard set comprising a plurality of labeled proteins, in which one or more of the proteins of the plurality is selectively labeled, in which a selectively labeled protein comprises a labeling compound on a first, or target, amino acid, and has less than one residue of a second amino acid that reacts with the labeling compound per ten kilodaltons (kDa) of protein. In some embodiments, a selectively labeled protein of the invention lacks residues of a second amino acid that can react with a labeling compound.

In some embodiments of this aspect of the invention, a selectively labeled protein includes an amino acid sequence having homology to an amino acid sequence of a naturally-occurring protein, in which the naturally-occurring protein is naturally depleted in or deficient in a non-target amino acid. In some illustrative embodiments of pre-labeled protein standard sets, one or more selectively labeled protein standards of the set comprises a naturally-occurring protein, or a fragment thereof, that is labeled on a first (target) amino acid and that lacks a second (non-target) amino acid. In some illustrative embodiments, a selectively labeled protein standard of a pre-labeled protein standard set is labeled on a first amino acid, and comprises one or more copies of an amino acid sequence of a naturally-occurring protein, or a portion thereof, that lacks a second amino acid.

In embodiments in which a pre-labeled protein standard comprises an amino acid sequence having homology to an amino acid sequence of a naturally-occurring protein, in which the sequence is depleted in or deficient in a non-target amino acid, a selectively labeled protein of a pre-labeled protein standard set can have one, two, three, four, five, six, seven, eight, nine, ten, eleven, twelve, thirteen, fourteen, fifteen, sixteen, seventeen, eighteen, nineteen, twenty, or more than twenty copies of an amino acid sequence homologous to an amino acid sequence of a naturally-occurring protein.

In some preferred embodiments, a pre-labeled protein standard set can include two or more selectively labeled proteins, in which the two or more selectively labeled proteins comprise different numbers of copies of an amino acid sequence having homology to an amino acid sequence of a naturally-occurring protein that is depleted in or deficient in a non-target amino acid.

In certain embodiments, a selectively labeled protein comprises one or more copies of an amino acid sequence that is not homologous to a sequence of a naturally-occurring protein, in which the amino acid sequence is depleted in or deficient in a non-target amino acid. For example, in some embodiments of pre-labeled protein standard sets, one or more selectively labeled protein standards of the set comprises one or more copies of an amino acid sequence that is not known to have homology to a naturally-occurring protein and the one or more selectively labeled proteins is labeled on a first, or target, amino acid and is depleted in a second (non-target) amino acid. In some illustrative embodiments, a selectively labeled protein standard of a pre-labeled protein standard set comprises one or more copies of an amino acid sequence not known to occur in a naturally-occurring protein, that lacks a non-target amino acid. For example, a protein not related to a known naturally-occurring protein can be designed to be depleted in, preferably deficient in, a non-target amino acid and synthesized recombinantly or by chemical peptide synthesis.

In embodiments in which a pre-labeled protein standard comprises an amino acid sequence not derived from a naturally-occurring protein, in which the sequence is depleted in or deficient in a non-target amino acid, a selectively labeled protein of a pre-labeled protein standard set can have one, two, three, four, five, six, seven, eight, nine, ten, eleven, twelve, thirteen, fourteen, fifteen, sixteen, seventeen, eighteen, nineteen, twenty, or more copies of an amino acid sequence not derived from the naturally-occurring protein.

In some preferred embodiments of the invention, a pre-labeled protein standard set can include two or more selectively labeled proteins, in which each of the two or more selectively labeled proteins comprise different numbers of copies of a sequence not homologous to a naturally-occurring protein in which the sequence is depleted in or deficient in a non-target amino acid.

In another aspect of the invention, the invention provides a pre-labeled protein standard set comprising a plurality of labeled proteins, in which one or more of the proteins of the plurality is selectively labeled, in which a selectively labeled protein comprises a labeling compound on a first amino acid, and the selectively labeled protein includes an amino acid sequence having homology to an amino acid sequence of a naturally-occurring protein, in which the sequence has a reduced number of residues of a second amino acid that reacts with a labeling compound when compared with the wild type amino acid sequence of the naturally-occurring protein. In some illustrative embodiments of these aspects of the invention, a selectively labeled protein standard is a protein that is labeled on a target amino acid and comprises one or more copies of an amino acid sequence that is homologous to a sequence of a naturally-occurring protein, in which the sequence having homology to an amino acid sequence of a naturally-occurring protein sequence lacks a non-target amino acid. The invention thus includes sets of pre-labeled protein standards that comprise a plurality of labeled proteins, in which one or more of the labeled proteins is a selectively labeled protein that comprises one or more copies of an amino acid sequence that is at least 60%, at least 70%, at least 80% or at least 90% homologous to at least 20, 30, 40, 50 or more contiguous amino acids of a naturally-occurring protein, in which the homologous sequence lacks residues of a second amino acid capable of reacting with the labeling compound, and comprises a labeling compound conjugated to a first amino acid.

In some preferred embodiments of the invention, a pre-labeled protein standard set can include two or more selectively labeled proteins, in which the two or more selectively labeled proteins each comprise a different number of copies of an amino acid sequence having homology to an amino acid sequence of a naturally-occurring protein. In some preferred embodiments of the invention, a pre-labeled protein standard set can include two or more selectively labeled proteins, in which the two or more proteins each comprise a different number of copies of an amino acid sequence homologous to an amino acid sequence of a nucleotide-disulfide reductase. In some illustrative examples, selectively labeled proteins of a pre-labeled protein standard include different numbers of copies of an amino acid sequence homologous to at least a portion of a thioredoxin.

In embodiments in which a pre-labeled protein standard comprises a sequence derived from a naturally-occurring protein, in which the sequence has a reduced number of residues of a nnontarget amino acid relative to the naturally-occurring protein sequence, a selectively labeled protein of a pre-labeled protein standard set can have one, two, three, four, five, six, seven, eight, nine, ten, eleven, twelve, thirteen, fourteen, fifteen, sixteen, seventeen, eighteen, nineteen, twenty, or more copies of an amino acid sequence derived from a naturally-occurring protein. A set of pre-labeled protein standards can comprise two or more labeled proteins, in which the two or more proteins comprise different numbers of copies of a sequence derived from a naturally-occurring protein, in which the number of residues of a non-target amino acid have been reduced relative to the naturally-occurring protein sequence.

One aspect of the invention is a protein selectively labeled on lysine. The invention includes protein standard sets that comprise one or more proteins selectively labeled on lysine and depleted in cysteine. In some embodiments, a protein selectively labeled on lysine lacks cysteine residues. The invention includes pre-labeled protein standard sets that comprise a plurality of labeled proteins, in which one or more of the labeled proteins is depleted in cysteine residues and comprises a labeling compound conjugated to one or more lysine residues. The protein(s) selectively labeled on lysine can comprise an amino acid sequence that is not homologous to a known amino acid sequence of a naturally-occurring protein, or can be an amino acid sequence that has homology to the sequence of a naturally-occurring protein In some embodiments, a protein standard selectively labeled on lysine comprises one or more copies of an amino acid sequence having homology to the amino acid sequence of a naturally-occurring protein, in which the amino acid sequence homologous to the sequence of a naturally-occurring protein has a reduced number of cysteine residues relative to the sequence of the naturally-occurring protein. The invention includes a set of pre-labeled protein standards that comprise a plurality of labeled proteins, in which one or more of the labeled proteins comprises one or more copies of an amino acid sequence homologous to an amino acid sequence of a naturally-occurring protein, in which the homologous amino acid sequence has a reduced number of cysteine residues relative to the sequence of the naturally-occurring protein.

In one embodiment, a protein selectively labeled on lysine comprises two or more copies of an amino acid sequence having 60%, 70%, 80% or greater homology to at least 20, 30, 40, or 50 amino acids of a naturally-occurring protein sequence in which the homologous amino acid sequence of the selectively labeled protein lacks cysteine. In one embodiment, a lysine-labeled protein comprises two or more copies of an amino acid sequence derived from a naturally-occurring protein sequence, in which all of the cysteine residues of the naturally-occurring protein sequence have been removed or changed to an amino acid other than cysteine. The invention also includes nucleic acid constructs that encode proteins that comprise two or more copies of an amino acid sequence derived from the sequence of a naturally-occurring protein, in which all of the cysteine codons have been deleted or changed to non-cysteine codons.

One aspect of the invention is a protein labeled on cysteine. The invention includes protein standard sets that comprise one or more proteins selectively labeled on cysteine and depleted in lysine. In some embodiments, a protein selectively labeled on cysteine lacks lysine residues. The invention includes pre-labeled protein standard sets that comprise a plurality of labeled proteins, in which one or more of the labeled proteins is depleted in lysine residues and comprises a labeling compound conjugated to one or more cysteine residues. The protein(s) selectively labeled on cysteine can comprise an amino acid sequence that is not homologous to a known amino acid sequence of a naturally-occurring protein, or can be an amino acid sequence that has homology to the sequence of a naturally-occurring protein.

In some embodiments, a protein standard selectively labeled on cysteine comprises one or more copies of an amino acid sequence having homology to an amino acid sequence of a naturally-occurring protein, in which the amino acid sequence homologous to a sequence of a naturally-occurring protein has a reduced number of lysine residues relative to the sequence of the naturally-occurring protein. The invention includes a set of pre-labeled protein standards that comprise a plurality of labeled proteins, in which one or more of the labeled proteins comprises one or more copies of an amino acid sequence homologous to an amino acid sequence of a naturally-occurring protein, in which the homologous amino acid sequence has a reduced number of lysine residues relative to the sequence of the naturally-occurring protein.

In one embodiment, a protein selectively labeled on cysteine comprises two or more copies of an amino acid sequence having homology to an amino acid sequence of a naturally-occurring protein in which the derived amino acid sequence lacks lysine. In one embodiment, a cysteine-labeled protein comprises two or more copies of an amino acid sequence homologous to a naturally-occurring protein sequence, in which all of the lysine residues of the naturally-occurring protein sequence have been removed or changed to an amino acid other than lysine. The invention also includes nucleic acid constructs that encode proteins that comprise two or more copies of an amino acid sequence homologous to an amino acid sequence of a naturally-occurring protein, in which all of the lysine codons have been deleted or changed to non-lysine codons.

In some embodiments, a protein of a pre-labeled protein standard set that is selectively labeled on cysteine comprises an amino acid sequence homologous to an amino acid sequence of an nucleotide-disulfide oxidoreductase, such as a lipoamide dehydrogenase, a glutathione reductase, or a thioredoxin that is depleted in lysine residues. In some preferred embodiments, an amino acid sequence is homologous to an amino acid sequence of a thioredoxin, for example, homologous to a truncated thioredoxin sequence. In some preferred embodiments, an amino acid sequence homologous to an amino acid sequence of a thioredoxin differs from the naturally-occurring thioredoxin sequence by lacking lysine residues. In some preferred embodiments, a selectively labeled pre-labeled protein standard is devoid of lysine residues and is labeled on one or more cysteine residues, and comprises one or more copies of an amino acid sequence homologous to at least a portion of a thioredoxin.

The invention in some aspects provides pre-labeled protein standard sets that comprise a plurality of labeled proteins, in which two or more of the labeled proteins comprise a labeling compound conjugated to a first amino acid, and the ratios of the number of residues of the first amino acid to molecular weight for the two or more labeled proteins are within 10%, 5%, 2.5%, or 1% of one another. In some preferred embodiments, the proteins having ratios of first amino acid to molecular weight within 10%, 5%, 2.5%, or 1% of one another are selectively labeled on a first amino acid. In some exemplary embodiments, pre-labeled protein standard sets of the invention comprise a plurality of labeled proteins, in which two or more of the labeled proteins comprise a labeling compound on a first amino acid and lack residues of a second amino acid, in which the ratios of the number of residues of the first amino acid to molecular weight of the two or more selectively labeled proteins are within 10%, 5%, 2.5%, or 1% of one another.

In some preferred embodiments of a pre-labeled protein standard set, at least two proteins comprising a labeling compound on a first amino acid have between one and ten residues of a first amino acid per 10 kDa, such as between two and seven residues of a first amino acid, such as between three and five residues of a first amino acid, such as between 3.5 and 4.5 residues of a first amino acid per 10 kDa. In some preferred embodiments of a pre-labeled protein standard set, at least three, at least four, at least five, at least six, at least seven, at least eight, at least nine, or at least ten proteins labeled on a first amino acid have between one and ten residues of a first amino acid per 10 kDa, such as between two and seven residues of a first amino acid, such as between three and five residues of a first amino acid, such as between 3.5 and 4.5 residues of a first amino acid per 10 kDa.

In some aspects of the invention, a pre-labeled protein standard set can include one or more proteins labeled on a first amino acid that include one or more copies of an amino acid sequence derived from a naturally-occurring protein, in which the amino acid sequence comprises one or more amino acid changes that alter the number or spacing of a first amino acid targeted for labeling.

The selectively labeled proteins provided in some preferred embodiments of aspects of the invention do not differ substantially in their migration in denaturing acrylamide electrophoresis gels from the migration of the same proteins in unlabeled form. In some preferred embodiments, the selectively labeled proteins provided in preferred embodiments do not differ by more than 10%, more than 7%, or more than 5% in their migration in denaturing acrylamide electrophoresis gels from the migration of the same proteins in unlabeled form. In some preferred embodiments, the selectively labeled proteins having a molecular weight of greater than 10 kDa or greater do not differ by more than 5% in their migration in denaturing acrylamide electrophoresis gels from the migration of the same proteins in unlabeled form.

The proteins of a pre-labeled protein standard set provided in some preferred embodiments of aspects of the invention, when electrophoresed on a denaturing polyacrylamide gel, produce bands with widths that do not differ by more than two-fold between different proteins of the set that have molecular weights of 10 kDa or greater. In some preferred embodiments, the labeled proteins of a pre-labeled protein standard set having molecular weights between 20 kDa and 100 kDa produce visually detectable bands on electrophoresis gels having widths that do not differ by more than 50%. In some preferred embodiments, the widths of visually detectable bands produced by at least five pre-labeled proteins of a standard set do not differ by more than 30%.

Pre-labeled protein standard sets disclosed herein can include two, three, four, five, six, seven, eight, nine, ten, eleven, twelve, thirteen, fourteen, fifteen, or more labeled proteins, in which one, two, three, four, five, six, seven, eight, nine, ten, eleven, twelve, thirteen, fourteen, fifteen, or more of the labeled proteins is selectively labeled on a first amino acid. In preferred embodiments of the invention, at least two different proteins pre-labeled protein standard set are labeled with different labeling compounds, preferably two different dyes. Where a pre-labeled protein standard set includes two or more, three or more, four or more, or five or more labeled proteins, a pre-labeled protein standard can include different proteins that are labeled with two or more, three or more, four or more, or five or more different dyes.

A pre-labeled protein standard set of the invention in preferred embodiments spans a molecular weight range of from about 1 kDa to about 10 kDa, from about 5 kDa to about 50 kDa, from about 100 kDa to about 500 kDa, from about 10 kDa or less to about 100 kDa or greater, or from about 10 kDa or less to about 150 kDa or greater, or from about 5 kDa or less to about 150 kDa or greater, or from about 10 kDa or less to about 200 kDa or greater, or from about 5 kDa or less to about 200 kDa or greater, or from about 10 kDa or less to about 250 kDa or greater, or from about 5 kDa or less to about 250 kDa or greater.

In some embodiments, the invention provides pre-labeled molecular weight standard sets in which three, four, five, six, seven, eight, nine, ten, eleven, twelve, thirteen, fourteen, fifteen, or more of the labeled proteins of the set differ in size from one another by molecular weight increments that are multiples of 5 kDa, 10 kDa, 20 kDa, or 50 kDa. In some illustrative embodiments, at least five, six, seven, eight, nine, or ten molecular weight markers can differ in size by increments that are multiples of 5 kDa. In some illustrative embodiments, at least five, six, seven, eight, nine, or ten molecular weight markers can differ in size by increments that are multiples of 10 kDa. In some preferred embodiments, the two or more labeled proteins are comprise a labeling compound bound to a first amino acid and comprise one or more copies of an amino acid sequence of or derived from an amino acid sequence of a naturally-occurring protein, in which the amino acid sequence of or homologous to an amino acid sequence of a naturally-occurring protein lacks residues of a second amino acid that can react with the labeling compound.

The invention also includes a set of pre-labeled protein standards as in any of the previous embodiments, in which the plurality of labeled proteins are provided in one or more solutions. A solution can include one or more buffers, reducing agents, chelators, alcohols, detergents, or dyes.

In another aspect, the invention provides methods of labeling proteins that include attaching a label to one or more lysine residues to a protein that lacks cysteine residues. The method includes: adding a labeling compound to a protein that lacks cysteine residues under conditions that allow conjugation of the dye with lysine. In these methods, a labeling compound comprises at least one amino-reactive group.

In a further aspect, the invention provides methods of labeling proteins that include attaching a label to one or more cysteine residues to a protein that lacks lysine residues. The method includes: reducing cystines of a protein that lacks lysine residues and adding a labeling compound to the protein under conditions that allow conjugation of the dye with cysteine. In these methods, a labeling compound has at least one sulfhydryl-reactive group.

In a further aspect, methods are provided for determining the molecular weight of a sample protein using a pre-labeled protein standard set provided herein. The method includes electrophoresing a sample that includes one or more proteins in a first lane of a gel and electrophoresing a pre-labeled protein standard set that comprises at least two labeled proteins that are selectively labeled on a first amino acid in a second lane of the gel, determining the migration distance of at least two of the two or more labeled proteins of the standard, determining the migration distance of at least one of the one or more sample proteins, and calculating the molecular weight of the at least one sample protein based on the migration distance and molecular weights of the at least two labeled proteins of the standard. The method can be performed using curve-fitting or point-to-point calibration based on the migration of the at least two labeled standards or by calibration of protein standard migration normalized to dye front migration.

The invention also includes kits that include the described pre-labeled protein standard sets, and further comprise one or more of one or more buffers, loading dyes, reducing agents, unlabeled protein standards, blotting membranes, pre-cast gels, or electrophoresis buffers. The components of the kit can in one or more containers, and two or more of the components of the kit can be provided in a common package (such as, for example, a box, rack, or jar). The kit can also include instructions for use, or instructions for accessing protocols for use via the internet.

The set of pre-labeled protein standards of the kit can be provided as lyophilized solids, or in solution in liquid or frozen form. A solution comprising one or more labeled protein standards of a set can include one or more buffers, reducing agents, chelators, alcohols, detergents, or dyes. The set of pre-labeled protein standards of the kit can include at five, six, seven, eight, nine, ten, eleven, twelve, or more labeled protein standards that are provided as one or more mixtures of two or more labeled standards. In some embodiments, all of the proteins of a pre-labeled protein standard set are provided in a single mixture (which can be provided in one or more aliquots) in a kit. The proteins of a pre-labeled protein standard set provided in a kit preferably span a molecular weight range of from 10 kDa or less to 100 kDa or more, and can span a molecular weight range of from 5 kDa or less to 250 kDa or more.

In yet another aspect, the invention provides methods of providing a set of pre-labeled protein standards to a customer, in which the set of pre-labeled protein standards includes any of the pre-labeled standard sets and kits disclosed herein. In one embodiment, the method includes: providing a pre-labeled protein standard set to a customer, in which at least one of the labeled proteins of the standard set is selectively labeled on a first amino acid, in exchange for revenue.

BRIEF DESCRIPTION OF THE DRAWINGS

FIG. 1 A) depicts on line 2 the nucleic acid sequence of a truncated *E. coli* bacterial thioredoxin ORF (SEQ ID NO:9) with a C-terminal his tag, aligned with the a modified truncated *E. coli* bacterial thioredoxin ORF same sequence in which all of the lysine codons have been mutated to arginine codons and two cysteines have been added, and having a C-terminal his tag (SEQ ID NO:10) on line 1. B) depicts the translated amino acid sequence of truncated *E. coli* bacterial thioredoxin having a C-terminal his tag on line 2 (SEQ ID NO:11) aligned with the same sequence in which all of the lysines have been changed to arginines and two cysteines have been added on line 1 (SEQ ID NO:12).

FIG. 7 provides the nucleic acid sequence of the "No Lysine" 50 kDa ORF insert (SEQ ID NO:37) generated from pTrc BH 60 kDa.

FIG. 10 shows the sequence of a truncated Lac Z gene (SEQ ID NO:40) that was used to synthesize the pTrc 260 kd plasmid.

FIG. 13 depicts the reaction scheme for generating the vinyl sulfone form of Orange 16.

DETAILED DESCRIPTION OF THE INVENTION

Definitions

Figure 2A:
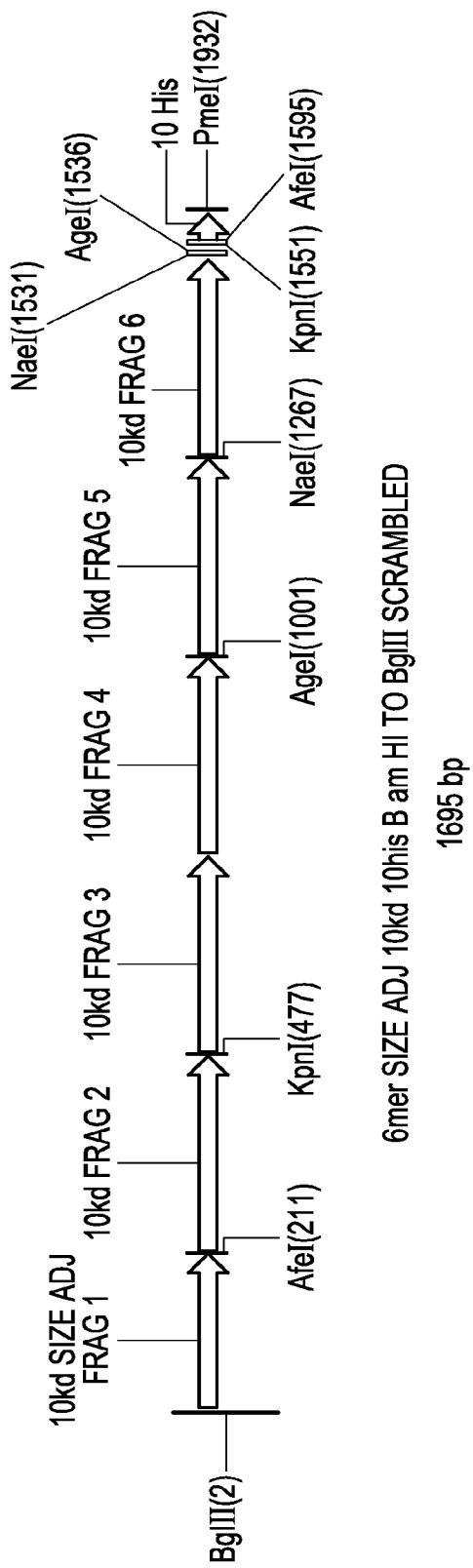
FIG. 2 A) is a diagram of a nucleic acid construct (BH6mer ORF) having six copies of a truncated thioredoxin sequence lacking lysine separated by unique restriction sites. B) provides the nucleic acid sequence of BH6mer ORF (SEQ ID NO:13).

In the description that follows, a number of terms used in recombinant DNA technology and protein chemistry are utilized extensively. In order to provide a clear and consistent understanding of the specification and claims, including the scope to be given such terms, the following definitions are provided.

As used herein, the articles "a," "an" and "one" mean "at least one" or "one or more" of the object to which they refer, unless otherwise specified or made clear by the context in which they appear herein.

As used herein, the terms "about" or "approximately" when referring to any numerical value are intended to mean a value of ±10% of the stated value. For example, "about 50° C." (or "approximately 50° C.") encompasses a range of temperatures from 45° C. to 55° C., inclusive. Similarly, "about 100 mM" (or "approximately 100 mM") encompasses a range of concentrations from 90 mM to 110 mM, inclusive.

The term "label" as used herein refers to a chemical moiety or protein that is directly or indirectly detectable (e.g. due to its spectral properties, conformation or activity) when attached to a target or compound and used in the present methods. The label can be directly detectable (fluorophore, chromophore) or indirectly detectable (hapten or enzyme). Such labels include, but are not limited to, radiolabels that can be measured with radiation-counting devices; pigments, dyes or other chromophores that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, dyes, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS ($9^{th}$ edition, CD-ROM, September 2002), supra.

The term "directly detectable" as used herein refers to the presence of a material or the signal generated from the material is immediately detectable by observation, instrumentation, or film without requiring chemical modifications or additional substances.

"Detectable by the naked eye" means the referred to entity is directly visible by a human being having normal vision without the aid of, for example, glasses that magnify or filter light or a microscope (or lens of any type that provides magnification), and without the aid of illumination of greater intensity than standard laboratory room fluorescent or incandescent lighting, or illumination with light of narrower wavelength(s) than standard laboratory room fluorescent or incandescent lighting, or illumination with wavelength(s) outside that of standard laboratory room fluorescent or incandescent lighting.

A "dye" is a visually detectable label. A dye can be, for example, a chromophore or a fluorophore. A fluorophore can be excited by visible light or non-visible light (for example, UV light).

A "chromophore" is a chemical group or compound capable of selective light absorption resulting in the coloration of the organic compound.

The term "fluorophore" as used herein refers to a composition that is inherently fluorescent or demonstrates a change in fluorescence upon binding to a biological compound or metal ion, i.e., fluorogenic. In many cases, fluorophores are also chromophores that have an observable color when they absorb light. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, September 2002).

A "textile dye" is a dye typically used to dye cloth fabrics and material for making cloth fabrics (e.g., fibers, yarn, thread), such as cloth fabrics that comprises, for example, cotton, wool, polyamide (nylon), polyester, viscose, acrylic, acetate, triacetate, etc. Textile dyes can also be used to dye materials and compounds other than fabrics and materials for making fabrics. Textile dyes are available from many commercial suppliers (for example, Burlington Chemical Co., Burlington, N.C.; Harneet Exports, Mumbai, India; Jagson Colorchem Ltd., Ahmadabed, India; Jaychem, Sanand, India; Omega Dyes, Goucestershire, UK; Dystar Textilfarben, Frankfurt, Germany; Kemtex, Chorley, UK). Nonlimiting examples of textiles dyes are Remazol dyes, Kemozol dyes, Direct dyes, Disperse dyes, Dischargeable acid dyes, Kenanthol dyes, Kenamide dyes, Cibacron dyes, azoic dyes, Dyacid dyes, Kemtex reactive dyes, Kemtex acid dyes, Kemtex Easidye acid dyes, Calcdon dyes, Cassulfon dyes, Isolan dyes, Sirius dyes, Imperon dyes, phtalogen dyes, naphtol dyes, Levafix dyes, Procion dyes, and isothiocyanate dyes.

A "pre-labeled" biomolecule is a biomolecule that includes a label prior to performing a separation or experiment with the biomolecule. For example, a pre-labeled standard is labeled prior to separation of that standard by biochemical techniques such as, but not limited to, electrophoresis (including both solution phase and gel electrophoresis), isoelectric focusing, spectrometry, or chromatography.

In the context of the present invention, "selectively labeled" means labeled predominantly on particular sites of a biomolecule. In particular, a protein that is "selectively labeled" on a [first] amino acid is a protein that has been conjugated with a labeling compound that has a reactive chemical group that is specific for the [first] amino acid, and that either has fewer than one residue per 10 kDa of one or more other (second) amino acids that can also react with the labeling compound, or has a chemical modification of one or more other (second) amino acids that can also react with the labeling compound. Selective labeling of proteins is accomplished by the use of labeling compounds having reactive chemical groups that are specific for one or more particular chemical groups present on one or more amino acids on proteins, and by reducing side-reactions of the reactive group of the dye with one or more other amino acids that are capable of reacting with the reactive group of the dye. Reducing side reactions can be by either or both of: modifying one or more chemical groups that are capable of reacting with the reactive group of the dye such that they are no longer capable of reacting with the labeling compound under the reaction conditions used to label the protein, and selecting a protein for labeling that is depleted in amino acids that have chemical groups capable of reacting with the dye used for labeling the protein.

"Amino acid" refers to the twenty naturally-occurring amino acids, as well as to derivatives of these amino acids that occur in nature or are produced outside of living organisms by chemical or enzymatic derivatization or synthesis (for example, hydroxyproline, selenomethionine, azido-labeled amino acids, etc.)

In the context of the present application, a "target amino acid" or "an amino acid targeted for labeling" is an amino acid that is used for the covalent attachment of a label, such as a dye, to a peptide or protein. "Target amino acid" refers to an amino acid species, for example lysine, by which is meant all lysine residues of a protein, and is not used to refer to a single particular lysine residue of a protein. In making labeled protein standards of the invention, a target amino acid is an amino acid whose labeling is intended; the labeling of a protein on a target amino acid is achieved by selecting a labeling compound with a reactive chemical group that reacts with the reactive chemical group on the target amino acid.

A "nontarget amino acid" is an amino acid on a protein standard that has a reactive group that is capable of reacting with a labeling compound conjugated to a target amino acid of the protein standard, but whose conjugation to a labeling compound is not desired. A "nontarget amino acid" can have the same reactive chemical group as a target amino acid or a different reactive chemical group. A non-target amino acid can have greater, less, or substantially the same affinity for a labeling compound as a target amino acid.

A protein that is "depleted in an amino acid" means that the protein has fewer than one residue of the amino acid per 10 kDa. In some preferred embodiments of the invention, a protein standard that is depleted in a non-target amino acid has no residues of a non-target amino acid (lacks a non-target amino acid).

A protein that is "deficient in an amino acid" means that the protein has no residues of the amino acid.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having acidic side chains is glutamic acid and aspartic acid; a group of amino acids having amino-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. Preferred conservative amino acid substitution groups are: valine-leucine-isoleucine; phenylalanine-tyrosine; lysine-arginine; alanine-valine; glutamic acid-aspartic acid; and asparagine-glutamine.

The term "reactive group" or "reactive chemical group" as used herein refers to a chemical group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include without limitation nucleophiles, electrophiles and photoactivatable groups.

"Conjugated to" means covalently bound to. A molecule or chemical group that is conjugated to another molecule or chemical group is covalently bound. To conjugate [a molecule or chemical group to another molecule or chemical group] is to cause or promote a chemical reaction between the two referenced molecules or chemical groups such that they become covalently bound.

As used herein an amino acid or reactive group of an amino acid that "reacts with" a labeling compound becomes covalently bound to the labeling compound.

TABLE 1

Reactive Groups of Amino Acids

| Amino Acid | Reactive Group | Specific type of reactive group | pKa of side chain (theoretical) |
|---|---|---|---|
| Cysteine | sulfhydryl | | 8.8-9.1 |
| N-terminal | amine | Alpha amine | 7.6-8.0 |
| Lysine | amine | Epsilon amine | 9.3-9.5 |
| Histidine | amine | Imidazole | 6.7-7.1 |
| Tryptophan | amine | Indoyl amine | — |
| Arginine | amine | Guanidino amine | >12.0 |
| C-terminal | carboxyl | Alpha carboxyl | 2.1-2.4 |
| Aspartic acid | carboxyl | Beta carboxyl | 3.7-4.0 |
| Glutamic acid | carboxyl | Gamma carboxyl | 4.2-4.5 |
| Tyrosine | hydroxyl | Phenolate | 9.7-10.1 |
| Methionine | thioether | | — |
| Asparagine | amidino | | |

As used herein, "protein" means a polypeptide, or a sequence of two or more amino acids, which can be naturally-occurring or synthetic (modified amino acids, or amino acids not known in nature) linked by peptide bonds. "Peptide" specifically refers to polypeptides of less than 10 kDa. As used herein, the term "protein" encompasses peptides.

"Naturally-occurring" refers to the fact that an object having the same composition can be found in nature. For example, a polypeptide or polynucleotide sequence that is present in an organism, including viruses, that can be isolated from a source in nature, and that has not been intentionally modified in the laboratory is naturally-occurring.

A nucleic acid (or nucleotide) or protein (or amino acid) sequence that is "derived from" another nucleic acid (or nucleotide) or protein (or amino acid) sequence is either the same as at least a portion of the sequence it is derived from, or highly homologous to at least a portion of the sequence it is derived from, having at least 65%, 70%, 75%, 80%, 85%, 90%, 95%, 97%, 98%, or 99% identity with the sequence of the protein from which it is derived. An amino acid sequence derived from the sequence of a naturally-occurring protein can be referred to as a "naturally-occurring protein-derived amino acid sequence" or, simply, "a derived [amino acid] sequence". A nucleic acid sequence derived from the sequence of a naturally-occurring nucleic acid can be referred to as a "naturally-occurring nucleic acid-derived nucleic acid sequence" or, simply, "a derived [nucleic acid] sequence".

"Homologous" means that a protein peptide, or amino acid sequence has at least 65%, at least 70% amino acid sequence identity, at least 80% amino acid sequence identity, preferably 90% amino acid sequence identity, and more preferably at least 95% amino acid sequence identity with amino acid sequence referred to. The sequence having homology with another amino acid sequence has at least six amino acids, preferably at least 10 amino acids, and more preferably at least twenty, at least thirty, or at least forty contiguous amino acids of the protein, peptide, or amino acid sequence referred to.

A "variant" of a wild-type protein or peptide sequence is a sequence having at least 70%, preferably at least 80%, at least 90%, at least 95%, or at least 99% sequence identity with at least 20 contiguous amino acids of the wild-type protein.

"Recombinant methods" are methods that include the manufacture of or use of recombinant nucleic acids (nucleic acids that have been recombined to generate nucleic acid molecules that are structurally different from the analogous nucleic acid molecule(s) found in nature). Recombinant methods can employ, for example, restriction enzymes, exonucleases, endonucleases, polymerases, ligases, recombination enzymes, methylases, kinases, phosphatases, topoisomerases, etc. to generate chimeric nucleic acid molecules, generate nucleotide sequence changes, or add or delete nucleic acids to a nucleic acid sequence. Recombinant methods include methods that combine a nucleic acid molecule directly or indirectly isolated from an organism with one or more nucleic acid sequences from another source. The sequences from another source can be any nucleic acid sequences, for example, gene expression control sequences (for example, promoter sequences, transcriptional enhancer sequences, sequence that bind inducers or promoters of transcription, transcription termination sequences, translational regulation sequences, internal ribosome entry sites (IRES's), splice sites, poly A addition sequences, poly A sequences, etc.), a vector, protein-encoding sequences, etc. The nucleic acid sequences from a source other than the source of the nucleic acid molecule directly or indirectly isolated from an organism can be nucleic acid sequences from or within the genome of a different organism. Nucleic acid sequences in the genome can be chromosomal or extra-chromosomal (for example, the nucleic acid sequences can be episomal or of an organelle genome). Recombinant methods also includes methods of introducing nucleic acids into cells, including transformation, viral transfection, etc. to establish recombinant nucleic acid molecules in cells. "Recombinant methods" also includes the synthesis and isolation of products of nucleic acid constructs, such as recombinant RNA molecules and recombinant proteins. "Recombinant methods" is used interchangeably with "genetic engineering" and "recombinant [DNA] technology".

A "recombinant protein" is a protein made from a recombinant nucleic acid molecule or construct. A recombinant protein can be made in cells harboring a recombinant nucleic acid construct, which can be cells of an organism or cultured prokaryotic or eukaryotic cells, or can made in vitro using, for example, in vitro transcription and/or translation systems.

"Do not differ substantially" or "substantially the same" means that the referenced compositions or components differ by less than 10% of the larger of the compared values.

The term "purified" as used herein refers to a preparation of a protein that is essentially free from contaminating proteins that normally would be present in association with the protein, e.g., in a cellular mixture or milieu in which the protein or complex is found endogenously such as serum proteins or cellular lysate.

"Substantially purified" refers to the state of a species or activity that is the predominant species or activity present (for example on a molar basis it is more abundant than any other individual species or activities in the composition) and preferably a substantially purified fraction is a composition wherein the object species or activity comprises at least about 50 percent (on a molar, weight or activity basis) of all macromolecules or activities present. Generally, a substantially pure composition will comprise more than about 80 percent of all macromolecular species or activities present in a composition, more preferably more than about 85%, 90%, or 95%.

The term "sample" as used herein refers to any material that may contain a biomolecule or an analyte for detection or quantification. The biomolecule or analyte may include a reactive group, e.g., a group through which a compound of the invention can be conjugated to the analyte. The sample may also include diluents, buffers, detergents, and contaminating species, debris and the like that are found mixed with the target. Illustrative biological examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, salts, alcohols, extractants, lipids, solvents, detergents, reducing agents, chelators, anti-coagulants, preservatives, anti-microbial agents, and the like. A sample can include one or more partially or substantially purified biomolecules or analyte. A sample can be a live cell, a biological fluid that comprises endogenous host cell proteins, nucleic acid polymers, nucleotides, oligonucleotides, peptides and buffer solutions. The sample can be in an aqueous solution, a viable cell culture or immobilized on a solid or semi solid surface such as a polyacrylamide gel, membrane blot or on a microarray.

Two or more proteins "have electrophoretic separation characteristics that are substantially the same" or "do not differ substantially in their migration in acrylamide electrophoresis gels" when the molecular weights calculated for the two or more referenced proteins by their migration distance on a gel, such as a polyacrylamide gel, are within 10%, preferably within 7% or within 5%. The calculated molecular weights of the proteins can be performed by curve-fitting of molecular weight to migration distances or point-to-point calculation.

Pre-labeled Protein Standard Sets with Proteins Selectively Labeled on a First Amino Acid The invention provides pre-labeled protein standard sets comprising a plurality of labeled proteins, in which one or more of the labeled proteins is selectively labeled on a first amino acid. A protein selectively labeled on a first amino acid is a protein that comprises a labeling compound conjugated to one or more residues of a first amino acid and either: a) is depleted in residues of a second amino acid that reacts with a labeling compound; or b) comprises one or more copies of an amino acid sequence derived from the amino acid sequence of a naturally-occurring protein, in which the amino acid sequence derived from the amino acid sequence of a naturally-occurring protein has a reduced number of residues of a second amino acid capable of reacting with the labeling compound relative to the wild-type amino acid sequence of the naturally occurring protein.

A protein that is depleted in residues of a second amino acid is a protein that has fewer than one residue of the second amino acid per 10 kDa. A protein that is depleted in residues of a second amino acid can have no residues of a second amino acid.

In the context of the present invention, a first amino acid is an amino acid whose labeling is desired, and whose labeling is targeted by the choice of reactive group on a labeling compound. A first amino acid is referred to herein as a "target amino acid".

In the context of the present invention, a second, or non-target, amino acid is an amino acid whose labeling is not desired, but that has a reactive chemical group that, under conditions used to label the protein on a first amino acid, reacts with the labeling compound that is used to label the protein. In some embodiments, a non-target amino acid has the same reactive group as the target amino acid. In some embodiments, a non-target amino acid has a different reactive group from the target amino acid. The present invention seeks to reduce labeling of non-target amino acids by reducing their occurrence in a protein used as a pre-labeled protein standard.

One or more proteins of a set of labeled protein standards can be selectively labeled, for example, on the sulfhydryl group of cysteine, on the primary amine of an N-terminal amino acid and/or the primary amine of lysine, on the secondary amine of the imidazoyl group of histidine or the indole ring of tryptophan, on the carboxyl groups of the C-terminal amino acid or of aspartate or glutamate, on the thioether of methionine, on the phenolate of tyrosine, or on the amidino group of asparagine. Any of the amino acids: cysteine, lysine, histidine, tryptophan, aspartate, glutamate, methionine, tyrosine, or asparagines can be target amino acids to which a labeling compound can be conjugated. Any of the amino acids cysteine, lysine, histidine, tryptophan, aspartate, glutamate, methionine, tyrosine, or asparagine can also be a non-target amino acid whose interaction with a labeling compound is sought to be reduced or eliminated when a protein is labeled on a first amino acid.

For example, in some exemplary embodiments, cysteine can be a target amino acid and one or more of lysine histidine, or tryptophan can be a non-target amino acid. In other exemplary embodiments, lysine can be a target amino acid and one or more of cysteine, histidine, or tryptophan can be a non-target amino acid.

A selectively labeled protein can have more than one target amino acid. For example, both glutamate and aspartate can be target amino acids. A selectively labeled protein can have more than one non-target amino acid. For example, lysine can be a target amino acid, and two or more of cysteine, arginine, histidine, and tryptophan can be non-target amino acids.

In yet other embodiments, the first amino acid is histidine and the second amino acid is one or more of cysteine, lysine, or tryptophan. In other embodiments, the first amino acid is tryptophan and the second amino acid is one or more of cysteine, lysine, histidine, or asparagines. In further embodiments, the first amino acid is asparagine and the second amino acid is one or more or cysteine, lysine, histidine, or tryptophan. In additional embodiments, the first amino acid is tyrosine and the second amino acid is one or more of cysteine, lysine, histidine, or tryptophan. The first amino acid can in yet further embodiments be methionine and the second amino acid can be one or more of cysteine, lysine, histidine, tyrosine, or tryptophan.

Selectively labeled protein standards of the invention comprise a labeling compound on a first amino acid (a target amino acid) and are depleted in a second amino acid (a non-target amino acid), or comprise a labeling compound on a first amino acid (a target amino acid) and comprise an amino acid sequence having homology to an amino acid sequence of a naturally-occurring protein, in which the derived sequence has fewer residues of the second amino acid with respect to the wild-type sequence of the naturally occurring protein. In targeting an amino acid for labeling, a labeling compound is selected that has a reactive group that specifically reacts with the reactive group of the target amino acid to form a covalent bond, thereby forming a labeling compound-protein conjugate, or labeled protein. Preferably, a labeling compound used to label a protein standard has a high specificity for the reactive group of the target amino acid. Labeling compounds can be selected based on their reactive groups, or can be modified, using methods known in the art, to have reactive groups with high specificity for a target amino acid. Preferably, reaction conditions that optimize the reaction of the reactive chemical groups of the labeling compound and target amino acid are used for conjugating a selected label to the target amino acid.

A second amino acid, or non-target amino acid, is an amino acid that is capable of reacting with a labeling compound used to label a target amino acid of a protein under reaction condition used to conjugate the labeling compound to a target amino acid, but whose conjugation with a labeling compound is not desired. A non-target amino acid can be capable of reacting with a label used to label a target amino acid with substantially the same efficiency as the target amino acid, with reduced efficiency with respect to the reaction of the target amino acid with the label, or with greater efficiency with respect to the reaction of the target amino acid with the label. In certain illustrative examples, the non-target amino acid is capable of reacting with the label more efficiently than any other amino acid in the protein, except for the first amino acid.

In selecting one or more target amino acids and minimizing labeling of one or more non-target amino acids for labeling a protein standard, the reactivities of the groups present on amino acid side chains are taken into account. For example, the side chains of several amino acids include chemical groups that can act as nucleophiles in chemical conjugation reactions. Examples of such reactive chemical groups of amino acids include, without limitation, the sulfhydryl group of cysteine, the alpha amino group of N-terminal amino acids, the epsilon amino group of lysine, the imidazole amino group of histidine, the indoyl amino group of tryptophan, the guanidino group of arginine, the carboxyl group of the C-terminal amino acid of a protein, the carboxyl group of glutamic acid, the carboxyl group of aspartic acid, the phenolate of tyrosine, the thioether of methionine, and the amidino group of arginine. Reactions of these groups with a nucleophile-interacting group of a label will be more or less efficient depending on factors that include but are not limited to the reactive group of the label, the strength of the nucleophile group of the amino acid, and the pH at which the reaction occurs. For example, the sulfhydryl group of cysteine is generally a stronger nucleophile than the amino groups of lysine, the N-terminus of a protein, histidine, and tryptophan, which are stronger nucleophiles than the carboxyl groups of the C-terminus of a protein, aspartic acid, and glutamic acid, and the phenolate of tyrosine. In some preferred embodiments, a target amino acid of a pre-labeled protein standard can be an amino acid such as, but not limited to, cysteine, lysine, histidine, tryptophan, aspartic acid, glutamic acid, tyrosine, arginine, methionine, an N-terminal amino acid of the protein, or a C-terminal of the protein, in which one or more amino acids that also can undergo nucleophilic addition are non-target amino acid(s) that can be depleted in a pre-labeled protein standard.

For example, an amino acid having a chemical group that behaves as a nucleophile at a pH greater than neutrality, such as, for example, cysteine, lysine, tryptophan, or histidine, can be a target amino acid and one or more of the same group of amino acids that behave as nucleophiles at a pH greater than neutrality can be a non-target amino acid that is depleted in a labeled protein standard or is present in reduced amounts (relative to the corresponding wild-type protein sequence) in a labeled protein standard. In embodiments in which at least one of lysine, histidine, or tryptophan is a target amino acid, a label preferably includes an amino-reactive group for conjugation to the standard. Examples of amino-reactive groups that can be present on a compound used to label lysine, histidine, tryptophan, or an N-terminal amino acid include, but are not limited to, isothiocyanates, isocyanates, acyl azides, N-hydroxysuccinimide (NHS) esters, haloacetyl compounds, maleimide derivatives, sulfonyl chlorides, aldehydes, ketones, glyoxals, epoxides, oxiranes, carbonates, aryl halides, imidoesters, carbodiimides, or acid anhydrides.

In one example, lysine can be a target amino acid, and one or more of, for example, cysteine, histidine, or tryptophan can be non-target amino acid(s). In some illustrative embodiments, a selectively labeled protein standard selectively labeled on lysine is depleted in or lacks residues of at least one of cysteine, histidine, or tryptophan. A protein standard selectively labeled on lysine can optionally be made by recombinant methods from a nucleic acid construct that encodes at least a portion of a sequence of a naturally-occurring protein, in which one or more cysteine, histidine, or tryptophan codons has been removed by mutation or deletion. In some preferred embodiments, a protein standard selectively labeled on lysine is made from a nucleic acid construct in which all of the codons for at least one of cysteine, histidine, or tryptophan, or any combinations thereof, have been removed by deletion or mutation. A labeled protein standard of the invention that is selectively labeled on lysine can lack residues of one or more non-target amino acids and can have one or more additional non-target amino acids that are chemically modified such that they do not react with the labeling compound conjugated to the first amino acid.

In another example, cysteine can be a target amino acid, and one or more of lysine, tryptophan, or histidine, can be non-target amino acid(s). In these embodiments, preferably at least lysine is a non-target amino acid, since the reactivity of the primary amine of lysine is greater than that of the indoyl or imidazole amines of tryptophan or histidine, and thus lysine contributes more significantly to side reactions when conjugating a compound to cysteine. For example, cysteine can be a target amino acid of a pre-labeled protein standard where the labeling compound attached to the pre-labeled standard is a labeling compound that, prior to conjugation with the protein, comprised a reactive chemical group that reacts with the sulfhydryl group of cysteine, such as but not limited to: vinyl sulfone, iodoacetamide, maleimide, disulfides, mercurial compounds, haloacetyl compounds, and iodoacetic acid. In one example, a selectively labeled protein standard has a labeling compound conjugated to at least one cysteine residue and lacks residues of one or more of lysine, histidine, or tryptophan. In some preferred embodiments, a protein standard selectively labeled on cysteine is depleted in or has an amino acid sequence with a reduced number of residues of at least lysine relative to the corresponding wild-type amino acid sequence. A protein standard selectively labeled on cysteine can optionally be made by recombinant methods from a nucleic acid construct that encodes at least a portion of a sequence of a naturally-occurring protein, in which one or more lysine, histidine, or tryptophan codons has been removed. In some preferred embodiments, a protein standard selectively labeled on cysteine is made from a nucleic acid construct in which all of the codons for at least one of lysine, histidine, or tryptophan have been removed by deletion or mutation. A labeled protein standard of the invention that is selectively labeled on cysteine can lack one or more non-target amino acids and can have one or more additional non-target amino acids that are chemically modified.

In another example, an amino acid having a chemical group that behaves as a nucleophile at a pH lower than neutrality, for example, aspartate or glutamate, can be a target amino acid and one or more other amino acids that behaves as a nucleophile at a pH less than neutrality can be a non-target amino acid that is not present in a labeled protein standard or modified in a labeled protein standard. In one example, aspartate can be a target amino acid, and glutamate can be a non-target amino acid. In another example, glutamate can be a target amino acid, and aspartate can be a non-target amino acid. A labeling compound for glutamate or aspartate can include a carboxyl-reactive group, such as but not limited to, a diazoalkane, a diazoacetyl, a carbonyldiimidazole, or a carbodiimide.

Tyrosine can also be a target amino acid, in which a reactive chemical group on a label to be conjugated to the protein standard is, for example, a sulfonyl fluoride or iodoacetamide. Another potential target amino acid is methionine, in which a reactive chemical group on a compound used to label the protein standard is, for example, a haloacetate, a haloacetyl, or an aryl halide. Arginine can be a target amino acid, in which a chemical group on a compound used to label the protein is an oxalyl group.

In any of these examples an N-terminal amino acid, which can be labeled on the N-terminal amino group, can be a target amino acid or a non-target amino acid.

More than one amino acid can be targeted for selectively labeling a protein. For example, the N-terminal amino acid of a protein as well as lysine can be target amino acids, where a labeling compound conjugated to the selectively labeled protein includes a reactive chemical group that reacts with primary amines. In another example, glutamate, aspartate, and the C-terminal amino acid of a protein can be target amino acids, where a dye conjugated to the selectively labeled protein includes a reactive chemical group that reacts with carboxylates.

Methods for conjugating a label to particular amino acids of a protein, for example, the amino group of lysine residues, the N-terminus of the protein, histidine, and/or tryptophan; the sulfhydryl group of cysteine; the carboxyl group of aspartate and glutamate; as well as the thioether of methionine, and the phenolate of tyrosine are well known in the art (see, for example, Hermanson, *Bioconjugate Techniques*, Academic Press, San Diego (1996); Wong, Chemistry of Protein Conjugation and Cross-Linking, CRC Press, Boca Raton, 1993; Haugland, MOLECULAR PROBES HANDBOOK, available at www.invitrogen.com, (2002)). In general, methods for conjugation of a labeling compound to an amino acid residue of a protein comprise:

a) combining a protein that comprises a first amino acid that comprises a first reactive group with a labeling compound that comprises a second reactive group that reacts with the first reactive group, to form a protein-labeling compound mixture; and, b) incubating the protein-labeling compound mixture for a sufficient amount of time for the labeling compound to form a covalent bond with first reactive group of the first amino acid, wherein a labeled protein standard is formed.

In some preferred embodiments in which a first amino acid is cysteine, and the reactive group of cysteine is a sulfhydryl group, the method preferably also comprises:

c) prior to a), combining a protein that comprises one or more cysteine residues with a reducing agent; and d) incubating the protein with the reducing agent for a sufficient amount of time for cysteine-cysteine bonds to be reduced.

In some aspects, the invention includes a method for making a protein standard, comprising attaching a label to one or more cysteine residues of a protein that is depleted in lysine residues. For example, the method in some embodiments includes attaching a label that includes a sulfhydryl-reactive group, such as but not limited to a vinyl sulfone, an iodoacetamide, an maleimide, a disulfide, a mercurial compound, a haloacetyl compound, or an iodoacetic acid, to a protein that is depleted in lysine residues. In some embodiments, the protein that is depleted in lysine residues comprises an amino acid sequence that has homology to at least 40 amino acids of a naturally-occurring protein, such as at least 70%, at least 80%, or at least 90% homology to at least 40 amino acids of a naturally-occurring protein, and has fewer lysine residues than the amino acid sequence of the naturally-occurring protein to which it has homology. In some embodiments, the protein that is depleted in lysine residues comprises fewer than one residue of lysine per 10 kDa. In some embodiments, the protein that is depleted in lysine residues has no lysine residues.

In some aspects, the invention includes a method for making a protein standard, comprising attaching a label to one or more lysine residues of a proteins that is depleted in cysteine residues. For example, the method in some embodiments includes attaching a label that includes an amino-reactive group, such as but not limited to an isothiocyanate, an isocyanate, an acyl azide, an N-hydroxysuccinimide (NHS) ester, a haloacetyl compound, a maleimide derivative, a sulfonyl chloride, an aldehyde, a ketone, a glyoxal, an epoxide, an oxirane, a carbonate, an aryl halide, an imidoester, a carbodiimide, or an acid anhydride, to a protein that is depleted in cysteine residues. In some embodiments, the protein that is depleted in cysteine residues comprises an amino acid sequence that has homology to at least 40 amino acids of a naturally-occurring protein, such as at least 70%, at least 80%, or at least 90% homology to at least 40 amino acids of a naturally-occurring protein, and has fewer cysteine residues than the amino acid sequence of the naturally-occurring protein to which has homology. In some embodiments, the protein that is depleted in cysteine residues comprises fewer than one residue of cysteine per 10 kDa. In some embodiments, the protein that is depleted in cysteine residues has no cysteine residues.

In preferred methods, the labeling compound is a dye. Reactive dyes and their preparation are well known in the art (Haugland, MOLECULAR PROBES HANDBOOK, supra, (2002)).

In some preferred methods of labeling cysteine residues, the reducing agent is beta-mercaptoethanol, dithiothreitol, TCEP, or TBP. Reducing agents can be used at concentrations ranging from about 0.01 millimolar to about 50 millimolar, for example, from about 0.05 micromolar to about 20 millimolar, or from about 0.1 millimolar to about 10 millimolar, or from about 0.2 mM to about 5 mM, or from about 0.5 mM to about 2 mM.

Preferably, conjugation to form a covalent bond consists of simply mixing the reactive compounds of the present invention in a suitable solvent in which both the reactive compound and the substance to be conjugated are soluble. The reaction preferably proceeds spontaneously without added reagents at a suitable temperature.

Conjugation methods can vary and can be optimized according to the purposes of the practitioner, so the following description is illustrative and not limiting to the invention. Preparation of peptide or protein conjugates typically comprises first dissolving the protein to be conjugated in aqueous buffer at about. 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive label compound is dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the compound are added to the protein, the conjugate is purified (for example, using chromatography) to separate unconjugated compound and the protein-labeling compound conjugate is tested in its desired application. It is generally preferred that the reagents be kept as concentrated as practical so as to obtain adequate rates of conjugation. An excess of labeling compound over target amino acid is typically used in the labeling reaction.

Following addition of the reactive compound to the component solution, the mixture is incubated for a suitable period. The incubation can occur at any temperature, from close to 0 degrees C. to about 90 degrees C., but typically is for about 1 hour at room temperature or above (such as up to 60 degrees C.) to several hours on ice. After incubation, the excess labeling compound is removed by gel filtration, dialysis, HPLC, precipitation, adsorption on an ion exchange or hydrophobic polymer, or other suitable means. The dye-protein conjugate can be stored or used in solution or lyophilized.

Selectivity of labeling is best obtained by selection of an appropriate reactive dye. For example, modification of thiols with a thiol-selective reagent such as a haloacetamide, vinyl sulfone, or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

A labeling compound conjugated to a protein standard can be any type of label, but is preferably a directly detectable label, and is more preferably a dye that can be visually detected with the naked eye. Preferably, a labeling compound is a dye detectable with the naked eye such that labeled proteins can be detected in a gel immediately after, and preferably during, electrophoresis without the need for additional processing or image analysis of the gel. Preferably, a labeling compound is not an unmodified naturally-occurring amino acid.

The invention provides protein standards that behave in separation procedures substantially the same as their unlabeled counterparts; therefore the labels used in the invention are preferably of relatively low molecular weight, such as molecular weight of less than about 2 kDa, preferably less than about 1.5 kDa, more preferably less than about 1 kDa, and can be less than about 0.5 kDa. For example, the molecular weight of a labeling compound can be between about 0.1 kDa and about 1 kDa, or between about 0.2 kDa and about 1.5 kDa, or between about 0.3 kDa and about 1 kDa, or between about 0.4 kDa and about 0.8 kDa, so that the labeling compounds do not substantially alter separation rates of the proteins in electrophoresis or chromatography, for example.

A dye used to label a selectively labeled protein of a pre-labeled protein standard set can be or comprise a chromophore, a fluorophore, or can be or comprise both a fluorophore and chromophore. The dye can comprise a chromophore that is also a fluorophore. A chromophore can be any chromophore. In some embodiments, a chromophore is a textile dye, such as for example, a Direct dye, a Disperse dye, a Dischargeable acid dye, a Kenanthol dye, a Kenamide dye, a Dyacid dye, a Kemtex reactive dye, a Kemtex acid dye, a Kemtex Easidye acid dye, a Remazol dye, a Kemazol dye, a Calcdon dye, a Cassulfon dye, an Isolan dye, a Sirius dye, an Imperon dye, a phtalogen dye, a naphtol dye, a Levafix dye, a Procion dye, and an isothiocyanate dye. Examples of textile dyes that can be used to label protein standards include, for example, Remazol brilliant blue, Uniblue A, malachite green isothiocyanate, and Orange 16 (Remazol orange).

A dye used to label a selectively labeled protein standard of a pre-labeled protein standard set can be a fluorophore. As nonlimiting examples, a fluorophore used to label a protein standard can be an Alexa fluor dye, a BODIPY dye, fluoroscein or a derivative thereof, eosin or a derivative thereof, tetramethylrhodamine, rhodamine or a derivative thereof, Texas red or a derivative thereof, pyridyloxazole or a derivative thereof, NBD chloride, NBD fluoride, ABD-F, lucifer yellow or a derivative thereof, 8-anilino-1-naphthalenesulfonic acid (8-ANS) or a derivative thereof, or Oregon green or a derivative thereof. Although some amino acids may be weakly fluorescent, they are not considered fluorophores for the purposes of the invention, in which visual detection is preferred. For purposes of the invention therefore, naturally occurring amino acids including tryptophan and tyrosine are not considered labels or labeling compounds.

Dyes can include reactive groups, such as cysteine reactive groups (e.g., maleimide, iodoacetic acid, iodoacetamide, and vinyl sulfone) or amino reactive groups (such as, for example, isothiocyanates, isocyanates, acyl azides, N-hydroxysuccinimide (NHS) esters, sulfonyl chlorides, aldehydes, ketones, glyoxals, epoxides, oxiranes, carbonaes, aryl halides, imidoesters, carbodiimides, and acid anhydrides). Reactive chemical groups such as, for example, can be added to a dye using techniques that are known in the art of organic chemistry.

A dye can be tested for suitability in labeling a protein for use as a standard by labeling a protein with the dye to be tested on a target amino acid, in which at least one non-target amino acid of the protein is depleted in the protein, and performing a separation procedure on the labeled protein and the protein in unlabeled form, detecting the labeled and unlabeled protein after the separation procedure is completed, and comparing the separation of the labeled and unlabeled protein. The method can also include staining the unlabeled protein prior to detecting the unlabeled protein. For example, the migration of a labeled protein and the unlabeled form of the same protein can be compared on an electrophoresis gel, such as an acrylamide electrophoresis gel disclosed herein, for example a 4-12%, 4-16%, or 4-20% acrylamide gradient gel, in which the molecular weight of the labeled protein whose labeled and unlabeled form are being compared is greater than about 3.5 kDa, such as at least about 5 kDa, or such as at least about 10 kDa. Migration of selectively labeled and unlabeled forms of a protein are compared under electrophoresis conditions in which the loading dye front migrates at least 5 cm from the loading site and migration of a protein calculated to be about 10 kDa and the migration of a protein calculated to about 80 kDa are at least 3 cm apart at the completion of electrophoresis. Migration of selectively labeled and unlabeled forms of a protein are preferably compared under electrophoresis conditions in which the loading dye front (for example, a Coomassie loading dye front) migrates at least 6 cm from the loading site and migration of a protein calculated to be about 10 kDa and the migration of a protein calculated to about 80 kDa are at least 3.5 cm apart at the completion of electrophoresis. Migration of selectively labeled and unlabeled forms of a protein are preferably compared under electrophoresis conditions in which a the loading dye front migrates at least 6.5 cm, for example about 6.8 cm from the loading site and migration of a protein calculated to be about 10 kDa and the migration of a protein calculated to about 80 kDa are at least 3.5 cm apart at the completion of electrophoresis.

In comparing electrophoretic migration, molecular weights of labeled and unlabeled standards are calculated based on art-recognized methods using a curve generated from plotting migration distance of proteins (or a function thereof) versus molecular weight (or a function thereof, for example, the log of molecular weight), or using point-to-point calculation based on the migration distances of two proteins of known molecular weight electrophoresed on the same gel that preferably have molecular weights that bracket the molecular weight of the analyzed protein. Electrophoretic migration of labeled and unlabeled forms of a protein standard is within a given percentage when the difference in the calculated molecular weights of the labeled and unlabeled forms of the protein using either curve-fitting of molecular weight to migration distances or point-to-point calculation are within the given percentage.

Selectively Labeled Protein Standards Depleted in Residues of a Second Amino Acid In one aspect of the invention, a pre-labeled protein standard set includes one or more proteins selectively labeled on a first, or target, amino acid with a labeling compound, in which the one or more selectively labeled proteins is depleted in residues of a second, or non-target, amino acid that is capable of reacting with the labeling compound. A protein depleted in a non-target amino acid has fewer than one residue of a non-target amino acid per 10 kDa.

In one embodiment of this aspect, a protein of a pre-labeled protein standard set that is selectively labeled on a first amino acid comprises a naturally-occurring protein or a fragment thereof, in which the sequence of the naturally-occurring protein is depleted in residues of a non-target amino acid that is capable of reacting with the labeling compound conjugated to the target amino acid. For example, the protein that is selectively labeled can be a naturally-occurring protein that is isolated from cells, tissue, organisms, biological samples (including fluid samples, such as blood or serum), or media, where at least a portion of the protein naturally has a low abundance of a non-target amino acid. The protein can optionally be chemically or enzymatically proteolyzed to remove one or more portions of the protein, such as but not limited to a portion that includes one or more residues of a non-target amino acid. The protein that is selectively labeled can be a naturally-occurring protein that lacks a non-target amino acid and that is isolated from cells, tissue, organisms, biological samples, or media.

A selectively labeled protein depleted in a first amino acid can also be produced using recombinant methods, in which a nucleic acid sequence that encodes an amino acid sequence having homology to the sequence of a naturally-occurring protein is used to produce the protein in cells or in an in vitro synthesis system. An amino acid sequence having homology to the sequence of a naturally-occurring protein preferably has at least 70%, at least 80%, at least 90%, or at least 95% amino acid identity with at least twenty, at least thirty, at least forty, at least fifty, at least sixty, at least seventy, or at least eighty contiguous amino acids of the naturally occurring protein. In some embodiments, a selectively labeled protein has a labeling compound conjugated to a first amino acid, and includes an amino acid sequence having at least 70% homology to at least 30 contiguous amino acids of a naturally-occurring protein, in which the amino acid sequence has a reduced number of a second amino acid compared to the sequence of the naturally-occurring protein. The second amino acid is preferably a nontarget amino acid that can react with the labeling compound. In some embodiments, a selectively labeled protein is labeled on a first amino acid and includes an amino acid sequence having at least 80% homology to at least 40 contiguous amino acids of a naturally-occurring protein, in which the sequence having homology to the naturally-occurring protein has fewer residues of a second amino acid than the sequence of the naturally-occurring protein to which it is homologous. The second amino acid is preferably an amino acid that reacts with the labeling compound used to label the first amino acid.

The selectively labeled protein can, for example, be a recombinant protein that comprises one or more copies of an amino acid sequence derived from the sequence of a naturally-occurring protein that has fewer than one residue of a non-target amino acid per 10 kDa. A selectively labeled protein can include one or more copies of an amino acid sequence derived from a naturally-occurring protein that lacks a non-target amino acid.

In some embodiments, as disclosed above, the one or more selectively labeled proteins of the protein standard are made using recombinant methods, in which a protein is produced from a nucleic acid construct that comprises at least one copy of a nucleic acid sequence that encodes at least a portion of said naturally-occurring protein, in which the naturally occurring protein or portion thereof lacks residues of the second amino acid. In some embodiments, the one or more selectively labeled proteins of the protein standard are made using recombinant methods, in which a protein is produced from a nucleic acid construct that comprises at least one copy of a nucleic acid sequence that encodes at least a portion of said naturally-occurring protein, in which the nucleic acid sequence has been mutated to remove one or more codons of the second amino acid from the sequence. In some embodiments, one or more codons of the second amino acids is deleted from the nucleic acid sequence to delete amino acid residues from a standard protein that are capable of reacting with a labeling compound. In some embodiments, at least one of the one or more codons of the non-target amino acid is mutated to a codon for an amino acid other than the non-target amino acid. Mutation of a codon can be to any codon for an amino acid other than the non-target amino acid. The mutation of codons can be to any non-target codon and need not be restricted to conservative mutation. In some embodiments, mutation of a codon results in a conservative amino acid change in the amino acid sequence of the protein.

In embodiments in which the protein standard is made using recombinant methods, one or more mutations can be introduced into the nucleic acid sequence encoding the standard protein, where at least one mutation can alter a codon to change the number of residues of a target amino acid, or the position of a target amino acid. Increasing or decreasing the number of target amino acid residues can be done to optimize the number of label molecules attached to a protein standard. Codons of a target amino acid can also be mutated to optimize their position or spacing in a standard protein, which can affect labeling efficiency. Changing the position of a target amino acid in a protein can be done by altering codons and can be done to improve labeling efficiencies, for example by providing spacing between target amino acids to avoid steric hindrance during the labeling reaction, or to position a target amino acid farther from a charged group, hydrophobic region, etc. Codons of a target amino acid can be deleted, inserted, or mutated to codons of other amino acids, for example to provide proteins for labeling that include more than one target amino acid per 10 kDa, such as an average of 2, 3, 4, or more target amino acids per 10 kDa. Codons of a target amino acid can also be mutated to change the third nucleotide of the codon while retaining its amino acid specificity (through "wobble") to reduce the chance of recombination in the nucleic acid construct.

A naturally-occurring protein can be any naturally-occurring protein, and can be a prokaryotic or eukaryotic protein of any species. Proteins can be selected based on properties such as abundance in cells in which they are produced, ease of isolation, or sequence properties, such as, but not limited to, the abundance or accessibility of residues a target amino targeted for labeling in the sequence, or the lack of abundance of additional non-target amino acid(s) in the sequence. All or one or more portions of a sequence of a naturally-occurring protein can be used in a protein standard, or can be selected as a protein whose sequence can be mutated for engineering a protein for use as a selectively labeled protein standard.

For example, in some preferred embodiments of a pre-labeled protein standard, the target amino acid is lysine, and a non-target amino acid is cysteine. In this case protein sequences can optionally be selected base on the abundance of lysine and the paucity of cysteine in the amino acid sequence used, which in some embodiments can reduce the number of codons to be mutated. The amino acid sequence encoding the protein sequence can optionally be mutated to further reduce the number of residues of cysteine and/or other non-target amino acids, for example, histidine and/or tryptophan, which can be labeled in reactions that target lysine.

In other embodiments of a pre-labeled protein standard, the target amino acid is cysteine and a second amino acid is lysine. In this case protein sequences can optionally be selected base on the abundance of cysteine and the paucity of lysine in the amino acid sequence used, which in some embodiments can reduce the number of codons to be mutated.

In alternative embodiments, a selectively labeled protein that is depleted in a non-target amino acid can in some embodiments be a protein that comprises an amino acid sequence that has no known homology to a naturally-occurring protein, and can be designed and synthesized recombinantly or chemically, or using a combination of chemistry and recombinant technologies. A selectively labeled protein that is comprises sequence not derived from a naturally-occurring protein can in some preferred embodiments lack residues of a non-target amino acid.

Protein sequences lacking one non-target amino acid can also be further selected based on a low frequency of other potential non-target amino acids. For example, where lysine is a target amino acid to be conjugated with a dye, histidine and tryptophan, which are less reactive than lysine and cysteine but nonetheless can react with amino-reactive groups of labeling compounds, can optionally be considered non-target amino acids in addition to cysteine. In the present example, sequences lacking cysteine can optionally be analyzed for the frequency of these amino acids in the sequence as well.

A pre-labeled protein standard set can comprise a selectively labeled protein that comprises one, two, three, four, five, six, seven, eight, nine, ten, eleven, twelve, thirteen, fourteen, fifteen, sixteen, seventeen, eighteen, nineteen, twenty, or more copies of an amino acid sequence that is depleted in a non-target amino acid. In illustrative embodiments, the sequence lacks residues of a non-target amino acid. The amino acid sequence depleted or deficient in a non-target amino acid can be a designed sequence that lacks homology to a known naturally-occurring protein, or can be a sequence having homology to an amino acid sequence of a naturally-occurring protein, for example, having at least 70% homology to at least 30 contiguous amino acids of a naturally occurring protein, at least 80% homology to at least 40 contiguous amino acids of a naturally occurring protein, at least 80% homology to at least 50 contiguous amino acids of a naturally occurring protein. In some preferred embodiments of the invention, a pre-labeled protein standard set can include two or more selectively labeled proteins, in which the two or more selectively labeled proteins include a labeling compound conjugated to a first amino acid, and comprise different numbers of copies of an amino acid sequence that is depleted in or deficient in a second amino acid. The second amino acid is preferably a non-target amino acid that reacts with a labeling compound used to label the selectively labeled protein.

In one aspect, the invention includes a pre-labeled protein standard set that includes two or more proteins selectively labeled on a first amino acid with a labeling compound and depleted in a second amino acid capable of reacting with the labeling compound, in which the two or more selectively labeled proteins includes different numbers of copies of an amino acid sequence having at least 70% homology to at least 30 contiguous amino acids of a sequence of a naturally-occurring protein. The pre-labeled protein standard set can include two, three, four, five, six, seven, eight, nine, ten, eleven, twelve, thirteen, fourteen, fifteen, sixteen, seventeen, eighteen, nineteen, twenty, or more selectively labeled proteins that comprises different numbers of copies of an amino acid sequence that is depleted in residues of a second amino acid.

In one embodiment, a pre-labeled protein standard set of the invention comprises two or more proteins of different molecular weights that are labeled on lysine and depleted in cysteine residues. The invention includes in some illustrative embodiments a set of pre-labeled protein standards that includes at least two proteins of different molecular weight that are labeled on lysine and lack cysteine residues. The proteins selectively labeled on lysine can be isolated from cells, tissue, organisms, biological samples, or media, or can be made using recombinant methods. Using recombinant methods, proteins can be synthesized for use as selectively labeled standards, in which the proteins comprise one or more copies of a sequence that is depleted in or lacks cysteine. For example, a selectively labeled protein can comprise one or more copies of a sequence from the C-terminus of one or more ADP-ribosylation factors (Schurmann et al. Journal of Biological Chemistry 269: 15683 (1994)) or a sequence of one or more *Bacillus megaterium* spore proteins that lack cysteine residues (Setlow, Journal of Biological Chemistry 250: 8168 (1975)). Such sequences can be fused in any combination with themselves or other sequences to provide protein standards. Other amino acid sequences that lack cysteine can be found by searching gene or protein databases. Sequences lacking cysteine can be further selected based on the frequency residues of the target amino acid (e.g., lysine).

In some embodiments, the invention provides pre-labeled protein standard sets having a plurality of proteins selectively labeled on lysine and lacking cysteine, in which two or more selectively labeled proteins comprise one or more copies of an amino acid sequence that is depleted in cysteine. The pre-labeled protein standard set can include two or more, three, four, five, six, seven, eight, nine, ten, eleven, twelve, thirteen, fourteen, fifteen, sixteen, seventeen, eighteen, nineteen, twenty, or more proteins that are selectively labeled on lysine and lack depleted in cysteine, in which the selectively labeled proteins comprise one or more copies of an amino acid sequence depleted in cysteine. A protein standard selectively labeled on lysine is labeled with a labeling compound that comprises an amino-reactive group, such as, but not limited to, an isothiocyanate, an isocyanate, an acyl azide, an N-hydroxysuccinimide (NHS) ester, a sulfonyl chloride, an aldehyde, a ketone, a glyoxal, an epoxide, an oxirane, a carbonate, an aryl halide, an imidoester, a carbodiimides, or an acid anhydrides. A protein standard selectively labeled on lysine is preferably labeled with a dye that comprises an amino-reactive group.

In another embodiment, a pre-labeled protein standard set of the invention comprises two or more proteins of different molecular weights that are labeled on cysteine and depleted in lysine residues. The invention includes in some illustrative embodiments a set of pre-labeled protein standards that includes at least two proteins of different molecular weight that are labeled on cysteine and lack lysine residues. A selectively labeled protein can be a naturally-occurring protein isolated from cells, tissue, organisms, biological samples, or media, or can be made using recombinant methods. For example, using recombinant methods, sequences of proteins having at least a portion of the protein having fewer than one lysine per 10 kDa of protein, such as, for example, sequences encoding seed storage proteins of cereal crops (such as, for example, the zein proteins of maize, the gliadins of wheat), the L domain of HIV or Ebola viruses, or the WNK-1 and WNK-4 proteins (Coleman et al. Proc. Natl. Acad. Sci. 94: 709994-97 (1997); Shimoni et al. Journal of Biological Chemistry 271: 18869-18874 (1996); Yang et al J. Clin. Invest. 115: 1379-1387 (2005)) can be fused in any combination to provide protein standards. Other amino acid sequences that lack or are depleted in lysine can be found by searching gene or protein databases. Sequences depleted in a non-target amino acid can be further selected based on the frequency of the target amino acid, e.g., cysteine. Sequences depleted in lysine can be further selected based on low frequency of other potential non-target amino acids, such as, but not limited to, histidine or tryptophan.

In other embodiments, the invention provides pre-labeled protein standard sets having a plurality of proteins selectively labeled on cysteine and lacking lysine, in which two or more selectively labeled proteins comprise one or more copies of an amino acid sequence depleted in lysine. The pre-labeled protein standard set can include two or more, three, four, five, six, seven, eight, nine, ten, eleven, twelve, thirteen, fourteen, fifteen, sixteen, seventeen, eighteen, nineteen, twenty, or more proteins that are selectively labeled on cysteine and are depleted in lysine, in which the selectively labeled proteins comprise one or more copies of an amino acid sequence depleted in lysine. A protein standard selectively labeled on cysteine is labeled with a labeling compound that comprises an sulfhydryl-reactive group, such as, but not limited to, vinyl sulfone, iodoacetamide, maleimide, or iodoacetic acid. A protein standard selectively labeled on lysine is preferably labeled with a dye that comprises an sulfhydryl-reactive group.

Selectively Labeled Protein Standards Comprising an Amino Acid Sequence Derived from a Naturally-Occurring Protein In one aspect, the invention includes pre-labeled protein standard sets that have one or more selectively labeled proteins, in which a selectively labeled protein comprises a labeling compound conjugated to a first amino acid, and comprises one or more copies of an amino acid sequence derived from a naturally-occurring protein, in which the amino acid sequence derived from a naturally-occurring protein has a reduced number of residues of a second amino acid capable of interacting with the labeling compound relative to the wild-type amino acid sequence of the naturally occurring protein.

An amino acid sequence derived from the sequence of a naturally-occurring protein preferably has at least 70%, at least 80%, at least 90%, or at least 95% amino acid identity with at least twenty, at least thirty, at least forty, at least fifty, at least sixty, at least seventy, or at least eighty contiguous amino acids of the naturally occurring protein.

In certain exemplary embodiments, a protein selectively labeled on a first amino acid is a recombinant protein made from a nucleic acid construct, and one or more codons for one or more non-target amino acids is mutated or deleted from the nucleic acid sequence of the construct encoding the amino acid sequence with homology to an amino acid sequence of a naturally-occurring protein. For example, an engineered protein to be used for making pre-labeled protein standards can have one or more copies of an amino acid sequence with at least 70% or at least 80% identity with at least 20, at least 30, at least 40, or at least 50 contiguous amino acids of a thioredoxin sequence, in which lysine has been removed from the sequence by deletion or mutation of lysine codons in the nucleic acid sequence encoding the protein. Lysine codons can be mutated to any nonlysine codons. In some instances, one or more lysine codons is mutated to a nonlysine codon based on the hydrophilicity, charge, or reactivity of the nonlysine amino acid to optimize properties such as solubility or purification of the labeled protein.

The invention provides molecular weight standard sets in which two or more selectively labeled proteins of different molecular weights comprise different numbers of copies of an amino acid sequence having homology to an amino acid sequence of a naturally-occurring protein. For example, a standard set can have proteins selectively labeled on a target amino acid having two, three, four, five, six, seven, eight, nine, ten, eleven, twelve, thirteen, fourteen, fifteen, sixteen, seventeen, eighteen, nineteen, twenty, or more copies of an amino acid sequence that is at least 70% or at least 80% identical to at least 20, at least 30, at least 40, or at least 50 contiguous amino acids of a naturally-occurring protein which lack residues of a non-target amino acid that are present in the wild-type protein sequence.

A naturally-occurring protein can be any naturally-occurring protein. Nucleotide-disulfide oxidoreductases are highly soluble proteins (an advantage for accessibility of residues for labeling) having an abundance of cysteine residues. Examples of nucleotide-disulfide oxidoreductases include lipoamide dehydrogenase, glutathione reductase, or thioredoxin. All or a portion of the amino acid sequence of a lipoamide dehydrogenase, glutathione reductase, or thioredoxin can be incorporated into a protein for use as a pre-labeled protein standard that is selectively labeled on cysteine. A lipoamide dehydrogenase, glutathione reductase, and/or thioredoxin whose sequence is used for engineering a pre-labeled protein standard can be from a prokaryotic or eukaryotic source. An nucleotide-disulfide oxidoreductases can be, as nonlimiting examples, any of SEQ ID NO:1 (*E. coli* thioredoxin), SEQ ID NO:2 (human thioredoxin), SEQ ID NO:3 (*E. coli* glutaredoxin 1), SEQ ID NO:3 (*E. coli* glutaredoxin 2), SEQ ID NO:5 (*E. coli* glutathione oxidoreductase), SEQ ID NO:6 (human glutathione oxidoreductase), SEQ ID NO:7 (*E. coli* lipoamide dehydrogenase), SEQ ID NO:8 (human lipoamide dehydrogenase), their variants, their analogues in other species, and variants of such analogues.

In some preferred embodiments of the invention, a protein used as a pre-labeled molecular weight standard includes one or more copies of an amino acid sequence derived from a lipoamide dehydrogenase, glutathione reductase, and/or thioredoxin sequence. In some preferred embodiments of the invention, a protein used as a pre-labeled molecular weight standard includes one or more copies of an amino acid sequence derived from a thioredoxin sequence. In some preferred embodiments of the invention, a protein used as a pre-labeled molecular weight standard includes one or more copies of an amino acid sequence derived from a bacterial thioredoxin sequence, such as an *E. coli* thioredoxin sequence, and can be a low molecular weight thioredoxin, such as a sequence encoded by TrxA.

All or a portion of a thioredoxin sequence can be used in making one or more pre-labeled protein standards. For example, a thioredoxin sequence used in a protein standard can have a truncation of from one to 50 amino acids from the carboxy terminus, such as, for example, from one to ten, from ten to twenty, form twenty to thirty, form thirty or forty, or from forty to fifty, amino acids can be truncated from the carboxy terminus. In some preferred embodiments, 22 amino acids are truncated from the end of a thioredoxin sequence, such as a bacterial thioredoxin sequence used as a sequence in a protein standard. In some preferred embodiments, from 39-41 amino acids are truncated from the end of a thioredoxin sequence, such as a bacterial thioredoxin sequence used as a sequence in a protein standard.

In some embodiments, a protein of a pre-labeled protein standard set that is selectively labeled on cysteine comprises an amino acid sequence derived from an nucleotide-disulfide oxidoreductase, such as a lipoamide dehydrogenase, a glutathione reductase, or a thioredoxin. In some preferred embodiments, an amino acid sequence is derived from a thioredoxin sequence, having at least 70% or at least 80% identity with the amino acid sequence of at least 20, at least 30, at least 40 or at least 50 amino acids of a thioredoxin, such as a truncated thioredoxin. In some preferred embodiments, an amino acid sequence derived from a thioredoxin sequence differs from the naturally-occurring thioredoxin sequence by lacking lysine residues. In some preferred embodiments, a selectively labeled pre-labeled protein standard is devoid of lysine residues and is labeled on one or more cysteine residues, and comprises one or more copies of an amino acid sequence derived from a thioredoxin. In preferred embodiments, the protein is made from a nucleic acid construct that includes a nucleic acid sequence encoding one or more copies of an amino acid sequence derived from a naturally-occurring thioredoxin sequence, in which the nucleic acid sequence has been mutated to delete one or more lysine codons or to change one or more lysine codons to non-lysine codons.

In some aspects of the invention, a pre-labeled protein standard set can include one or more copies of an amino acid sequence having at least 70% or at least 80% identity to at least 20, at least 30, at least 40, or at least 50 contiguous amino acids of a naturally-occurring protein in which the amino acid sequence comprises one or more amino acid changes that alter the number or spacing of a first amino acid targeted for labeling.

Additional target amino acid codons can be added to a nucleic acid sequence that encodes a protein standard of the invention. In a preferred embodiment, one or more additional cysteine codons is added to a nucleic acid sequence encoding a truncated thioredoxin. Two, three, four, five, six, seven, eight, nine, ten, eleven, twelve, thirteen, fourteen, fifteen, sixteen, seventeen, eighteen, nineteen, twenty, or more copies of the nucleic acid sequence encoding a truncated thioredoxin can be assembled together to make a recombinant protein having multiple copies of a truncated thioredoxin sequence. In some embodiments, the recombinant nucleic acid constructs used to produce the protein standards are further mutated to allow alternate codon usage for the same amino acid from copy to copy to reduce the risk of genetic recombination.

Pre-Labeled Proteins Having Consistent Ratios of a First Amino Acid to Molecular Weight In some preferred embodiments of the invention, a pre-labeled protein standard set includes two or more proteins of different molecular weights labeled on a target amino acid, in which the ratios of the number of residues of the target amino acid to molecular weight of two or more of the selectively labeled proteins are within 5% of one another, in some embodiments within 2.5% of one another. For example, the ratio of the number of residues of a target amino acid to molecular weight may be 4 residues per 10 kDa, or 0.4 residues of first amino acid/kDa for a first protein of a standard set, and can be, for example, between 0.38 and 0.42 residues of target amino acid/kDa for a second protein of a standard set, where the first and second proteins have ratios of the number of target amino acid residues to molecular weight that are within 5% of one another.

In some preferred embodiments, the two or more labeled proteins that have a consistent ratio of the number of residues of a first, or target, amino acid to molecular weight of the proteins are selectively labeled on a first amino acid. In some preferred embodiments, the two or more labeled proteins are selectively labeled on a first amino acid and comprise one or more copies of an amino acid sequence of a naturally-occurring protein or having at least 70% or at least 80% identical to at least 20, at least 30, at least 40, or at least 50 contiguous amino acids of a naturally-occurring protein. In some preferred embodiments, the two or more labeled proteins are comprise a labeling compound bound to a first amino acid and comprise one or more copies of an amino acid sequence of or having homology to an amino acid sequence of a naturally-occurring protein, in which the amino acid sequences of the labeled proteins lacks residues of a second amino acid that can react with the labeling compound. The invention provides pre-labeled protein standard sets that comprise a plurality of labeled proteins, in which two or more of the labeled proteins are selectively labeled on a first amino acid with a labeling compound and lack residues of a second amino acid that is capable of reacting with the labeling compound, in which the ratios of the number of residues of the first amino acid to molecular weight of the two or more selectively labeled proteins are within 5%, 2.5%, or 1% of one another.

In some aspects of a pre-labeled protein standard set, the set comprises a plurality of labeled proteins, and at least two proteins of the set are labeled on a target amino acid and have an average of between one and ten residues of the target amino acid per 10 kDa, such as an average of between two and seven residues of the target amino acid, such as an average of between three and five residues of the target amino acid, such as an average of between 3.5 and 4.5 residues of the target amino acid per 10 kDa. Preferably, in these embodiments, the two or more proteins labeled on a target amino acid are selectively labeled with a labeling compound on the target amino acid. In exemplary embodiments, the selectively labeled protein lacks residues of a non-target amino acid capable of reacting with the dye. In some preferred embodiments, a pre-labeled protein standard set comprises at least five labeled proteins, in which three, four, five, six, seven, eight, nine, ten, eleven, twelve, thirteen, fourteen, fifteen, sixteen, seventeen, eighteen, nineteen, twenty, or more of the proteins are selectively labeled on a target (first) amino acid, and have an average of between one and ten residues of the target amino acid per 10 kDa, such as an average of between two and seven residues of the target amino acid, such as an average of between three and five residues of the target amino acid, such as an average of between 3.5 and 4.5 residues of the target amino acid per 10 kDa.

In some preferred embodiments, a pre-labeled protein standard set comprises at least five labeled proteins, in which three, four, five, six, seven, eight, nine, ten, eleven, twelve, thirteen, fourteen, fifteen, sixteen, seventeen, eighteen, nineteen, twenty, or more of the proteins are labeled on cysteine, and have an average of between three and five cysteine residues, such as an average of between 3.5 and 4.5 cysteine residues per 10 kDa. In some preferred embodiments, a pre-labeled protein standard set comprises at least five labeled proteins, in which three, four, five, six, seven, eight, nine, ten, eleven, twelve, thirteen, fourteen, fifteen, sixteen, seventeen, eighteen, nineteen, twenty, or more of the proteins lack lysine and are labeled on cysteine, and have an average of between three and five residues of cysteine, such as between 3.5 and 4.5 residues of cysteine, per 10 kDa.

Proteins of a pre-labeled protein standard set that are labeled with a labeling compound on a target amino acid and have ratios of the number of residues of the target amino acid to molecular weight that are within 5% of one another can have molecular weights that differ from one another by at least 10 kDa, at least 20 kDa, at least 30 kDa, at least 40 kDa, at least 50 kDa, at least 60 kDa, at least 70 kDa, at least 80 kDa, at least 90 kDa, at least 100 kDa, at least 110 kDa, or at least 150 kDa, where the given molecular weights are plus or minus 1 kDa. Proteins of a pre-labeled protein standard set that are labeled with a dye on a target amino acid and have ratios of the number of residues of the target amino acid to molecular weight that are within 5% of one another can be labeled with the same dye, or with different dyes.

The invention provides in a further aspect a pre-labeled protein standard set that comprise a plurality of labeled proteins span a molecular weight range of from 10 kDa or less to 100 kDa or greater, in which two, three, four, five or more of the plurality of labeled proteins are selectively labeled with a dye on a first amino acid and have ratios of a first amino acid to molecular weight that are within 5% of one another, in which the migration of the five or more pre-labeled protein standards in acrylamide gel electrophoresis under denaturing conditions does not differ substantially from the migration of the same set of proteins in unlabeled form. In preferred embodiments, each of the five or more labeled protein standards that has a molecular weight of 10 kDa or greater migrates within 5% of each of the five or more proteins in unlabeled form on the same acrylamide gels.

A pre-labeled protein standard set of the invention can include two, three, four, five, six, seven, eight, nine, ten, eleven, twelve, thirteen, fourteen, fifteen, sixteen, seventeen, eighteen, nineteen, twenty, or more labeled proteins. For example, pre-labeled protein standard sets can have between ten and fifteen, between fifteen and twenty, twenty or more, thirty or more, forty or more, fifty or more sixty or more, seventy or more, eighty or more, ninety or more, or one hundred or more labeled proteins. All or a subset of the labeled proteins of a pre-labeled protein standard set can be selectively labeled. Two or more of the labeled proteins of a pre-labeled protein standard set can comprise a labeling compound on a target amino acid and have ratios of the number of residues of the target amino acid to molecular weight that are within 5% of one another. A pre-labeled protein standard set of the invention can include two, three, four, five, six, seven, eight, nine, ten, eleven, twelve, thirteen, fourteen, fifteen, or more proteins selectively labeled on a target amino acid.

In some preferred embodiments, a pre-labeled standard set comprises a plurality of labeled proteins, in which at least two of the proteins are selectively labeled on a target amino acid, and the at least two proteins selectively labeled on a target amino acid have ratios of the number of target amino acid residues to molecular weight that are within 5% of one another.

As a nonlimiting example, a pre-labeled protein standard set can comprise from five to twenty labeled proteins, of which from one to twenty are labeled on cysteine and lack lysine residues. As a nonlimiting example, a pre-labeled protein standard set can comprise from five to twenty labeled proteins, of which from two to twenty comprise a label on cysteine residues and lack lysine residues, and have ratios of cysteine residue number to molecular weight that are within 5% of one another.

Highly Resolving Electrophoretic Separation of Pre-labeled Protein Standards

Preventing the reaction of a labeling compound with a non-target amino acid can reduce the inconsistency in labeling of a protein. For example, labeling of a particular protein with a dye that has high specificity for a first amino acid and reduced specificity for a second amino acid can result in a population of labeled protein variants, in which the variants are predominantly labeled on the first amino acid, but vary in the degree of labeling of the second amino acid that is present on the protein. Such variability in the population of labeled protein results in a range of masses for the particular labeled protein, depending on the range in the amount of dye molecules attached to the protein. This leads to a protein standard having variable label intensity per microgram of protein, and poor resolution of the protein standard in separation techniques that rely on mass, such as, but not limited to, electrophoresis and chromatography.

The present invention provides protein standards that are pre-labeled that separate based on size, charge, or a combination of size and charge, distinctly and consistently. Pre-labeled standards are labeled prior to separation or experimental procedures, and can be observed during or after separation procedures without performing additional steps required to stain the proteins in the midst of or at the conclusion of a separation or experimental procedure. Pre-labeled protein standards can be used in protein separation techniques such as, but not limited to, isolelectric focusing in semi-solid (e.g. gel) or liquid media; chromatography, including chromatographic separation based on size, charge, or a combination thereof, including HPLC and FPLC; and electrophoresis, including, without limitation, capillary electrophoresis, free-flow electrophoresis, non-denaturing (native) gel electrophoresis and denaturing gel electrophoresis, mass spectrometry, and chromatofocusing. In some preferred aspects, the present invention provides protein molecular weight standards that are selectively labeled, such that attachment of a dye to an amino acid that is not targeted for labeling (a non-target amino acid) is restricted. The invention additionally provides sets of pre-labeled protein standards that can be used as molecular weight markers in biochemical separations, in which at least one labeled protein of the sets is selectively labeled on a first amino acid.

The pre-labeled protein standards of the present invention are particularly useful in gel electrophoresis, in which molecular weights can be determined using the pre-labeled standards run alongside one or more sample proteins. For example, pre-labeled standards provided herein can be used as markers in Blue Native gel electrophoresis, in which non-denatured proteins are separated based on size (described in Schagger H and von Jagow G (1991) Anal. Biochem. 199: 223-231; Schagger H, Cramer W A, and von Jagow G (1994) Anal. Biochem. 217: 220-230; and Schagger H (2001) Methods Cell Biol. 65: 231-244), or can be used in denaturing gel electrophoresis, such as denaturing polyacrylamide gel electrophoresis in which proteins are denatured using urea, formamide, or one or more denaturing detergents, such as, but not limited to, sodium dodecyl sulfate (SDS) or lithium dodecyl sulfate (LDS). In some preferred embodiments, proteins standards are used in denaturing acrylamide gel electrophoresis in which proteins are denatured using a detergent, such as but not limited to SDS or LDS. Many denaturing polyacrylamide gel electrophoresis systems are known in the art, such as, for example, Bis-Tris gels, Tris-tricine gels, Tris-acetate gels, or Tris-glycine gels. Gels for electrophoretic separation of proteins are available commercially, for example, NuPAGE® Novex® Tris-Acetate gels, NuPAGE® Novex® Bis-Tris gels, Novex® Tricine gels, and Novex® Tris-Glycine gels, all available from Invitrogen Corp., Carlsbad, Calif. The invention provides pre-labeled protein standards that can be used as molecular weight markers, in which the pre-labeled protein standards produce sharp bands on electrophoresis gels, such as electrophoresis gels run under denaturing conditions, and the migration of the pre-labeled protein standards are substantially the same as the migration of their unlabeled counterparts.

Migration of labeled and unlabeled forms of a protein can be compared, for example, on Bis-Tris acrylamide gels using MOPS or MES buffer, or on Tris-acetate, Tricine, or Tris-glycine acrylamide gels, under electrophoresis conditions in which a the loading dye front migrates at least 5 cm from the loading site and migration of a protein calculated to be about 10 kDa and the migration of a protein calculated to be about 80 kDa are at least 3.5 cm apart at the completion of electrophoresis. The gels can be "mini gels" having lengths of 10 cm or less, such as, for example, gels 8 cm in length, or can be more than 10 cm in length, for example 12 cm, 15, cm, 20 cm or greater in length, in which the dye front at the end of the electrophoresis period has migrated at least 80% the length of the gel. The dye front can be a Coomassie dye front, such as a Coomassie G250 dye front.

For example, to test the consistency of migration between a labeled protein standard and its unlabeled counterpart, electrophoresis can be performed on a polyacrylamide gel, having a length of 8 cm, in which at the end of electrophoresis the dye front of the gel has migrated at least 5 cm, such as at least 6 cm, such as at least 6.5 cm, such as about 6.8 cm, from the loading site. The dye front can be a Coomassie dye front, such as a Coomassie G250 dye front.

For example, 4-12% NuPAGE® Bis-Tris acrylamide 8 cm×8 cm gels using MOPS or MES buffer, or 4-20% Tris-glycine 8 cm×8 cm acrylamide gels available from Invitrogen (Carlsbad, Calif.) can be used to determine migration properties of labeled and unlabeled protein standards using electrophoresis conditions provided in the manufacturer's manual for separating proteins. Migration of selectively labeled and unlabeled forms of a protein are compared under electrophoresis conditions in which a the loading dye front migrates at least 5 cm from the loading site and migration of a protein calculated to be about 10 kDa and the migration of a protein calculated to about 80 kDa are at least 3 cm apart at the completion of electrophoresis. Migration of selectively labeled and unlabeled forms of a protein are preferably compared under electrophoresis conditions in which a the loading dye front migrates at least 6 cm from the loading site and migration of a protein calculated to be about 10 kDa and the migration of a protein calculated to about 80 kDa are at least 3.5 cm apart at the completion of electrophoresis. Migration of selectively labeled and unlabeled forms of a protein are preferably compared under electrophoresis conditions in which a the loading dye front migrates at least 6.5 cm from the loading site and migration of a protein calculated to be about 10 kDa and the migration of a protein calculated to about 80 kDa are at least 3.5 cm apart at the completion of electrophoresis. The dye front can be a Coomassie dye front, such as a Coomassie G250 dye front.

Preferably, the calculated molecular weights for a pre-labeled protein standard having a molecular weight greater than 5 kDa and its unlabeled counterpart on one of the referenced denaturing acrylamide gels are within 10%, 7%, or 5% of one another.

The invention provides pre-labeled protein standard sets having five or more labeled proteins of different molecular weights, in which all of the pre-labeled proteins having a molecular weight of greater than 3.5 kDa (such as, for example, having a molecular weight of greater than 5 kDa, such as, for example, having a molecular weight of 10 kDa or greater) have substantially the same migration on electrophoresis gels as their unlabeled counterparts.

The invention provides sets of pre-labeled protein standards having at least ten, at least eleven, at least twelve, or at least fifteen pre-labeled proteins of different molecular weights, in which all of the pre-labeled proteins of the sets having a molecular weight of greater than 3.5 kDa, greater than 5 kDa, or 10 kDa or greater, migrate on electrophoresis gels, such as for example Bis-Tris gels and Tris-glycine gels as they are known in the art, within 10%, 7%, or 5% of the migration unlabeled counterparts.

The invention provides individual pre-labeled proteins that migrate within 10%, within 7%, within 5%, within 4%, within 2.5%, within 2%, within 1.5%, or within 1% of the migration distance of the same proteins that are not labeled.

The invention provides pre-labeled protein molecular weight standard sets in which all the proteins of the set having a molecular weight of greater than or equal to 3.5 kDa migrate within 5% of the migration distance of the same proteins that are not labeled. The invention provides protein molecular weight standard sets in which all the proteins of the set having a molecular weight of greater than or equal to 5 kDa migrate within 5% of the migration distance of the same proteins that are not labeled. The invention provides protein molecular weight standard sets in which all the proteins of the set having a molecular weight of 10 kDa or greater migrate within 5% of the migration distance of the same proteins that are not labeled.

The invention provides pre-labeled protein molecular weight standard sets in which all the proteins of the set having a molecular weight of greater than or equal to 3.5 kDa migrate within 4%, within 2.5%, within 2%, within 1.5%, or within 1% of the migration distance of the same proteins that are not labeled under standard protein gel electrophoresis conditions on a 4-12% Bis-Tris gel or a 4-20% Tris-glycine gel. The invention provides pre-labeled protein molecular weight standard sets in which all the proteins of the set having a molecular weight of greater than or equal to 5 kDa migrate within 4%, within 2.5%, within 2%, within 1.5%, or within 1% of the migration distance of the same proteins that are not labeled. The invention provides pre-labeled protein molecular weight standard sets in which all the proteins of the set having a molecular weight of 10 kDa or greater migrate within 4%, within 2.5%, within 2%, within 1.5%, or within 1% of the migration distance of the same proteins that are not labeled.

The invention further provides pre-labeled protein molecular weight standard sets in which all the proteins of the set having a molecular weight of greater than 3.5 kDa, greater than 5 kDa, or greater than or equal to 10 kDa, migrate within 4%, within 2.5%, within 2%, within 1.5%, or within 1% of the migration distance of the same proteins that are not labeled.

In some aspects of the invention, a pre-labeled protein standard set comprises from two to twenty proteins, in which two or more of the proteins are selectively labeled, such that when the a pre-labeled protein standard set is electrophoresed on a denaturing acrylamide gel, such as an 8 cm long Bis-Tris gel run with MES electrophoresis buffer (for example, a 4-12% Bis-Tris 8×8 cm gel, Invitrogen, Carlsbad, Calif.), the widths of bands from proteins having a molecular weight of greater than or equal to 10 kDa differ by less than 2-fold. In some embodiments, pre-labeled protein standard set comprises labeled proteins ranging in size from 10 kDa or less to 100 kDa or more, and the width of visible bands visible to the naked eye from proteins having a molecular weight of at least 10 kDa to 100 kDa or more differ in width by less than 50%, less than 40%, or less than 30%. The width of bands visible to the naked eye from proteins having a molecular weight of at least 20 kDa to less than 100 kDa can differ in width by 15% or less. A pre-labeled standard set of the invention can include at least 6 proteins comprising at least four different dyes having different colors having a molecular weight of at least 20 kDa to less than 100 kDa, in which the width of the bands visible to the naked eye of the electrophoresed proteins differ by less than 15%. A pre-labeled standard set include 5 proteins in which the width of bands visible to the naked eye of the electrophoresed proteins difference by 3 or less. A pre-labeled standard set include 5 proteins labeled with at least four different dyes of different colors, in which the width of bands visible to the naked eye of the electrophoresed proteins difference by 3% or less.

In one embodiment, a pre-labeled protein standard set includes 6 proteins stained with four different dyes having distinguishably different colors, in which the proteins have a molecular weight of at least 20 kDa to less than 100 kDa, in which the width of bands of the electrophoresed proteins difference by less than 15%. In another embodiment, a pre-labeled protein standard set includes 5 proteins stained with four different dyes having distinguishably different colors, in which the proteins have a molecular weight of from about 20 kDa to about 80 kDa, in which the molecular weights differ of the 5 proteins differ by equal increments, in which the width of bands of the electrophoresed proteins differ by 3% or less.

Pre-Labeled Protein Standard Sets

The invention provides in a further aspect a pre-labeled protein standard set that comprises five or more labeled protein standards that span a molecular weight range of from 10 kDa or less to 100 kDa or greater, in which the migration of the five or more labeled protein standards in denaturing acrylamide gel electrophoresis does not differ substantially from the migration of the same set of proteins in unlabeled form. In preferred embodiments, the electrophoretic migration of each of the five or more labeled protein standards that have a molecular weight of 10 kDa or greater is within 5% of the electrophoretic migration of each of the five or more labeled protein standards calculated from the same acrylamide gels. In some embodiments, a pre-labeled protein standard set includes five, six, seven, eight, nine, ten, eleven, twelve or more labeled proteins, in which the labeled proteins span a molecular weight range of from 10 kDa or less to at least 100 kDa, in which electrophoretic migration on acrylamide gels of each of the five or more labeled protein standards having a molecular weight of 10 kDa or greater is within 5% of the electrophoretic migration of each of the five or more protein standards in unlabeled form on the same acrylamide gels.

In some embodiments, a pre-labeled protein standard set includes at least ten labeled proteins spanning a molecular weight range of from 10 kDa or less to 250 kDa or greater, in which the electrophoretic migration of each of the labeled protein standards having a molecular weight of 10 kDa or greater is within 5% of the electrophoretic migration of each of the protein standards in unlabeled form. In some embodiments, a pre-labeled protein standard set includes at least ten labeled proteins spanning a molecular weight range of from 10 kDa or less to 250 kDa or greater, in which the electrophoretic migration of 90% of the labeled protein standards having a molecular weight of 10 kDa or greater is within 4% of the electrophoretic migration of each of the protein standards in unlabeled form. In some embodiments, a pre-labeled protein standard set includes at least ten labeled proteins spanning a molecular weight range of from 10 kDa or less to 250 kDa or greater, in which the electrophoretic migration of 70% of the labeled protein standards having a molecular weight of 10 kDa or greater is within 3% of the electrophoretic migration of each of the protein standards in unlabeled form. In some embodiments, a pre-labeled protein standard set includes at least ten labeled proteins spanning a molecular weight range of from 10 kDa or less to 250 kDa or greater, in which the electrophoretic migration of 70% of the labeled protein standards having a molecular weight of 10 kDa or greater is within 2.5% of the electrophoretic migration of each of the protein standards in unlabeled form. In some embodiments, a pre-labeled protein standard set includes at least ten labeled proteins spanning a molecular weight range of from 10 kDa or less to 250 kDa or greater, in which the electrophoretic migration of 70% of the labeled protein standards having a molecular weight of 10 kDa or greater is within 2% of the electrophoretic migration of each of the protein standards in unlabeled form.

The pre-labeled protein molecular weight standard sets can comprise two, three, four, five, six, seven, eight, nine, ten, eleven, twelve, thirteen, fourteen, fifteen, or more labeled proteins. For example, pre-labeled protein standard sets can have between ten and fifteen, between fifteen and twenty, twenty or more, thirty or more, forty or more, fifty or more sixty or more, seventy or more, eighty or more, ninety or more, or one hundred or more labeled proteins. Any or all of the of the proteins of a pre-labeled protein molecular weight standard set can be selectively labeled. For example, a pre-labeled protein molecular weight standard sets can comprise two, three, four, five, six, seven, eight, nine, ten, eleven, twelve, thirteen, fourteen, fifteen, or more labeled proteins, of which one, two, three, four, five, six, seven, eight, nine, ten, eleven, twelve, thirteen, fourteen, fifteen, or more are selectively labeled on a target amino acid. A pre-labeled protein molecular weight standard sets can comprise between ten and fifteen, between fifteen and twenty, twenty or more, thirty or more, forty or more, fifty or more sixty or more, seventy or more, eighty or more, ninety or more, or one hundred or more labeled proteins, of which between ten and fifteen, between fifteen and twenty, twenty or more, thirty or more, forty or more, fifty or more sixty or more, seventy or more, eighty or more, ninety or more, or one hundred or more are selectively labeled on a target amino acid.

In some embodiments of these aspects, one, two, three, four, five, or more than five labeled proteins of a protein standard set having molecular weights of 10 kDa or more are selectively labeled on a target amino acid and migrate substantially the same as their unlabeled counterparts. In some embodiments, one, two, three, four, five, or more than five labeled proteins of the protein standard set are selectively labeled on lysine and lack cysteine residues. In some embodiments of this aspect, one, two, three, four, five, or more than five labeled proteins of the protein standard set are selectively labeled on cysteine and lack lysine residues.

In other examples, a pre-labeled protein standard set can comprise from two to twenty labeled proteins, of which from one to twenty are labeled on lysine and lack cysteine residues, and, optionally, additionally lack one or more of one or more histidine residues, one or more tryptophan residues, or one or more tyrosine residues. In another example, a pre-labeled protein standard set can comprise from five to twenty labeled proteins, of which from two to twenty are labeled on lysine and lack cysteine residues, and, optionally, additionally lack one or more of one or more histidine residues, tryptophan residues, or one or more tyrosine residues, and have ratios of lysine residue number to molecular weight that are within 5% of one another.

Different proteins of a pre-labeled protein standard set can be labeled on different amino acids. Different proteins of a pre-labeled protein standard set can be labeled with different dyes having different colors, such that two or more protein bands can be distinguished by color when the proteins of the standard set are separated, such as on a gel. For example, two, three, four, or more different dyes can be used, such that one or more of the labeled proteins are labeled with a first dye and one or more of the labeled proteins are labeled with a second dye; or such that one or more of the labeled proteins are labeled with a first dye, one or more of the labeled proteins are labeled with a second dye, and one or more of the labeled proteins are labeled with a third dye; or such that one or more of the labeled proteins are labeled with a first dye, one or more of the labeled proteins are labeled with a second dye, one or more of the labeled proteins are labeled with a third dye, and one or more of the labeled proteins are labeled with a fourth dye, etc. Where multiple dyes are used to label proteins of a pre-labeled protein standard set, one, two, three, four, or more pre-labeled proteins of the set can be labeled with the same dye.

In some embodiments, pre-labeled protein standard set of the invention can span any molecular weight range, but in preferred embodiments spans a molecular weight range of from 10 kDa or less to 100 kDa or greater, or from 10 kDa or less to 150 kDa or greater, or from 5 kDa or less to 150 kDa or greater, or from 10 kDa or less to 200 kDa or greater, or from 5 kDa or less to 200 kDa or greater, or from 10 kDa or less to 250 kDa or greater, or from 5 kDa or less to 250 kDa or greater.

In some aspects of the invention, a pre-labeled protein standard set of the invention includes three or more labeled proteins, in which a first and a second protein of the three or more labeled proteins differ from one another by the same molecular weight increment as a second and third protein of the set. In some embodiments, the molecular weight increment, +/−1 kDa, is a multiple of a value between 5 kDa, a multiple of a value between 10 kDa, a multiple of a value between 20 kDa, or a multiple of 50 kDa. In some preferred embodiments, a pre-labeled protein standard set of the invention includes four or more labeled proteins, in which at least four of the four or more labeled proteins differ from one another by a multiple of (plus or minus 1.0 kDa) 10 kDa. In some preferred embodiments, a pre-labeled protein standard set of the invention includes five or more labeled proteins, in which at least five of the five or more labeled proteins differ from one another by a multiple of 10 kDa. In some preferred embodiments, a pre-labeled protein standard set of the invention includes five or more labeled proteins, in which at least 40% of the five or more labeled proteins differ from one another by a multiple of 10 kDa.

A pre-labeled protein of a standard set of the invention can be made by recombinant methods. Protein standards can be produced in cell culture and purified for selective labeling on one or more target nucleic acids. In some embodiments, the proteins standards have amino acid tag sequences, such as amino acid tags that can be used to purify the proteins. An exemplary amino acid tag is a His tag. Proteins made by recombinant methods can be based on the sequences of naturally-occurring proteins, or can have synthetically designed sequences.

In some aspects, a pre-labeled protein standard set can include one or more proteins not made by recombinant methods. Labeled proteins of a pre-labeled protein standard set isolated from natural sources, such as organisms, cells, or media, can be enzymatically or chemically modified, such as by addition of chemical protecting groups, or fragmentation by chemical or enzymatic cleavage, or can be unmodified. In some aspects, a pre-labeled protein standard set can include one or more proteins made, at least in part, by synthetic methods, such as chemical synthesis.

A pre-labeled protein standard set can include one or more proteins that is not selectively labeled. Labeled proteins of a pre-labeled protein standard set on the invention that are not selectively labeled can be recombinant proteins or proteins isolated from cells, tissues, organisms, biological samples, or media. Proteins can also be made wholly or partly using chemical synthesis.

The invention also includes a set of pre-labeled protein standards that comprises a plurality of labeled proteins, in which one or more of the labeled proteins is selectively labeled on a first amino acid, in which the plurality of labeled proteins are provided in one or more solutions. In preferred embodiments, a pre-labeled protein standard set provided in solution form comprises at least five labeled proteins, in which two, three, four, or five of the labeled proteins are labeled on cysteine and lack lysine. The invention also includes a pre-labeled protein standard set provided in solution form comprises at least 12 labeled proteins, in which the labeled proteins span a molecular weight range of from 10 kDa or less to 100 kDa or greater, in which the electrophoretic migration of each of the pre-labeled protein standards having a molecular weight of 5 kDa or greater is within 5% of the electrophoretic migration of each of the same five or more protein standards in unlabeled form, calculated from the same acrylamide gel. A solution can include one or more buffers, reducing agents, chelators, alcohols, detergents, or dyes.

Also provided herein is a set of unlabeled protein standards that includes at least two proteins that comprises one or more copies of a sequence derived from a naturally-occurring protein, in which the protein lacks residues of a first amino acid. In some preferred embodiments, the set of unlabeled protein standards comprises two or more proteins that comprise two or more copies of a sequence derived from a naturally-occurring protein, in which the two or more labeled proteins lack lysine residues. In some preferred embodiments, the set of pre-labeled protein standards comprises three or more, four or more, or five or more, six or more seven or more, eight or more, nine or more, ten or more, eleven or more, or twelve or more labeled protein standards in which two or more, three or more, four or more, five or more of the proteins lack lysine and comprise two or more copies of a sequence derived from a naturally-occurring protein. The standards can be labeled with two, three, four, or more visually distinguishable dyes. The standards can span a molecular weight range of from less than 10 kDa to greater than 100 kDa, or from less than 5 kDa to greater than 250 kDa. The standards can have two or more, three or more, four or more, five or more, or six or more protein standards that differ by an increment that is a multiple of 10 kDa (plus or minus 1 kDa). In some embodiments, the ratios of cysteine residues to molecule weight for the two or more, three or more, four or more, five or more proteins that lack lysine do not vary by more than 5%. In some embodiments, each of the two or more, three or more, four or more, five or more proteins that lack lysine have between one and ten, between two and seven, or between three and five cysteine residues per 10 kDa.

Methods of Using a Pre-Labeled Standard Set to Determine Molecular Weight of a Protein The invention also includes methods for separating two or more protein standards of a set of pre-labeled protein standards, in which the pre-labeled protein standard set includes at least one protein that is selectively labeled on a first amino acid and is depleted in residues of a second amino acid. In some embodiments of the method, the one or more selectively labeled protein standards The method includes applying the pre-labeled protein standard set to an electrophoresis gel, applying an electric field across the gel, and separating two or more protein standards of the pre-labeled protein standard set. The two or more protein standards are separated such that their bands do not overlap. In preferred embodiments, all of the protein standards of the pre-labeled standard set are separated such that the bands do not overlap and such that the width of the bands on a gel of each of the electrophoresed proteins of the set having a molecular weight of 10 kDa or greater does not vary by more than 2-fold. In preferred embodiments, all of the protein standards of the pre-labeled standard set are separated such that the bands do not overlap the width of the bands on a gel of each of the electrophoresed proteins of the set having a molecular weight of 10 kDa or greater does not vary by more than 2-fold and the band intensities of the proteins of the pre-labeled protein standard set having molecular weights of 10 kDa or greater does not vary by more than 2.5 fold. In preferred embodiments, protein standards of the prelabeled standard set having molecular weights of 10 kDa or greater migrate within 5% of the distance of the that the same protein standards in unlabeled form migrate.

In a further aspect, methods are provided for characterizing one or more sample proteins using a pre-labeled protein standard set provided herein. The method includes electrophoresing one or more proteins and at least one prelabeled protein standard set as described herein in a gel; and comparing the migration of the one or more proteins with the migration of least one protein standard of the pre-labeled standard set. In some preferred embodiments, the method further comprises determining the molecular weight of the one or more sample proteins.

For example, the method includes electrophoresing a sample that includes one or more proteins in a first lane of a gel and electrophoresing a pre-labeled protein standard set that comprises at least two labeled proteins that are selectively labeled on a first amino acid in a second lane of the gel, determining the migration distance of at least two of the two or more labeled proteins of the standard, determining the migration distance of at least one of the one or more sample proteins, and calculating the molecular weight of the at least one sample protein based on the migration distance and molecular weights of the at least two labeled proteins of the standard. The method can use point-to point calibration or can compare migration distances by generating a curve based on migration distance versus molecular weight (or log of molecular weight), for example using the least squares method.

In preferred embodiments, all of the protein standards of the pre-labeled standard set are separated from one another such that the bands do not overlap and such that the widths of the bands on a gel of each of the electrophoresed proteins of the set having a molecular weight of 10 kDa or greater do not vary by more than 2-fold. In preferred embodiments, all of the protein standards of the pre-labeled standard set are separated such that the bands do not overlap the widths of the bands on a gel of each of the electrophoresed proteins of the set having a molecular weight of 10 kDa or greater do not vary by more than 2-fold and the band intensities of the proteins of the pre-labeled protein standard set having molecular weights of 10 kDa or greater do not vary by more than 2.5 fold. In preferred embodiments, protein standards of the prelabeled standard set having molecular weights of 10 kDa or greater migrate within 5% of the distance of the that the same protein standards in unlabeled form migrate.

Pre-Labeled Protein Standard Kits

The invention also includes kits that include the described pre-labeled protein standard sets, and further comprise one or more of one or more buffers, loading dyes, reducing agents, unlabeled protein standards, blotting membranes, gel cassettes, pre-cast gels, or electrophoresis buffers. The components of the kit can in one or more containers, and two or more of the components of the kit can be provided in a common package (such as, for example, a box, rack, or jar). The kit can also include instructions for use, or instructions for accessing protocols for use of the kit or its components via the internet.

The set of pre-labeled protein standards of the kit can be provided as lyophilized solids, or in solution in liquid or frozen form. A solution comprising one or more labeled protein standards of a set can include one or more buffers, reducing agents, chelators, alcohols, detergents, or dyes. The set of pre-labeled protein standards of the kit can include at five, six, seven, eight, nine, ten, eleven, twelve, or more labeled protein standards that are provided as one or more mixtures of two or more labeled standards. In some embodiments, all of the proteins of a pre-labeled protein standard set are provided in a single mixture (which can be provided in one or more aliquots) in a kit. The proteins of a pre-labeled protein standard set provided in a kit preferably span a molecular weight range of from 10 kDa or less to 100 kDa or more, and can span a molecular weight range of from 5 kDa or less to 250 kDa or more.

In one embodiment of a kit, a pre-labeled standard set provided in a kit comprises a plurality of labeled proteins, in which one or more of the labeled proteins is selectively labeled on a first amino acid and lacks a second amino acid that is capable of reacting with a dye used to label the protein.

In some preferred embodiments, a pre-labeled protein standard set provided in a kit comprises at least five labeled proteins, in which two, three, four, or five of the labeled proteins are labeled on cysteine and lack lysine. The invention also includes a kit that comprises a pre-labeled protein standard set that comprises at least 10 labeled proteins, in which the labeled proteins span a molecular weight range of from 10 kDa or less to 100 kDa or greater, in which the electrophoretic migration of each of the pre-labeled protein standards having a molecular weight of 5 kDa or greater is within 5% of the electrophoretic migration of each of the same protein standards in unlabeled form, calculated from the same acrylamide gel. The invention also includes a kit that comprises a pre-labeled protein standard set that comprises at least 12 labeled proteins, in which the labeled proteins span a molecular weight range of from 5 kDa or less to 260 kDa or greater, in which the electrophoretic migration of each of the pre-labeled protein standards having a molecular weight of 5 kDa or greater is within 5% of the electrophoretic migration of each of the same protein standards in unlabeled form, calculated from the same acrylamide gel.

In some embodiments, a pre-labeled protein standard set provided in a kit includes two or more proteins labeled on a first amino acid, in which the ratios of the number of residues of the first amino acid to molecular weight of at least two of the two or more labeled proteins are within 5% of one another, in some embodiments within 2.5% of one another. In some preferred embodiments of a pre-labeled protein standard set provided in a kit, at least two proteins selectively labeled on a first amino acid have between two and seven, or between three and five residues of a first amino acid, such as between 3.5 and 4.5 residues of a first amino acid per 10 kDa. In some preferred embodiments of a pre-labeled protein standard set provided in a kit, at least five proteins of the set that are selectively labeled on a first amino acid have between three and five residues of a first amino acid, such as between 3.5 and 4.5 residues of a first amino acid per 10 kDa. In some preferred embodiments, a pre-labeled protein standard set provided in a kit comprises at least five labeled proteins, in which two, three, four, or five of the labeled proteins are labeled on cysteine and lack lysine, and the two, three, four, or five labeled proteins have a ratios of cysteine residues to molecular weight that are within 5% of one another. In these embodiments, the two, three, four, or five labeled proteins can have between two and seven, or between two and five, cysteine residues per 10 kDa.

Also provided herein is kit comprising a set of pre-labeled protein standards that includes at least one labeled protein that comprises two or more copies of a sequence derived from a naturally-occurring protein, in which the at least one labeled protein lacks lysine residues and is labeled on at least one cysteine residue. In some preferred embodiments, the set of pre-labeled protein standards comprises two or more labeled proteins that comprise two or more copies of a sequence derived from a naturally-occurring protein, in which the two or more labeled proteins lack lysine residues and are labeled on at least one cysteine residue. In some preferred embodiments, the set of pre-labeled protein standards comprises three or more, four or more, or five or more, six or more seven or more, eight or more, nine or more, ten or more, eleven or more, or twelve or more labeled protein standards in which two or more, three or more, four or more, five or more of the cysteine-labeled proteins that lack lysine comprise two or more copies of a sequence derived from a naturally-occurring protein. The standards can be labeled with two, three, four, or more visually distinguishable dyes. The standards can span a molecular weight range of from less than 10 kDa to greater than 100 kDa, or from less than 5 kDa to greater than 250 kDa. The standards can have two or more, three or more, four or more, five or more, or six or more protein standards that differ by an increment that is a multiple of 10 kDa (plus or minus 1 kDa). In preferred embodiments, all of the protein pre-labeled standards of the set can migrate within 5% of the migration of the same proteins in unlabeled form. In preferred embodiments, the ratios of cysteine residues to molecule weight for the two or more, three or more, four or more, five or more cys-labeled proteins that lack lysine do not vary by more than 5%. In preferred embodiments, each of the two or more, three or more, four or more, five or more cys-labeled proteins that lack lysine have between one and ten, between two and seven, or between three and five cysteine residues per 10 kDa.

In related embodiments, a pre-labeled protein standard set of the invention includes three or more labeled proteins, in which a first and a second protein of the three or more labeled proteins differ from one another by the same molecular weight increment as a second and third protein of the set. In some embodiments, the molecular weight increment is, when rounded to the nearest 1 kDa, a multiple of 5 kDa, a multiple of 10 kDa, a multiple of 20 kDa, or a multiple of 50 kDa. In some preferred embodiments, a pre-labeled protein standard set of the invention includes five or more labeled proteins, in which at least five of the five or more labeled proteins differ from one another by a multiple of 10 kDa. In some preferred embodiments, a pre-labeled protein standard set provided in a kit comprises at least five labeled proteins, in which two, three, four, or five of the labeled proteins are labeled on cysteine and lack lysine, and at least three, at least four, or at least five of the labeled proteins of the set differ in molecular weight increments by a multiple of 10 kDa (plus or minus 1 kDa).

In another aspect, the invention provides methods of providing a set of pre-labeled protein standards to a customer, in which the set of pre-labeled protein standards includes any of the pre-labeled standard sets and kits disclosed herein. In one embodiment, the method includes: providing a pre-labeled protein standard set to a customer, in which at least one of the labeled proteins of the standard set is selectively labeled on a first amino acid, in exchange for revenue. In another embodiment, the method includes: providing a pre-labeled protein standard set to a customer, in which the pre-labeled protein standard set comprises from five to twelve labeled proteins, and at least five of the labeled protein are labeled on cysteine and lack lysine residues. In another embodiment, the method includes: providing a pre-labeled protein standard set to a customer, in which two or more of the labeled proteins of the standard set is selectively labeled on a first amino acid and at least two of the two or more selectively labeled proteins have a constant ratio of a first amino acid to molecular weight, in exchange for revenue. In another embodiment, the method includes: providing a pre-labeled protein standard set to a customer, in which the pre-labeled protein standard set comprises from five to twelve labeled proteins, and at least five of the labeled protein are labeled on cysteine and lack lysine residues, and the at least five labeled protein have the same ratio of cysteine residues to molecular weight. In another embodiment, the method includes: providing a pre-labeled protein standard set to a customer, in which the pre-labeled protein standard set includes 12 or more labeled proteins, in which the migration of each of the labeled protein standards having a molecular weight of 5 kDa or greater is within 5% of the migration of each of the five or more protein standards in unlabeled form on the same acrylamide gels, in exchange for revenue. In another embodiment, the method includes: providing a pre-labeled protein standard set to a customer, in which the pre-labeled protein standard set comprises twelve labeled proteins, in which at least five of the twelve labeled proteins are labeled on cysteine and lack lysine residues, and in which the electrophoretic migration of each of the twelve labeled protein standards is the same as the electrophoretic migration of the same protein standard in unlabeled form on the same acrylamide gel.

The following examples are intended to illustrate but not limit the invention.

EXAMPLE 1

Sharp Molecular Weight Marker Expression Plasmids: 30, 40, and 50 kDa Proteins

Expression plasmids for the 30, 40, and 50 kDa proteins were made using pTrcBH 60 kd, a construct containing a synthetically derived open reading frame (ORF) consisting of six tandem *E. coli* thioredoxin (Thio) segments. Blue-Heron® Biotechnology (Bothell, Wash., USA) was contracted to synthesize the 1595 bp ORF according to specifications that would allow for optimal protein-dye labeling.

FIG. 1A aligns the truncated thioredoxin ORF of clone pTrxfusprl10A (see U.S. Pat. No. 6,703,484, herein incorporated by reference in its entirety having: 1) 23 amino acids removed from the carboxy terminus, 2) a substitution of glu for val at the last Thio (86th) codon position, and 3) 6 C-terminal histidines added to the C terminus, with the Thio ORF (top row of FIG. 1B) that was modified to contain 4 cysteine (C) and no lysine (K) amino acids. Two additional cysteines were added to the ORF by codon modification of serine residues (S) at positions 2 and 12. All 7 lysine (K) amino acids were changed to arginine (R) at positions 4, 19, 52, 70, 83 and methionine (M) at position 36 to favor the binding of the dye molecules to cysteine rather than lysine. Cysteine and methionine at positions 35 and 37 were replaced with arginine and cysteine to increase the distance between cysteine residues and minimize the potential steric hindrance created by two dye molecules binding to cysteines residues at positions 34 and 37. Isoleucines at positions 23 and 45 were changed to arginine to decrease the protein's predicted hydrophobicity.

The Thio ORF of 279 bp was truncated to meet the molecular weight requirements of the final product. In creating a six Thio repeat construct, the first of six Thio repeats of pTrcBH 60 kd was set at 208 bp (providing a translation product of 7.7 kd) and the remaining five identical repeats were set at 258 bp (each providing a translation product of 9.8 kd). Approximately every 18$^{th}$ amino acid's 3$^{rd}$ base codon wobbled to minimize repeats when the construct was fully assembled.

As shown by the diagram of FIG. 2A the six assembled Thio repeats were separated by five unique restriction sites. The 5' end of the six Thio repeat ORF contained a Bgl II site and the 3' end, containing the five unique restriction sites followed by a ten HIS sequence and capped with a Pme I site. This design allowed for the subcloning of this ORF, referred to a BH6mer ORF (SEQ ID NO:13, FIG. 2B), into a pTrc expression vector (Invitrogen, Carlsbad, Calif., USA) using BamH1 and Pme1 restriction sites, creating an expression plasmid from which an approximately 60 kd translation product could be made, with the flexibility of generating expression plasmids for synthesizing translation products of approximately 10, 20, 30, 40, or 50 kd from the same vector, depending on which of the five unique restriction site enzyme was employed to digest the plasmid before re-closing it to make a shorter construct.

Figure 3A:
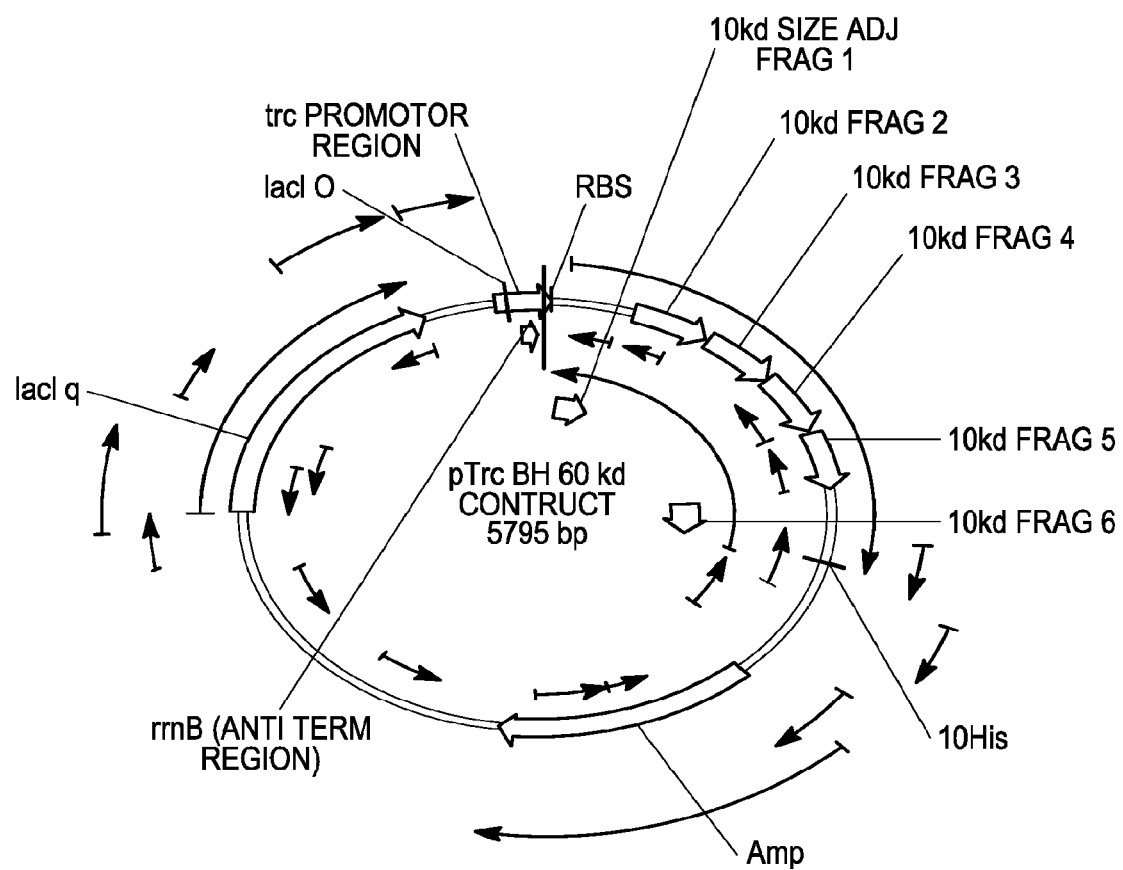
FIG. 3 A) shows a map of the pTrc BH 60 kDa "No Lysine" construct. B) provides the amino acid sequence of the pTrc BH 60 kDa expression product (SEQ ID NO:14)
Figure 4A:
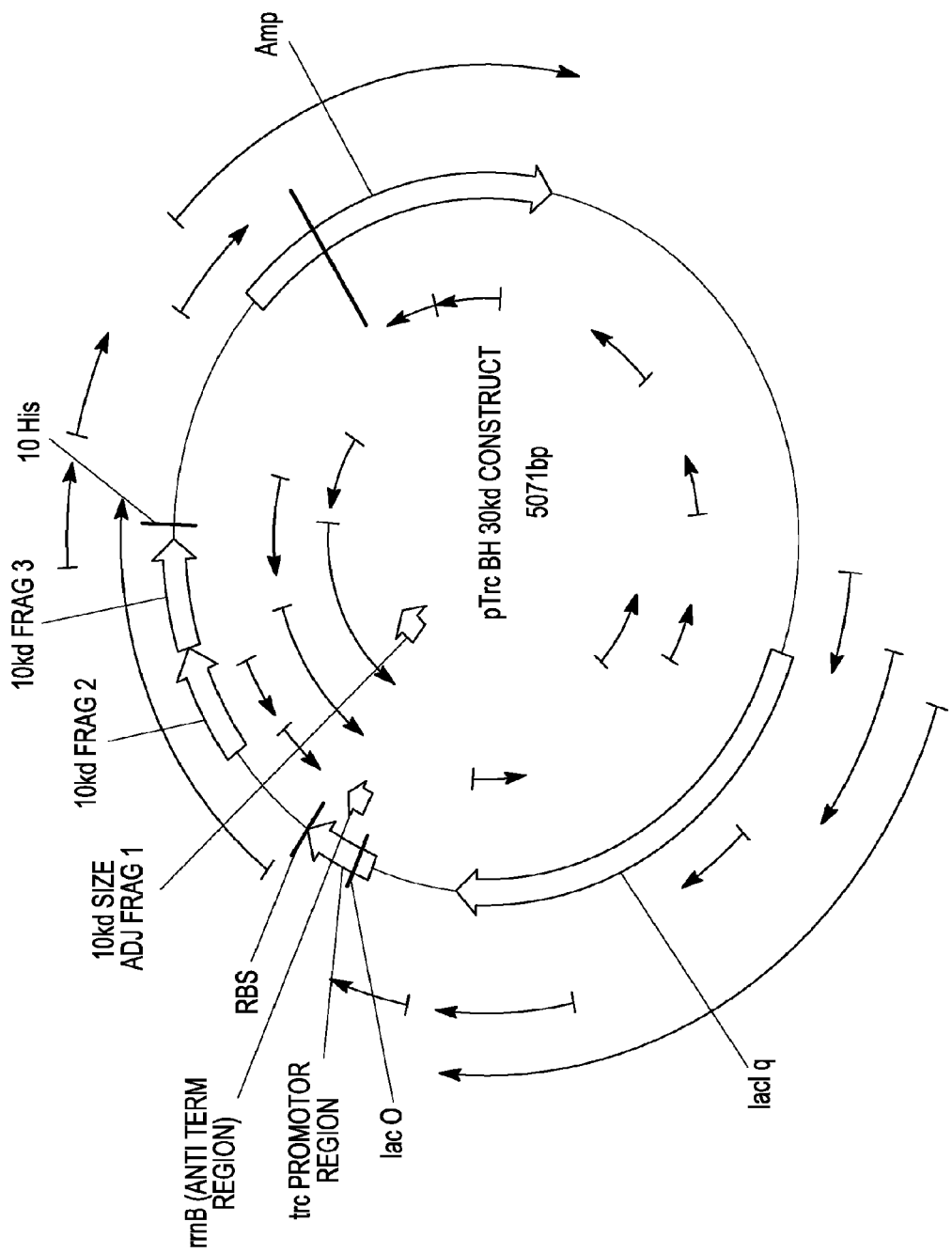
FIG. 4 A) shows a map of the pTrc BH 30 kDa "No Lysine" construct. B) provides the amino acid sequence of the pTrc BH 30 kDa expression product (SEQ ID NO:15).
Figure 5A:
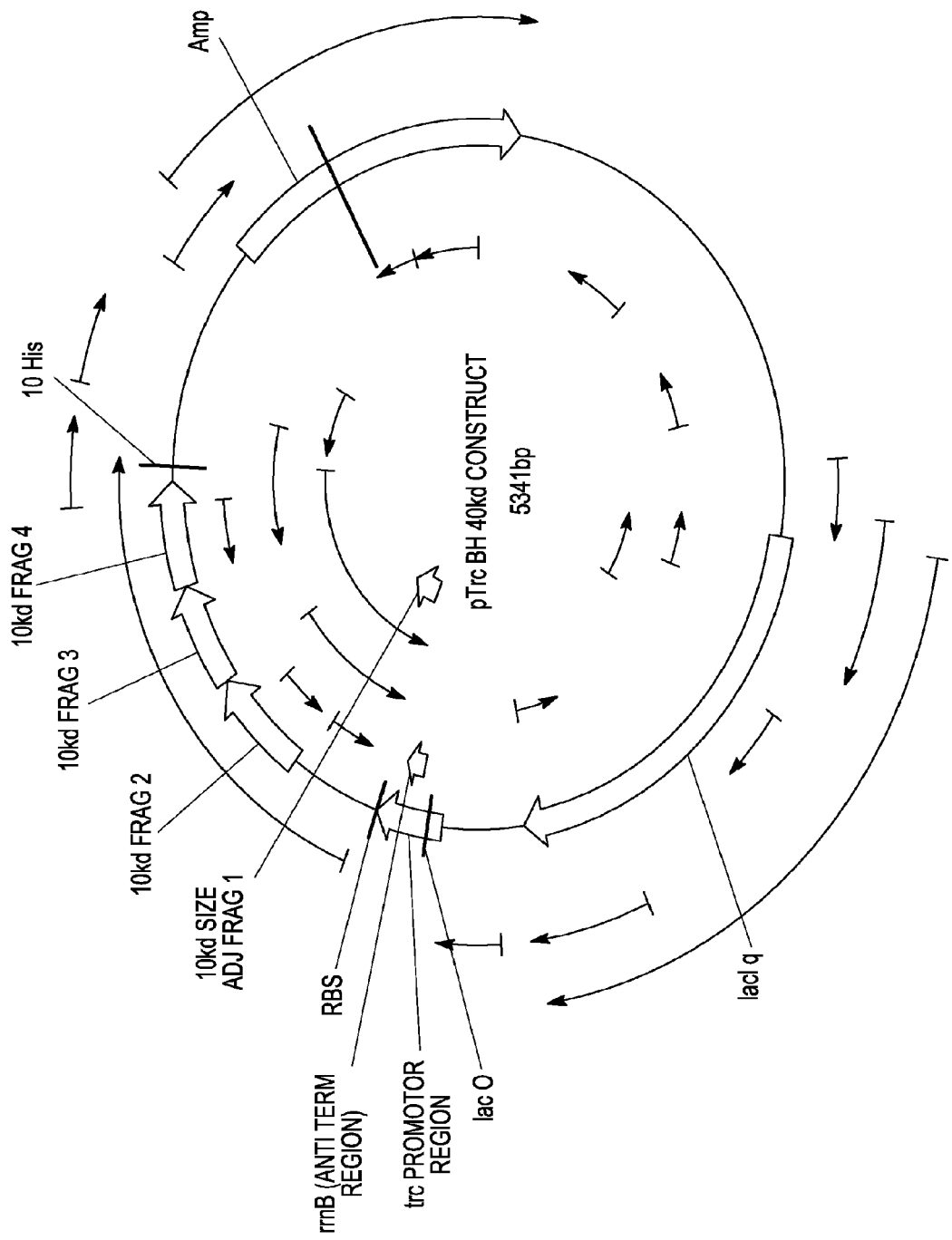
FIG. 5 A) shows a map of the pTrc BH 40 kDa "No Lysine" construct. B) provides the amino acid sequence of the pTrc BH 40 kDa expression product (SEQ ID NO:16).
Figure 6A:
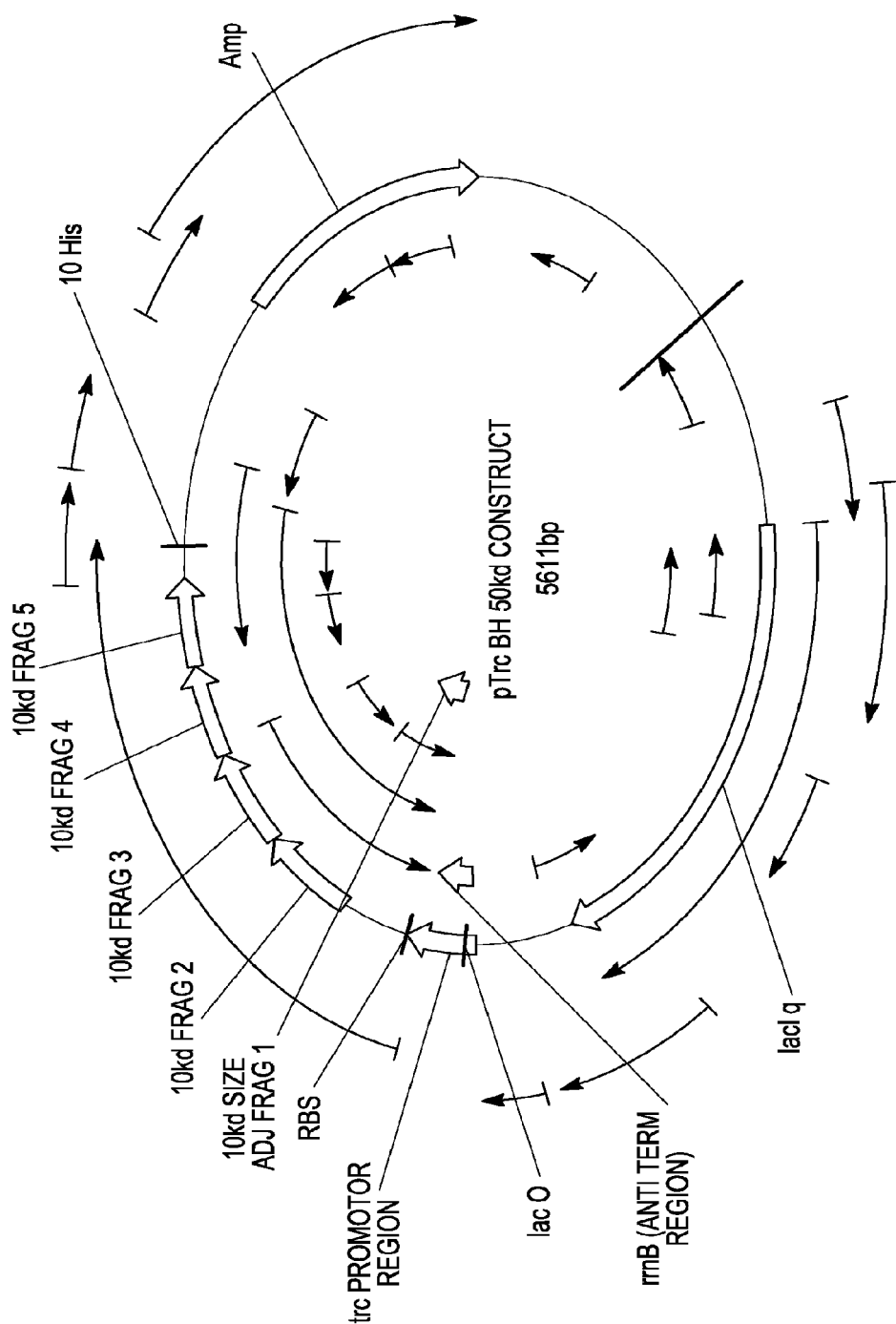
FIG. 6 A) shows a map of the pTrc BH 50 kDa "No Lysine" construct. B) provides the amino acid sequence of the pTrc BH 50 kDa expression product (SEQ ID NO:17).

FIG. 3A shows the map of the pTrc BH 60 kDa cloning construct used to generate the lower molecular weight pTrc BH 30 kDa construct (shown in FIG. 4A), pTrc BH 40 kDa construct (shown in FIG. 5A), and pTrc BH 50 kDa construct (shown in FIG. 6A).

The sequence-verified Thio repeat ORF insert (BH6mer ORF) from BlueHeron® Biotechnology (FIG. 2B, SEQ ID NO:13) was cut out of their pUC-minus cloning vector by sequential digests using PmeI followed by Bgl II. The six Thio insert (1595 bp) was gel purified and eluted using a S.N.A.P™ resin mini column (Invitrogen, Carlsbad, Calif., USA) and centrifugation at 14,000 rpm for 10 minutes at room temperature and ligated to a modified pTrc LacZ-Flash vector.

The pTrc LacZ-Flash expression vector that includes a LacZ ORF with a C-terminal lumio sequence and a 10 his tag, a trp/lac inducible promoter and sequences for enhancing expression of eukaryotic genes in *E. coli*. It was mutagenized by restriction digestion and ligation to delete the single NcoI site to allow for in-frame translation of the BH6mer ORF. The modified pTrc expression vector was digested with BamHI and PmeI and the 4285 bp vector fragment was gel purified.

The BH6mer ORF was ligated into the digested pTrc vector backbone via BamHI-PmeI to generate the pTrc BH 60 kd expression construct having the insert shown in FIG. 2A. Restriction digest screening using BamHI and EcoR I identified a positive clone and protein expression screening in BL21 DE3 STAR verified the restriction digest results.

The amino acid composition of the pTrc BH 60 kd protein determined by DNA sequencing of the construct showed a valine (V) residue capping the C-terminal 10 HIS sequence (FIG. 3B; SEQ ID NO:14). The valine capped HIS sequence originated from the pTrc LacZ-Flash vector within the Pme I site. The presence of this valine on the end of the 10 HIS tag did not affect Ni-NTA purification of the synthesized protein.

Additional pTrc BH expression clones were obtained by restriction digests using one of the five unique sites depicted in FIG. 2A. The map of pTrc BH 30 kd and the sequence of the 30 kDa ORF encoded by the insert (SEQ ID NO:15) is shown in FIG. 4. The map of pTrc BH 40 kd and the sequence of the 40 kDa ORF encoded by the insert (SEQ ID NO:16) is shown in FIG. 5. The map of pTrc BH 50 kd and the sequence of the 50 kDa ORF encoded by the insert (SEQ ID NO:17) is shown in FIG. 6. Clones were screened by colony PCR to identify positive expression constructs using the following primers: #24 pTrCHisFOR: GAGGTATATAT-TAATGTATCG (SEQ ID NO:18) and #12 pBAD_Rev: GATTTAATCTGTATCAGG (SEQ ID NO:19). Protein expression screens in BL21 DE3 STAR were preformed to validate PCR screen screening results.

EXAMPLE 2

Sharp Molecular Weight Marker Expression Plasmids: 110, 160, and 260 kd

Proteins

Expression constructs encoding 100, 150, and 250 kd proteins containing multimers of the BH6mer ORF, which contained 4 cys and 0 lys residues per 10 kd were made using insert fragments of the pTrc BH 60 kDa expression construct of Example 1 generated by PCR.

Synthesis of 50 kd PCR Inserts (1314 bp)

Using the pTrc BH 60 kDa expression construct of Example 1 as the PCR template, several 50 kDa inserts were generated using Platinum® PCR Supermix High Fidelity PCR mix (Invitrogen; Carlsbad, Calif.) that contained Taq DNA polymerase, *Pyrococcus* species GB-D thermostable polymerase, Platinum® anti-Taq polymerase antibody, 66 mM Tris-SO$_4$ (pH 8.9), 19.8 mM (NH$_4$)$_2$SO$_4$; 2.4 mM MgSO$_4$; 220 µM dNTPs; and stabilizers; with the following primer sets:

```
50.1_F:
                                          (SEQ ID NO: 20)
CCGGAGATCTATGTGTGATCGTATTATTCA
and 50.1_R:
                                          (SEQ ID NO: 21)
CCGGCTCGAGTTCGCCGTTACGGAAAAGCA;

50.2_F:
                                          (SEQ ID NO: 22)
CCGGCTCGAGATGTGTGATCGTATTATTCATCTGAC
and 50.2_R:
                                          (SEQ ID NO: 23)
CCGGCCTAGGTTCGCCGTTACGGAAAAGCA,
or 50.2_10HIS-Pme_R:
                                          (SEQ ID NO: 24)
GTTTAAACGTGATGATGATGGTGGTG GTGGTGG TGGTGT

TCGCCGTTACGGAAAAGCAGAAG;

50.3_F:
                                          (SEQ ID NO: 25)
CCGGCCTAGGATGTGTGATCGTATTATTCATCTGAC,
and 50.3_R:
                                          (SEQ ID NO: 26)
CCGGCGGCCGTTCGCCGTTACGGAAAAGCA,
or
```

-continued

```
50.3_10HIS-Pme_R:
                                       (SEQ ID NO: 27)
GTTTAAACGTGATGATGATGGTGGTGGTGGTGGTGTT

CGCCGTTACGGAAAAGCAGAAG;

50.4_F:
                                       (SEQ ID NO: 28)
CCGGCGGCCGATGTGTGATCGTATTATTCAT,
and 50.4_10HIS-Pme_R:
                                       (SEQ ID NO: 29)
GTTTAAACGTGATGATGATGGTGGTGGTGGTGGT GTTCG

CCGTTACGGAAAAGCAGAAG
```

The 1314 bp inserts (50 kDa) were gel purified on a 1.2% E-Gel®. The PCR inserts were TA cloned into pCR2.1 (Invitrogen; Carlsbad, Calif.) using the manufacturer's protocol. Primer design allowed for each 50 kd TA clone to have unique sequence ends that facilitated vector construction as shown in Table 2.

TABLE 2

50 kd Inserts used for High Molecular Weight Marker Constructs

| Insert Name | Insert Configuration |
|---|---|
| TA 50.1 | BgL II-50 kd-Xho I |
| TA 50.2 | Xho I-50 kd-Avr II |
| TA 50.2-10HIS-PmeI | Xho I-50 kd-10HIS-PmeI |
| TA 50.3 | AvrII-50 kd-EagI |
| TA 50.3-10HIS-PmeI | AvrII-50 kd-10HIS-PmeI |
| TA 50.4-10HIS-PmeI | EagI-50 kd-10HIS-PmeI |
| MM 50 kd | XhoI-SpeI-XbaI-BgLII-50 kd-NheI-BamHI-PstI |

White colonies were selected for colony PCR screening using the specific primer sets used in the cloning. The sequences of TA inserts of the 50.2 insert of clone 50.2_B3, the 50.3 insert of clone 50.3_C14, the 50.4 insert of clone 50.4-10HIS-PmeI_C4, and the MM 50 kd insert of an MM 50 kd clone were confirmed using the primers in Table 3.

TABLE 3

Sequencing Primers used to Confirm 50 kd Inserts

| Primer | Sequence |
|---|---|
| TA50kd_1F | GTGCGGTCCACGTATGTG (SEQ ID NO: 30) |
| TA50kd_2F | GGCGCGTCTCGTCGAC (SEQ ID NO: 31) |
| TA50kd_2R | ACTCTGCCCAGAAGTCGAC (SEQ ID NO: 32) |
| TA50kd_3F | CGAAACCGGTATGTGCG (SEQ ID NO: 33) |
| TA50kd_3R | CGATCGCACATACCGG (SEQ ID NO:34) |
| T7#6 | TAATACGACTCACTATAGGG (SEQ ID NO: 35) |
| PCRII200F#738 | CACACAGGAAACAGCTATGA (SEQ ID NO: 36) |

All of the sequenced clones contained the identical 50 kd-encoding 1314 bp sequence of SEQ ID NO:37 (FIG. 7). Assembly of pTrc 50 kDa Base Vector, and pTrc 110 kDa, pTrc 160 kDa, and pTrc 260 kDa Expression Vectors pTrc 50 kDa Base Vector:

TA clone 50.1_clone 2D was digested with BgL II and Not I (site from the pCR2.1 vector) to remove the 50 kDa insert. The fragment was gel purified. The modified pTrc LacZ-Flash vector was digested with BamHI-Not I and the gel purified (4377 bp) vector was ligated with the TA 50.1_2D insert.

A positive clone was identified by colony PCR using the 50.1 forward primer (SEQ ID NO:20) and 50.1 reverse primer (SEQ ID NO:21). This clone, labeled pTrc 50.1 D3 was the base construct used in subsequent subclonings for construction of the pTrc 110 kDa, pTrc 160 kDa, and pTrc 260 kDa expression vectors.

pTrc 110 kd Expression Vector:

TA clone 50.2-10HIS-PmeI clone B6 was digested with XhoI and PmeI. The gel purified insert was subcloned into pTrc 50.1 D3 which had been also digested with XhoI and PmeI. XhoI and PmeI restriction digest screening identified a positive clone that was later confirmed by protein expression screening.

Figure 8A:
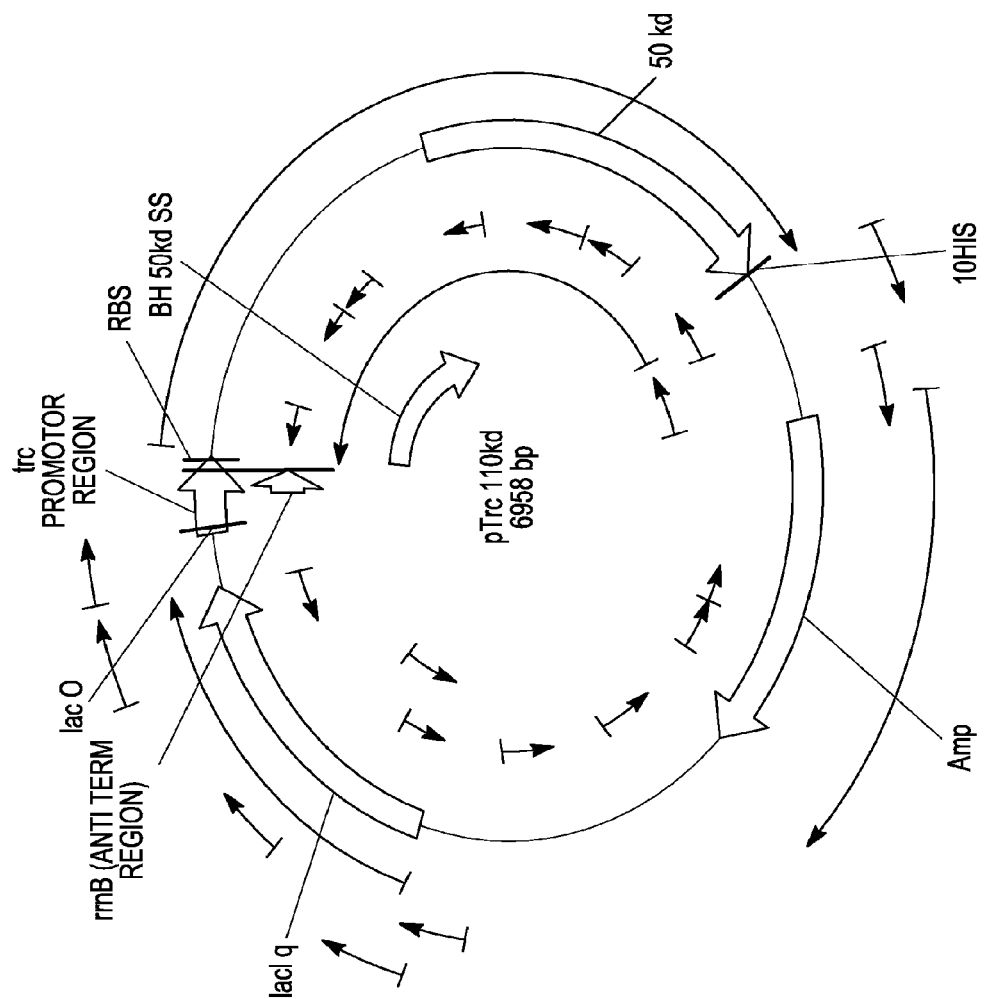
FIG. 8 A) shows a map of pTrc 110 kd. B) provides the deduced amino acid sequence of the expression product of pTrc 110 kd (SEQ ID NO:38).

The expressed protein had a molecular weight that was closer to 110 kDa than to the expected 100 kDa. It is believed that during the preparation of the fragments one of the presumed 50 kDa subcloned fragments (the first or the second) was a 60 kDa Thio repeat fragment instead of a 50 kDa Thio repeat fragment. Mass spectrometry analysis of the actual molecular weight of the expressed protein revealed that it was 10 kDa larger than expected (Table 4). The expression clone was labeled pTrc 50.1-2 Pme, Clone B6-9 and renamed pTrc 110 kd (FIG. 8A). The sequence of the insert was not directly determined. The predicted sequences based on the cloned fragments is provided as SEQ ID NO:38 in FIG. 8B).

pTrc 160 kd Expression Vector:

TA clone 50.2 clone B3 was digested with XhoI and Not I (site from pCR2.1) to remove the 50 kDa insert. The pTrc 50.1 D3 vector was digested with XhoI and Not I and the gel purified vector was ligated with the 50.2 B3 gel purified insert. A positive clone was identified by restriction digest screening using XhoI-AvrII and was labeled pTrc1-2 C6.

Figure 9A:
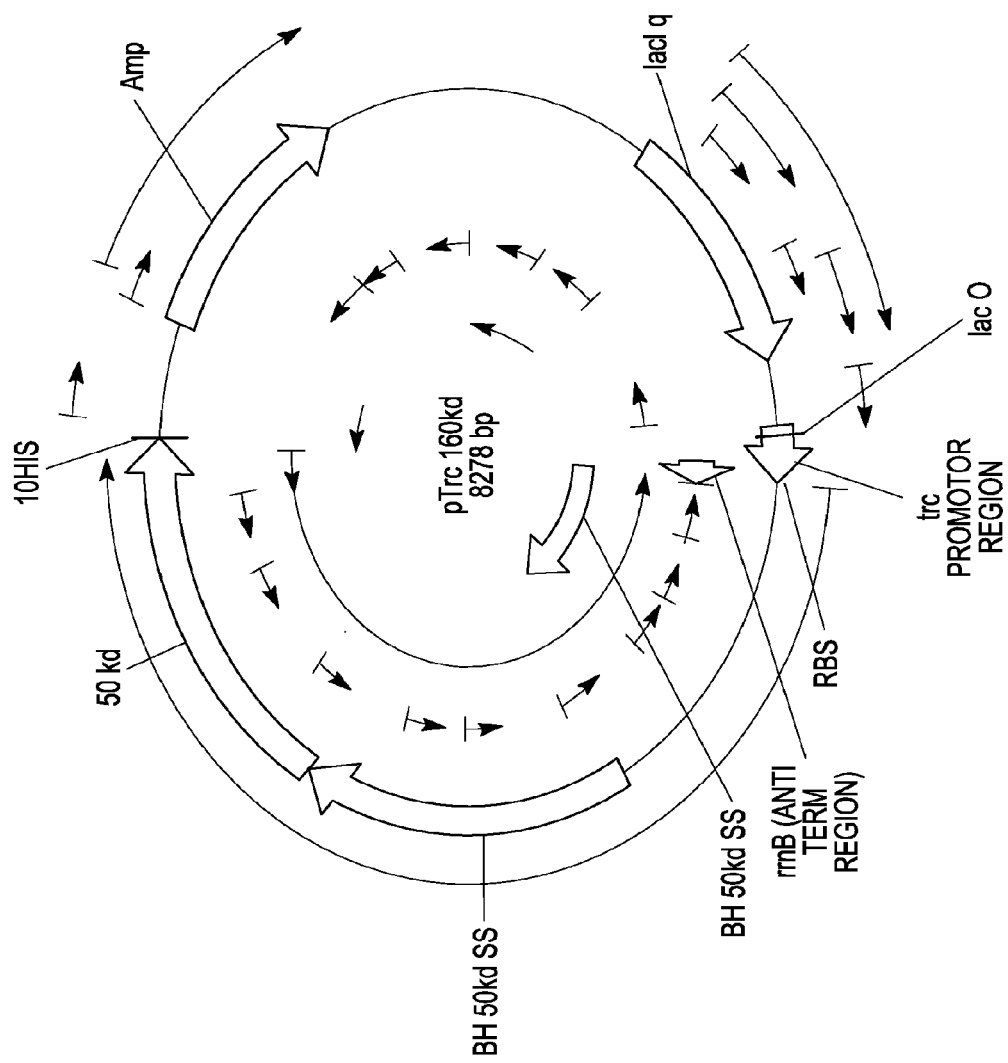
FIG. 9 A) shows a map of pTrc 160 kd. B) provides the deduced amino acid sequence of the pTrc 160 kd expression product (SEQ ID NO:39).

The pTrc1-2 C6 vector, containing two 50 kd inserts, was digested with Avr II and PmeI. The gel purified vector was ligated with TA clone 50.3-HIS-Pme I insert that had been digested with AvrII and PmeI and gel purified. A positive clone was identified by restriction digest screening using Avr II-PmeI and later confirmed by protein expression screening. In this case, the expressed protein had a molecular weight that was closer to 160 kDa than to the expected 150 kDa. It is believed that during the preparation of the fragments one of the presumed 50 kDa subcloned fragments was a 60 kDa Thio repeat fragment instead of a 50 kDa Thio repeat fragment. Mass spectrometry analysis of the actual molecular weight of the expressed protein revealed that it was 10 kDa larger than expected (Table 4). The expression clone was labeled pTrc1,2,3 Pme and renamed: pTrc 160 kd (FIG. 9A). The sequence of the insert was not directly determined. The predicted sequences based on the cloned fragments is provided as SEQ ID NO:39 in FIG. 9B).

pTrc 260 kd Expression Vector:

A 260 kDa protein expression vector, pTrc 160+LacZ, was also constructed. Using the unique restriction site (Avr II), located between 50 kDa Thio repeat fragments 2 and 3 in the pTrc 160 kDa protein construct (FIG. 9), a truncated LacZ gene encoding a 100 kDa polypeptide (SEQ ID NO:40; FIG. 10) was cloned into the AvrII site.

The 260 kDa protein had an estimated mass of 253,624 daltons. The protein contained 73 cysteines and 19 lysine amino acids. The sequence of the insert was not directly determined. The predicted sequences based on the cloned fragments is provided as SEQ ID NO:41 in FIG. 11B).

The LacZ gene was generated with Platinum® PCR Supermix High Fidelity PCR mix (Invitrogen; Carlsbad, Calif.) using primers capped with Avr II restriction sites. The resulting PCR product was Topo cloned into the pCR®-Blunt cloning vector (Invitrogen, Carlsbad, Calif., USA) using the Zero Blunt® kit (Invitrogen, Carlsbad, Calif., USA).

The truncated LacZ ORF was excised from the cloning vector with Avr II digestion and the fragment was gel purified. The pTrc 160 kDa construct was linearized with AvrII and gel purified.

Figure 11A:
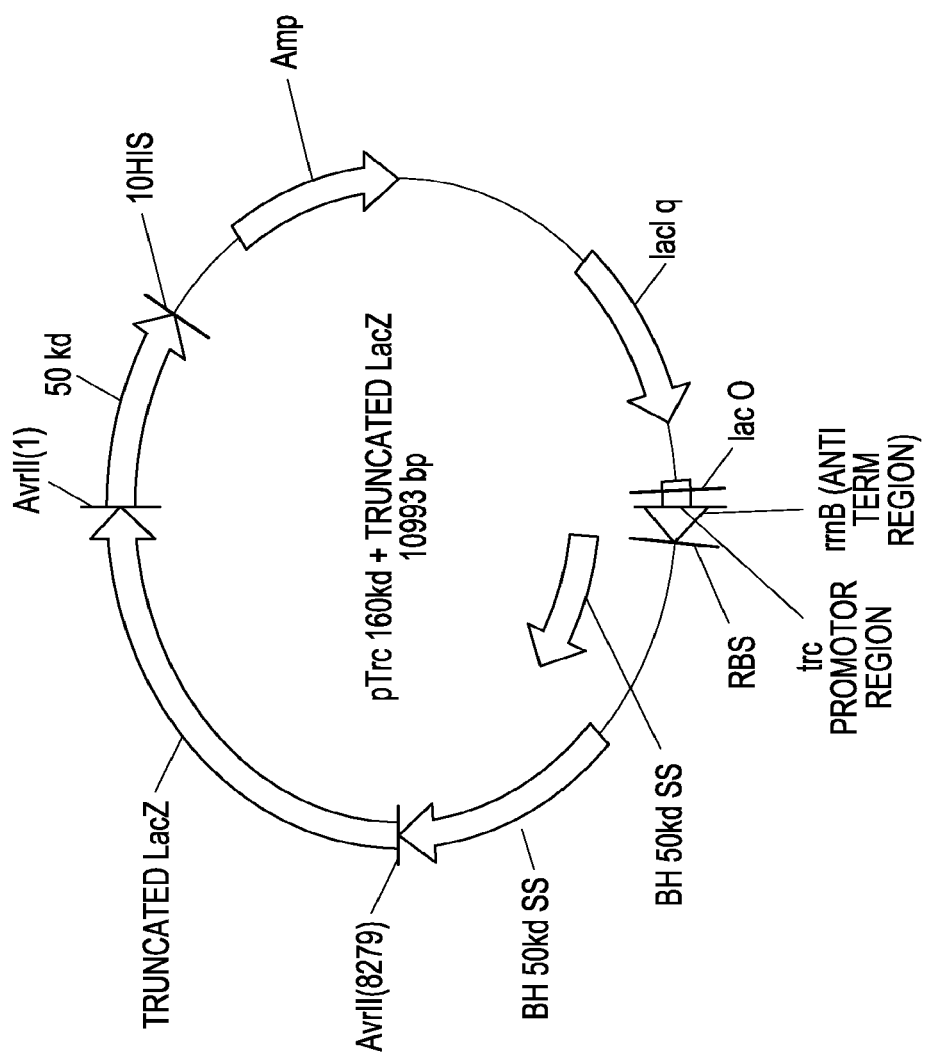
FIG. 11 A) shows a map of pTrc 260 kd. B) provides the deduced amino acid sequence of the pTrc 260 kd expression product (SEQ ID NO:41).

The truncated LacZ insert was ligated into a non-alkaline phosphatase treated pTrc 160 kDa vector. The ligation reaction was transformed into One Shot® Top 10 competent bacterial cells (Invitrogen, Carlsbad Calif., USA) and the resulting colonies were PCR screened for the LacZ gene. PCR colony screening identified 11/80 clones containing the LacZ insert and expression screening identified 5/11 clones having the LacZ insert in the correct orientation. The pTrc 160+LacZ clone B1 in BL 21 DE3 was expressed in 1.0 L of BRM-Amp, 30° C., 18 hrs, uninduced, to verify expression performance. This clone was subsequently designated pTrc 260 kDa (FIG. 11A).

To test for expression of proteins, expression plasmids were transformed into competent BL21-DE3 cells. The cells were grown in LB media with 100 ug/ml Ampicillin at 37° C. IPTG was added to 1 mM when the $OD_{600}$ reached 0.4-0.6 and the cells were incubated at 37° C. for an additional 4-6 hours.

After the expression period 1 ml of the cell cultures were centrifuged at 5000×g for 5 minutes. The liquid fraction was discarded and 100 μl of BugBuster® HT protein extraction reagent (Novagen, Madison, Wis., USA) with 25 ug/ml lysozyme was added to the cells. The sample was vortexed to resuspend the cells and incubated for 10 minutes at room temperature. 50 μl of the lysate was transferred to a separate tube. Another 50 ul of the lysed bacterial sample was centrifuged at 10,000×g for 5 minutes. The liquid fraction was discarded and the pellet (insoluble fraction) was resuspended in 50 μl of 1×LDS Sample buffer.

5 μl of 4×LDS and 2 μl NuPAGE reducing reagent were added to 15 μl of the whole lysate and to 15 μl of insoluble fraction. The samples were incubated for 10 minutes at 70° C. 10 μl of each sample were loaded on a 4-12% NuPAGE® gel and run with 1×MES running buffer at 200V for 37 minutes. The gel was stained with SimplyBlue™ SafeStain protein stain using the microwave protocol to visualized the expressed proteins.

EXAMPLE 3

Production of Recombinant Proteins

The following procedures were used for the production of recombinant proteins for use as molecular weight standards.
30, 40, 50 and 110 kDa (no-lysine (NL)) proteins
Reagents
BugBuster® HT protein extraction reagent (Novagen, Madison, Wis., USA)
Freshly prepared 25 mg/ml lysozyme in ultrapure water
Induced 50 ml cell cultures (after reaching an O.D. of 0.5 in that contains rich media [24 g/L yeast extract, 12 g/L tryptone, 0.05% glucose, 1 mM $MgSO_4$, 50 mM $KH_2PO_4$, 50 mM $K_2HPO_4$, 10 mM $(NH_4)_2$—$SO_4$, and 1% glycerol], lactose is added to 1 mM, and the culture is incubated overnight at a temperature of 32 degrees C. or 37 degrees C., or as low as 30 degrees C.)

Large scale cultures can be grown in a 7 L fermentor (e.g., an Applikon fermentor) through which air is bubbled. Protein molecular weight standards were produced in large quantity by inoculating a 2.8 L non-baffled seed flask of approximately 1 liter of rich media with a freshly transformed (less than one week old) colony containing the expression plasmid. (Rich media per liter: 12 grams of tryptone, 24 grams of yeast extract dissolved in distilled water to a final volume of 1 liter is autoclaved, and after cooling to approximately 30 degrees C., 10 mls of 10 mg/ml ampicillin, 50 mls of 20×NPS, 10 mls of 5052 solution, and 1 ml of 1 molar Magnesium Sulfate are added. 20×NPS is made by adding 66 g ammonium sulfate; 136 g potassium phosphate, monobasic; and 142 g potassium phosphate, dibasic, per liter distilled water. 5052 solution is made by adding 500 grams of glycerol and 50 grams of glucose per liter of distilled water. 20×NPS and 5052 solutions are filter sterilized using micron filters.) The seed flask is incubated with shaking (250 rpm) at 30 degrees C. until the OD is between 1.0 and 3.0 (approximately 7-9 hours).

150 mls of the seed flask culture is then transferred to a 7 liter fermentor that contains 5 liters of rich media made as for the seed culture. The fementor is incubated with aeration parameters at 1.25 lpm air, 500 rpm agitation, and the pH is controlled to 6.8 using KOH or 5 M $H_3PO_4$. Incubation is at 30 degrees C. for approximately 1.5 to 2 hours, or until the OD reaches 0.5 to 1. At this time lactose is added to the culture to a final concentration of between 0.05% and 0.5%. For example, 50 mls of a solution of 20% lactose is added to the 5 L culture for a final concentration of 0.2% lactose.

The cells are harvested at early stationary phase, when two consecutive hourly readings of less than 0.5 OD change. This generally occurs 14-17 hours after inoculation. The final OD is generally 10 or greater.
Protein Isolation
8M urea, 20 mM phosphate, 500 mM NaCl pH=7.8
Ni-NTA resin
8M urea, 20 mM phosphate, 500 mM NaCl pH=6
8M urea, 20 mM phosphate, 500 mM NaCl pH=4
10N NaOH
Materials and Equipment
50 ml centrifuge tubes
Centrifuge capable of obtaining 10,000×g force
Protein Extraction
50 ml cell culture is centrifuged at 5000×g for 10 minutes
The cell media is discarded and 2.5 ml BugBuster® HT protein extraction reagent (Novagen, Madison, Wis., USA) including 25 μl of 5 mg/ml lysozyme are added to the cell paste
The cells are re-suspended in the lysis reagent by vortexing intermittently for 30 minutes at room temperature
The lysed sample is centrifuged for 10 minutes at 8,000× g.
The soluble fraction is discarded
4 ml 8M urea, 20 mM phosphate, 500 mM NaCl pH=7.8 is added to the pellet.
The sample is vortexed for 10-15 seconds to disperse the pellet and then immediately mixed using a Polytron mixer.
If the sample looks clear after the mixing with the Polytron centrifugation is performed. Otherwise the sample is warmed at 70° C. for 5 minutes to facilitate the solubilization of protein prior to centrifugation.

The sample is left to cool down to room temperature
The sample is centrifuged for 5 minutes at 5,000×g to pellet cell debris NTA Purification The solubilized protein is loaded on a 10 ml Ni-NTA column equilibrated in 8M urea, 20 mM phosphate, 500 mM NaCl pH=7.8. The column is attached to a stand and the liquid is drained from the column. The column is plugged with a cap and 4 ml 8M urea, 20 mM phosphate, 500 mM NaCl pH=7.8 are added to the column. The column is incubated on the shaker for 2 minutes and then the wash is drained from the column. The pH 7.8 wash process is repeated 1 more time. 4 ml of 8M urea, 20 mM phosphate, 500 mM NaCl pH=6 are added to the column and the column is incubated for 2 minutes on the shaker. The wash solution is discarded and the pH 6 wash process is repeated 1 more time. The bound protein is eluted with addition of 5 ml 8M urea, 20 mM phosphate, 500 mM NaCl pH=4 to the top of the column and collecting 1 ml fractions. The collected fractions are analyzed by electrohoresis. The fractions with the purified proteins are pooled together and the pH is adjusted to 7.5-8 with NaOH.

Protein Concentration 14 ml 60% TCA is added to 30 ml protein solution obtained from the Ni-NTA purification add and mixed well. The protein solution plus TCA is incubated at 4° C. for 1-2 hours and then centrifuged at 8,000×g for 10 minutes at 4° C. The liquid is discarded and 30 ml of ultrapure H$_2$O is added and mixed well. The protein is centrifuged at 8000×g for 10 minutes and liquid is discarded taking care not to discard the protein pellet. The H$_2$O wash is repeated, and then 300 μl of 50 mM Tris, 1% SDS pH=8 is added to the pellet. The protein is heated at 70° C. for 10-15 minutes if needed and vortexed to resolubilize the protein.

160 and 260 kDa Purification

Reagents: Complete Protease Inhibitor (Roche Applied Science, Indianapolis, Ind., USA); Freshly prepared 25 mg/ml lysozyme (Calbiochem, San Diego, Calif., USA) in ultrapure water; Induced cell culture as for 30, 40, 50 and 110 kDa (NL) proteins; Amberlite MB-150 (Sigma-Aldrich); Toyopearl AF Chelate 650M (Tosoh Bioscience, Tokyo, Japan); CHAPS detergent; Urea; 1M Na-phosphate pH=7.8; Imidazole; 5M HCl; Cobalt II chloride.

Preparation of Solutions:

Conditioning Solution: 8M Urea, 20 mM Phosphate, 0.5% CHAPS pH=7.8 (2 Liters)

Solubilize 960 g of urea in water. Deionize for 2 or more hours with 10 g/liter Amberlite mixed bed resin. Adjust the volume to 2 liters. Filter through 0.2 or 0.4 um filter. Add 40 ml 1M sodium phosphate pH=7.8. Add 10 grams of CHAPS and mix until solubilized Elution Buffer: 8M Urea, 200 mM Imidazole, 0.5% CHAPS pH=7.8

Solubilize 960 g of urea in water. De-ionize for 2 or more hours with 10 g/liter Amberlite mixed bed resin. Adjust the volume to 2 liters. Filter through 0.2 or 0.4 um filter. Add 27 grams of imidazole. Titrate the pH to 7.8-8 with 5M HCl. Add 10 grams of CHAPS and mix until solubilized.

Extracting the protein is performed as follows: 10 ml BugBuster® HT protein extraction reagent (Novagen, Madison, Wis., USA) with Complete Protease Inhibitor (Roche Applied Science, Indianapolis, Ind., USA) is added per every 1 g cell paste. One tablet of inhibitor is used for every 50 ml solution. 40 μl of 25 mg/ml lysozyme are added per every 1 gram paste. The cells are re-suspended in the lysis reagent by vortexing. The lysis is performed for 1 hour at room temperature on shaker or rotary mixer. The lysed sample is centrifuged for 10 minutes at 8,000×g. The soluble fraction is discarded. 5 ml of Column Conditioning solution (8M urea, 20 mM phosphate, 0.5% CHAPS pH=7.8) is added for each gram of cell paste. The cell paste is vortexed for 10-20 seconds to break the pellet and the paste is mixed with the Polytron right away. The sample is centrifuged at 8,000×g for 10 minutes to remove any insoluble particles. The solubilized fraction is retained for HIS purification. The purification should be performed the same day the lysate is prepared.

HIS purification is performed as follows: Toyopearl Chelate 650M resin (Tosoh Bioscience, Tokyo, Japan) is loaded with cobalt II chloride. The resin is washed extensively with water to remove any unbound cobalt The column should be a light pink color after washing with water. The column is washed extensively with Column Conditioning solution (8M urea, 20 mM phosphate, 0.5% CHAPS pH=7.8). The sample is loaded on the column (about 20 ml of sample can be applied to 100 ml column bed volume). The flow rate is stopped and the column is incubated for 1 hour at room temperature. The column is washed until the signal UV 280 nm signal goes to the baseline with Column Conditioning Solution. Protein is eluted with Elution buffer (8M urea, 200 mM Imidazole, 0.5% CHAPS pH=7.8).

For buffer exchange, a Bio-Gel P-6 column is prepared having 10 column volumes to the sample volume. The column is equilibrated with 50 mM Tris, 1% SDS pH=8.20% SDS is mixed to the sample to a final concentration of 1%. The sample is run through the column and fractions are monitored using 280 nm detection. The first peak is collected as the protein peak. The protein is concentrated to 2-3 mg/ml using 100 kDa MWCO membrane.

Protein Quantitation

Contaminating bands can interfere with the accurate estimation of protein concentration if total protein concentration in solution is determined. Therefore a gel-based method for protein quantitation is preferred for the molecular weight standard proteins.

A standard solution of 2 mg/ml Bovine Serum Albumin (BSA) from Pierce Biotechnology (Rockford, Ill., USA) is used to compare band intensities on electrophoresis gels. 1 μl of the 2 mg/ml BSA solution is added to 25 μl of 4×LDS Sample Buffer, 64 μl water and 10 ul NuPAGE® Reducing Reagent (Invitrogen, Carlsbad, Calif., USA). A sample that includes 1 μl of the concentrated molecular weight standard protein is prepared the same way and both samples are incubated for 10 minutes at 70° C. The BSA standard and molecular weight standard protein (5 μl of each) are run side by side on an electrophoresis gel. Multiple standards are preferably compared on the same gel, in which 5 μl of each marker protein sample is loaded between lanes of the BSA standard. The sample concentration is determined visually or using the Alpha Imager 3000 with quantitation software (Alpha Innotech, San Leandro, Calif., USA).

EXAMPLE 5

Insulin b-Chain Purification

Bovine Insulin consists of two polypeptide chains: Peptide Insulin B chain: theoretical pI: 6.90/Mw (average mass): 3399.93; and Peptide Insulin A chain: theoretical pI: 3.79/Mw (average mass): 2339.65. The bovine insulin b-chain was purified by reduction of bovine pancreas insulin (Sigma-Aldrich, St. Louis, Mo., USA) at denaturing conditions and then separation of the b-chain on an ion exchange column.

The method used for purification was the following: insulin was solubilized at 5 mg/ml in 8M urea, 50 mM Tris pH=8. 10 ul of 400 mM tributylphosphine (TBP) was added per every ml of solution (to 4 mM final concentration). The solution was heated for 5 minutes at 70° C. with occasional vortexing. The solution became clear and was cooled to room temperature. The sample was loaded on a DEAE ion exchange column equilibrated with 8M urea in 50 mM Na-acetate pH=5.3. The column was washed with 8M urea in 50 mM Na-acetate pH=5.3 for 10 minutes. The b-chain eluted in the wash buffer. Fractions were collected (monitored at 280 nm using UV detector). Bound a-chain was eluted with 8M urea in 50 mM Na-acetate, 500 mM NaCl pH=5.3.

The purified b-chain was precipitated with addition of 60% TCA to a final concentration of 20%. After a 30 minute incubation at −20° C. for 30 minutes the b-chain preparation was centrifuged at 10,000×g to collect the protein. The TCA supernatant was removed and the precipitate was spun again for 10 seconds at 2000×g to collect TCA drops from the tube wall. Remaining liquid was removed, and the protein pellet was resolubilized in 50 mM Tris, 1% SDS pH=8 at high concentration (for example, 4 mg/ml or higher.) If the pH was less than 7.5-8 it was adjusted with NaOH.

Insulin Quantitation

The concentration of insulin was determined by measuring the absorbance at 280 nm after zeroing with a solution of 50 mM Tris, 1% SDS pH=8. The insulin-b chain has theoretical absorbance of 0.913 at 1 mg/ml concentration (according to the Swiss-Prot Protein Parameters tool). The concentration can be determined by dividing the actual absorbance of the protein solution accounting for the dilution, by the absorbance of 1 mg/ml solution. $C=A \times D/0.913$, where C is concentration (mg/ml); A is absorbance at 280 nm; and D is dilution.

EXAMPLE 6

Protein Alkylation of Unstained Markers

Insulin b-chain

Alkylation is performed at a protein concentration of 1 mg/ml. 100 μl of 10 mg/ml Insulin-b chain is brought up to a volume of 1 ml in a solution having a final concentration of 50 mM Tris pH=8, 0.5% SDS. 10 μl of 400 mM tributylphosphine (TBP) in isopropanol was added to the protein sample and the mixture was vortexed for 10-15 seconds. The sample was incubated for 10 minutes at 70° C. and then cooled for 5 minutes at room temperature (or until the temperature dropped to 30° C.). 50 μl of 1M iodoacetamide in ultrapure water was added, and the sample was vortexed for 3-5 seconds and then incubated for 40-60 minutes at room temperature in darkness.

10 kDa BenchMark™ Protein Standard

The 10 kDa BenchMark™ protein marker is the recombinantly-expressed truncated E. coli thioredoxin protein that includes amino acids 1-85 from E. coli thioredoxin, a substitution of glutamic acid for valine at amino acid at amino acid position number 86, and histidine residues at positions 87-92 (Trxfusprl10A; see FIG. 3 of U.S. Pat. No. 6,703,484, herein incorporated by reference in its entirety). 100 μl of the 10 kDa BenchMark™ stock solution (OD=8.3) was brought up to a volume of 1 ml with a final concentration of 50 mM Tris pH=8 and 0.5% SDS. 10 μl of 400 mM tributylphosphine (TBP) in isopropanol was added and the protein sample was vortexed for 10-15 seconds and then incubated for 10 minutes at 70° C. The sample was allowed to cool down for 5 minutes at room temperature (or until the temperature dropped to 30° C.) and then 50 μl of 1M iodoacetamide was added and the sample was vortexed for 3-5 seconds, and then incubated for 40-60 minutes at room temperature in darkness.

Lysozyme

Lysozyme was used as a 15 kDa molecular weight marker. 100 μl of 10 mg/ml lysozyme (Calbiochem, San Diego, Calif., USA) solution in water was brought up to a volume of 1 ml with a final concentration of 50 mM Tris pH=8 and 0.5% SDS. 10 μl of 400 mM tributylphosphine (TBP) in isopropanol was added and the protein sample was vortexed for 10-15 seconds and then incubated for 10 minutes at 70° C. The sample is allowed to cool down for 5 minutes at room temperature (or until the temperature drops to 30° C.) and then 5.5 μl of 4-vinylpyridine (distilled) is added and the sample is vortexed to solubilize the 4-vinylpyridine, and then incubated for one hour at room temperature in darkness.

20 kDa BenchMark™ Protein Standard

The 20 kDa BenchMark™ protein standard includes a truncated thioredoxin fragment fused to two copies of a 5 kDa fragment of the E. coli DEAD-box protein (as disclosed in U.S. Pat. No. 6,703,484, herein incorporated by reference in its entirety). 100 μl of 20 kDa BenchMark™ stock solution (OD=8.2) was brought up to a volume of 1 ml with a final concentration of 50 mM Tris pH=8 and 0.5% SDS. 10 μl of 400 mM tributylphosphine (TBP) in isopropanol was added and the protein sample was vortexed for 10-15 seconds and then incubated for 10 minutes at 70° C. The sample was allowed to cool down for 5 minutes at room temperature (or until the temperature dropped to 30° C.) and then 50 μl of 1M iodoacetamide was added and the sample was vortexed for 3-5 seconds, and then incubated for 40-60 minutes at room temperature in darkness.

30 kDa NL Protein Standard

The 30 kDa protein that had no lysines (30 kDa NL) was produced from an expression construct as provided in Examples 1 and 3. Alkylation was performed at 0.5 mg/ml protein concentration. 250 μl of 2 mg/ml 30 kDa (NL) stock solution was brought up to 1 ml volume to a final concentration of 50 mM Tris, 0.5% SDS pH=8. 10 μl 400 mM TBP (tributylphosphine) in isopropanol was added and the protein sample was vortexed for 10-15 seconds. The sample was then incubated for 10 minutes at 70° C. The sample was then cooled for 5 minutes at room temperature (or until the temperature dropped to 30° C.). 50 μl of 1M iodoacetamide was added, and the sample was vortexed for 3-5 seconds and then incubated for 40-60 minutes at room temperature in the dark.

40 kDa NL Protein Standard

The 40 kDa protein that had no lysines (40 kDa NL) was produced from an expression construct as provided in Examples 1 and 3. Alkylation was performed at 0.5 mg/ml protein concentration. 250 μl of 2 mg/ml 30 kDa (NL) stock solution was brought up to 1 ml volume to a final concentration of 50 mM Tris, 0.5% SDS pH=8. 10 μl 400 mM TBP (tributylphosphine) in isopropanol was added and the protein sample was vortexed for 10-15 seconds. The sample was then incubated for 10 minutes at 70° C. The sample was then cooled for 5 minutes at room temperature (or until the temperature dropped to 30° C.). 50 μl of 1M iodoacetamide was added, and the sample was vortexed for 3-5 seconds and then incubated for 40-60 minutes at room temperature in the dark.

50 kDa NL Protein Standard

The 50 kDa protein that had no lysines (50 kDa NL) was produced from an expression construct as provided in Examples 1 and 3. Alkylation was performed at 0.5 mg/ml protein concentration. 250 µl of 2 mg/ml 30 kDa (NL) stock solution was brought up to 1 ml volume to a final concentration of 50 mM Tris, 0.5% SDS pH=8. 10 µl 400 mM TBP (tributhylphosphine) in isopropanol was added and the protein sample was vortexed for 10-15 seconds. The sample was then incubated for 10 minutes at 70° C. The sample was then cooled for 5 minutes at room temperature (or until the temperature dropped to 30° C.). 50 µl of 1M iodoacetamide was added, and the sample was vortexed for 3-5 seconds and then incubated for 40-60 minutes at room temperature in the dark.

60 kDa BenchMark™ Protein Standard

The 60 kDa BenchMark™ molecular weight marker protein includes six fused copies of a truncated *E. coli* thioredoxin protein (see U.S. Pat. No. 6,703,484, herein incorporated by reference in its entirety). 100 µl of 60 kDa BenchMark™ stock solution (OD=3.49) was brought up to a volume of 1 ml with a final concentration of 50 mM Tris pH=8 and 0.5% SDS. 10 µl of 400 mM tributhylphosphine (TBP) in isopropanol was added and the protein sample was vortexed for 10-15 seconds and then incubated for 10 minutes at 70° C. The sample was allowed to cool down for 5 minutes at room temperature (or until the temperature dropped to 30° C.) and then 5.5 µl of 4-vinylpyridine (distilled) was added and the sample was vortexed to solubilize the 4-vinylpyridine and then incubated for one hour at room temperature in the dark.

80 kDa BenchMark™ Protein Standard

The 80 kDa BenchMark™ molecular weight marker protein includes eight fused copies of a truncated *E. coli* thioredoxin protein (see U.S. Pat. No. 6,703,484, herein incorporated by reference in its entirety). 100 µl of 60 kDa BenchMark™ stock solution (OD=6.36) was brought up to a volume of 1 ml with a final concentration of 50 mM Tris pH=8 and 0.5% SDS. 10 µl of 400 mM tributhylphosphine (TBP) in isopropanol was added and the protein sample was vortexed for 10-15 seconds and then incubated for 10 minutes at 70° C. The sample was allowed to cool down for 5 minutes at room temperature (or until the temperature dropped to 30° C.) and then 5.5 µl of 4-vinylpyridine (distilled) was added and the sample was vortexed to solubilize the 4-vinylpyridine and then incubated for one hour at room temperature in the dark.

110 kDa NL Protein Standard

The 110 kDa protein that had no lysines (110 kDa NL) was produced from an expression construct as provided in Example 2 and Example 3. Alkylation was performed at 0.5 mg/ml protein concentration. 50 µl 1M Tris pH=8, 25 µl 20% SDS, and 675 µl water were added to 250 µl of a 2 mg/ml stock solution of the 110 kDa (NL) protein. 10 µl 400 mM TBP (tributhylphosphine) in isopropanol was added and the protein sample was vortexed for 10-15 seconds. The sample was then incubated for 10 minutes at 70° C. The sample was then cooled for 5 minutes at room temperature (or until the temperature dropped to 30° C.). 50 µl of 1M iodoacetamide was added, and the sample was vortexed for 3-5 seconds and then incubated for 40-60 minutes at room temperature in the dark.

160 kDa NL Protein Standard

The 160 kDa protein that had no lysines (160 kDa NL) was produced from an expression construct as provided in Example 2 and Example 3. Alkylation was performed at 0.5 mg/ml protein concentration. 50 µl 1M Tris pH=8, 25 µl 20% SDS, and 675 µl water were added to 250 µl of a 2 mg/ml stock solution of the 160 kDa (NL) protein. 10 µl 400 mM TBP (tributhylphosphine) in isopropanol was added and the protein sample was vortexed for 10-15 seconds. The sample was then incubated for 10 minutes at 70° C. The sample was then cooled for 5 minutes at room temperature (or until the temperature dropped to 30° C.). 50 µl of 1M iodoacetamide was added, and the sample was vortexed for 3-5 seconds and then incubated for 40-60 minutes at room temperature in the dark.

260 kDa Protein Standard

The 260 kDa protein standard (260 kDa) was produced from an expression construct as provided in Example 2 and Example 3. Alkylation was performed at 0.5 mg/ml protein concentration. 50 µl 1M Tris pH=8, 25 µl 20% SDS, and 675 µl water were added to 250 µl of a 2 mg/ml stock solution of the 260 kDa protein. 10 µl 400 mM TBP (tributhylphosphine) in isopropanol was added and the protein sample was vortexed for 10-15 seconds. The sample was then incubated for 10 minutes at 70° C. The sample was then cooled for 5 minutes at room temperature (or until the temperature dropped to 30° C.). 50 µl of 1M iodoacetamide was added, and the sample was vortexed for 3-5 seconds and then incubated for 40-60 minutes at room temperature in the dark.

Purification of the Alkylated Proteins

All alkylated proteins were purified on Bio-Gel P-6 gel filtration columns equilibrated with 0.1% SDS in 50 mM Tris pH=8. The protein elution was monitored at 280 nm with a UV detector. The sample volume was 10% or less of the volume of the column.

EXAMPLE 7

Synthesis of Red Dye #1
(8-anilino-1-naphthalenesulfonic acid-aminophenyl Vinyl sulfone; 8-ANS-APVS)

Figure 12:
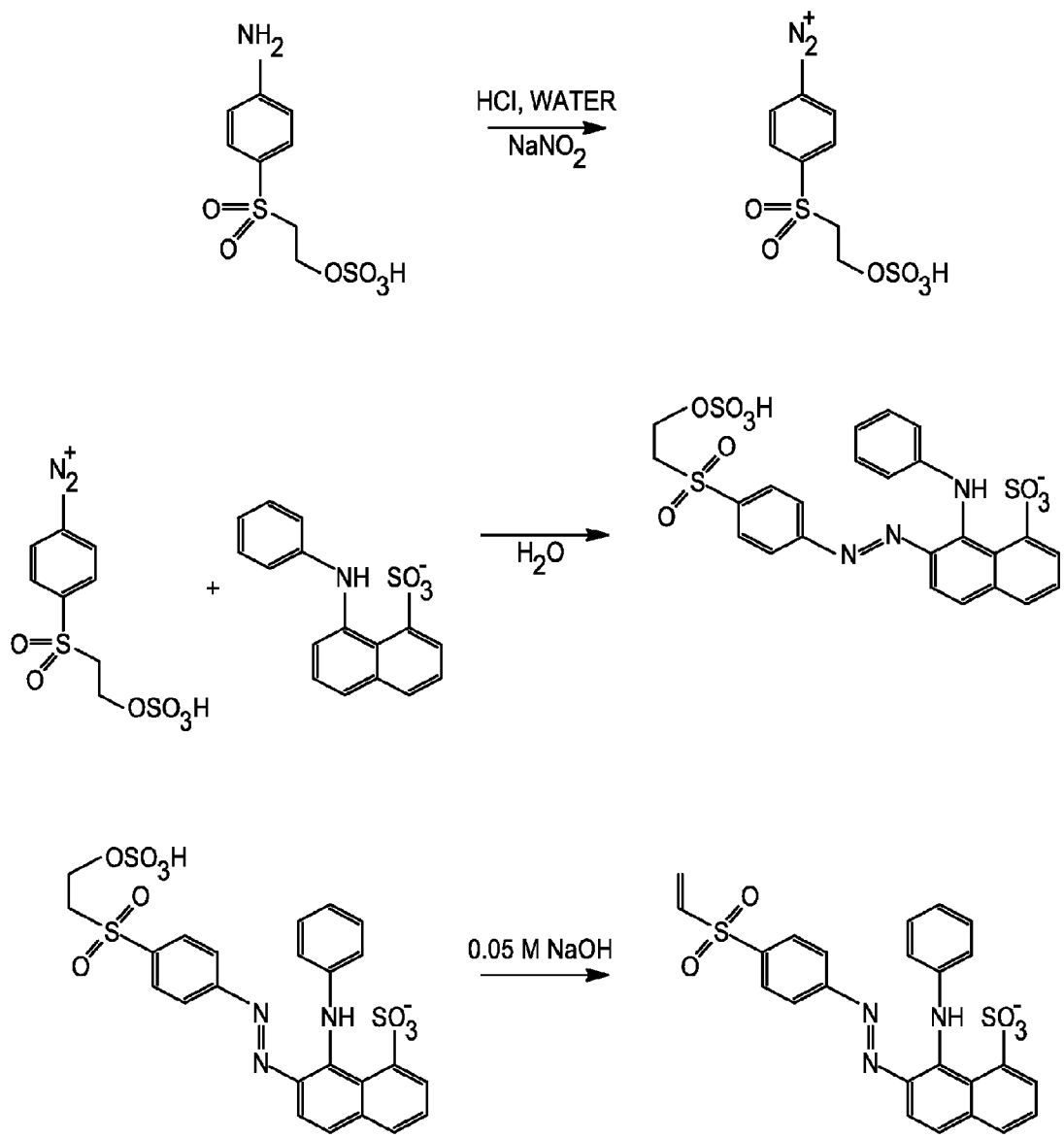
FIG. 12 depicts a scheme for synthesizing 8-anilino-1-naphthalenesulfonic acid-aminophenyl vinyl sulfone (8-ANS-APVS).

The synthesis of 8-anilino-1-naphthalenesulfonic acid-aminophenyl vinyl sulfone (8-ANS-APVS) involves the use of a diazonium salt which is prone to rapid decomposition and can be hazardous. The diazonium salt should not be allowed to dry out. The synthesis scheme is depicted in FIG. 12.

4-aminophenyl-2-sulfonatoethyl sulfone (2.81 grams) was placed in a 200 mL round bottom flask equipped with a stir bar. 50 mL of water was added to the flask, followed by 10 mL of concentrated HCl. The mixture was stirred thoroughly and then cooled to 0° C. in an ice water bath. In a separate 50 mL flask, 0.69 g of sodium nitrite was mixed in 20 mL of water until it was completely dissolved. This mixture was added to an addition funnel and placed on top of the flask containing the 4-aminophenyl-2-sulfonatoethyl sulfone. The sodium nitrite solution was added dropwise to the mixture and the solid in the flask began to dissolve with a yellowish/green color developing in the solution. After the addition of sodium nitrite was complete the ice bath was removed and the temperature was allowed to rise to ~20° C. The solution became clear as the diazonium salt formed. The solution was then cooled back to 0° C. to precipitate the diazonium salt.

8-anilino-1-naphthalenesulfonic acid (8-ANS) was prepared by placing the solid in a 250 mL round bottom flask equipped with a stir bar. 30 mL of water was added, followed by 5 mL of 1.0 M sodium carbonate. The mixture was stirred thoroughly until the 8-ANS dissolved. The diazonium salt was transferred to an addition funnel and the diazonium salt solution was added to the solution of 8-ANS dropwise with stirring. A dark color developed immediately. Once the addition was finished the mixture was stirred for at least 2 hours up to overnight.

The dye was purified by reverse phase chromatography using either methanol or acetonitrile as the eluant. The dye was loaded on the C-18 resin in 50 mM phosphate pH 3.0 (the pH of the aqueous dye solution was increased before loading onto the column to avoid breaking the silane bonds of silica-based C-18 sorbents). The resin-bound dye was then washed to remove most of the acid from the coupling step. At low pH the dye is a purple color and the fractions collected were in some cases checked by HPLC to assess purity. The combined fractions were reduced in vacuo by rotary evaporation at reduced pressure. The yield was calculated by standard methods. The dried dye vinyl sulfone precursor was dissolved in 50 mL of water and transferred to a 100-200 mL round bottom flask equipped with a stir bar. While stirring the solution 5 mL of the 1.0 M sodium carbonate solution was added. The pH was maintained at 10.0±0.2 using a calibrated pH meter. This solution was stirred for 1 hour and then adjusted to pH 7 using 1 N HCl. The dye was purified using a reverse phase column. The reactive dye was loaded directly onto the column after adjusting the pH to 7. The column was washed thoroughly with water after the dye was loaded. The dye was eluted in acetonitrile and the colored fractions were collected. The dye fractions were combined and the solvent was removed in vacuo using a rotary evaporator. The solid dye was weighted and the yield was calculated. A negative ion mode mass spectrum was obtained to be sure that a parent peak was seen at a mass to charge ratio of 492.

EXAMPLE 8

Activation of Orange 16 Dye

The starting material, Reactive Orange 16 (also called Remazol Brilliant Orange 3R), was obtained from Sigma-Aldrich Chemical Company. It was converted to the vinyl sulfone in order to react with the sulfhydryls of proteins for generating dyed marker proteins. The reaction scheme for generating the vinyl sulfone form of the dye is depicted in FIG. 13.

A 100 mL round bottom flask was equipped with the appropriate sized egg-shaped stir bar. The flask was charged with Reactive Orange 16 which was dissolved by the required volume of water. With the solution is stirring, sodium hydroxide was added dropwise to the stirred the solution until the pH is 10.0±0.1. The reaction was allowed to stir for 2 hours and while the pH was monitored. 100 µl of 1M sodium carbonate was added to keep the pH at 10.0. After two hours the pH was adjusted back to neutrality using 1 M HCl.

The was purified by C18 column chromatography. The product was loaded onto a Waters bondapak resin column in 50 mM phosphate pH 4. Once the product was loaded onto the column the column was washed with 3 column volumes of water and then the product was eluted using 50% HPLC grade methanol in water. The fractions were combined and the dark fractions were concentrated in vacuo on a rotary evaporator. The product was scraped from the flask and placed in a tared amber bottle/vial to obtain the weight of product. The bottle was purged with argon and labeled with the following name to distinguish it from the starting material: "Reactive Orange 16 Vinyl Sulfone".

EXAMPLE 9

Labeling of Standard Proteins with Dyes

The labeling of all no-lysine (NL) proteins (the 30 kDa, 40 kDa, 50 kDa, 110 kDa, and 160 kDa NL proteins) and the 260 kDa protein was performed at 0.5 mg/ml final concentration. The amount of protein and water added to the reactions was adjusted depending on the starting protein concentration. Insulin and lysozyme were labeled at the concentrations described in the corresponding protocols. BenchMark™ protein standards are described in U.S. Pat. No. 6,704,484, herein incorporated by reference in its entirety.) The BenchMark™ protein standard stock solutions were labeled at constant concentration (the ODs specified in the protocols).

Insulin

50 µl 1M Tris pH=8, 25 ul 20% SDS, and 875 µl ultrapure water were added to 50 µl of 20 mg/ml Insulin b-chain protein. 2.5 µl 400 mM TBP was added and the protein sample was incubated for 20 minutes at 70° C. The sample was then cooled for 5 minutes at room temperature or until the temperature was below 50° C. 100 µl 10 mg/ml Uniblue A in water was then added to the peptide sample and the sample was incubated for 3 hours at 50° C.

10 kDa BenchMark™ Standard

The BenchMark™ 10 kDa protein standard (Invitrogen Corp., Carlsbad, Calif.; U.S. Pat. No. 6,703,484) was labeled for use as the 10 kDa standard of the pre-labeled marker set. 50 µl 1M Tris pH=8, 25 ul 20% SDS, and 825 µl ultrapure water were added to 100 µl of an 8.3 OD solution of 10 kDa BenchMark™ protein standard stock solution. 2.5 µl 400 mM TBP was added and the protein sample was incubated for 20 minutes at 70° C. The sample was then cooled for 5 minutes at room temperature or until the temperature was below 30° C. 50 µl 10 mg/ml 8-ANS-APVS in DMF was added to the protein sample and the sample was incubated for 3 hours at room temperature.

Lysozyme

50 µl 1M Tris pH=8, 25 ul 20% SDS, and 825 µl ultrapure water were added to 100 µl 10 mg/ml lysozyme solution in water. 2.5 µl 400 mM TBP was added and the protein sample was incubated for 20 minutes at 70° C. The sample was then cooled for 5 minutes at room temperature or until the temperature was below 30° C. 50 µl of 10 mg/ml Uniblue in DMF was added to the protein sample and the sample was incubated overnight at room temperature.

20 kDa BenchMark™ Protein Standard

The BenchMark™ 20 kDa protein standard, a 19.891 kDa protein having a truncated thioredoxin linked to two copies of a 5 kDa fragment of the Dead-box protein, (Invitrogen Corp., Carlsbad, Calif.; U.S. Pat. No. 6,703,484) was labeled for use as the 20 kDa standard of the pre-labeled marker set. 50 µl 1M Tris pH=8, 25 ul 20% SDS, and 825 µl ultrapure water were added to 100 µl of an 8.2 OD solution of 20 kDa BenchMark™ protein standard stock solution. 2.5 µl 400 mM TBP was added and the protein sample was incubated for 20 minutes at 70° C. The sample was then cooled for 5 minutes at room temperature or until the temperature was below 30° C. 12.5 µl of 20 mg/ml Bodipy 530/550 iodoacetamide in DMF was added to the protein sample and the sample was incubated for 3 hours at room temperature.

30 kDa NL Protein Standard

50 µl 1M Tris pH=8, 25 ul 20% SDS, and 800 µl ultrapure water were added to 125 µl of a 5 mg/ml solution of the 30 kDa NL standard protein. 2.5 µl 400 mM TBP was added and the protein sample was incubated for 20 minutes at 70° C. The sample was then cooled for 5 minutes at room temperature or until the temperature was below 30° C. 100 µl of 10 mg/ml Uniblue A in water was added to the protein sample and the sample was incubated overnight (14-18 hours) at room temperature.

40 kDa NL Protein Standard

50 µl 1M Tris pH=8, 25 ul 20% SDS, and 725 µl ultrapure water were added to 200 µl of a 2.5 mg/ml solution of the 40 kDa (NL) standard protein. 2.5 µl 400 mM TBP was added and the protein sample was incubated for 20 minutes at 70° C. The sample was then cooled for 5 minutes at room temperature or until the temperature was below 30° C. 50 µl of 40 mg/ml activated Orange 16 in water was added to the protein sample and the sample was incubated for 3 hours at room temperature.

50 kDa NL Protein Standard

M Tris pH=8, 25 ul 20% SDS, and 800 µl ultrapure water were added to 125 µl of a 5 mg/ml solution of the 50 kDa (NL) standard protein. 2.5 µl 400 mM TBP was added and the protein sample was incubated for 20 minutes at 70° C. The sample was then cooled for 5 minutes at room temperature or until the temperature was below 30° C. 100 µl of 10 mg/ml Uniblue A in water was added to the protein sample and the sample was incubated overnight (14-18 hours) at room temperature.

60 kDa BenchMark™ Protein Standard

The BenchMark™ 60 kDa protein standard (Invitrogen Corp., Carlsbad, Calif.; U.S. Pat. No. 6,703,484) was labeled for use as the 60 kDa standard of the pre-labeled marker set. 50 µl 1M Tris pH=8, 25 ul 20% SDS, and 665 µl ultrapure water were added to 260 µl of a 3.49 OD solution of 60 kDa BenchMark™ standard protein stock solution. 2.5 µl 400 mM TBP was added and the protein sample was incubated for 20 minutes at 70° C. The sample was then cooled for 5 minutes at room temperature or until the temperature was below 30° C. 50 µl of 10 mg/ml 8-ANS-APVS in DMF was added to the protein sample and the sample was incubated for 6 hours at room temperature.

80 kDa BenchMark™ Protein Standard

The BenchMark™ 80 kDa protein standard (Invitrogen Corp., Carlsbad, Calif.; U.S. Pat. No. 6,703,484) was labeled for use as the 80 kDa standard of the pre-labeled marker set. 50 µl 1M Tris pH=8, 25 ul 20% SDS, and 825 µl ultrapure water were added to 100 µl of a 6.36 OD solution of 80 kDa BenchMark™ protein standard stock solution. 2.5 µl 400 mM TBP was added and the protein sample was incubated for 20 minutes at 70° C. The sample was then cooled for 5 minutes at room temperature or until the temperature was below 30° C. 12.5 of 20 mg/ml Bodipy 530/550 iodoacetamide in DMF was added to the protein sample and the sample was incubated for 2.5 hours at room temperature.

110 kDa NL Protein Standard

50 µl 1M Tris pH=8, 25 ul 20% SDS, and 800 µl ultrapure water were added to 125 µl of a 4 mg/ml solution of the 110 kDa (NL) standard protein. 2.5 µl 400 mM TBP was added and the protein sample was incubated for 20 minutes at 70° C. The sample was then cooled for 5 minutes at room temperature or until the temperature was below 30° C. 100 µl of 10 mg/ml Uniblue A in water was added to the protein sample and the sample was incubated overnight (14-18 hours) at room temperature.

160 kDa NL Protein Standard

50 µl 1M Tris pH=8, 25 ul 20% SDS, and 800 µl ultrapure water were added to 125 µl of a 4 mg/ml solution of the 160 kDa (NL) standard protein. 2.5 µl 400 mM TBP was added and the protein sample was incubated for 20 minutes at 70° C. The sample was then cooled for 5 minutes at room temperature or until the temperature was below 30° C. 100 µl of 20 mg/ml Orange 16 in DMF was added to the protein sample and the sample was incubated for 3 hours at 50° C.

260 kDa Protein Standard

50 µl 1M Tris pH=8, 25 ul 20% SDS, and 725 µl ultrapure water were added to 200 µl of a 2.5 mg/ml solution of the 260 kDa standard protein. 2.5 µl 400 mM TBP was added and the protein sample was incubated for 20 minutes at 70° C. The sample was then cooled for 5 minutes at room temperature or until the temperature was below 30° C. 25 of 20 mg/ml Bodipy 530/550 Iodoacetamide in DMF was added to the protein sample and the sample was incubated for 5-6 hours at room temperature.

Purification of Labeled Proteins

All of the standard proteins except lysozyme were purified on gel filtration LC column packed with Toyopearl HW-40c resin. The volume of the column was at least 15 times the volume of the sample for the proteins labeled with Uniblue A, Orange 16 and Bodipy 530/550 dyes. The volume of the column was at least 20 times the volume of the sample for proteins labeled with the Red (8-ANS-APVS) dye.

For purification of lysozyme labeled with Uniblue-A, Bio-Gel P-6 column equilibrated with 8M urea was used. The column had a volume of at least 20 times the sample volume. The sample was loaded on the column and the dye was separated from the protein conjugate. Two dye peaks were seen. After the sample is collected the urea was exchanged to Tris/SDS by loading the sample onto a Bio-Gel P-6 column equilibrated with 50 mM Tris, 0.5% SDS. (The column volume was at least ten times the sample volume.)

Capping of Labeled Proteins

A capping step was performed to neutralize any unreacted cysteine residues on the standard proteins to prevent the proteins from forming intra and inter disulfide bridges which could lead to changes in electrophoretic migration and reduce band sharpness on gels. Labeled proteins were denatured and reduced with the addition of 25 µl of 20% SDS and 10 µl 400 mM TBP per 1 ml of protein conjugate with an incubation of 30 minutes at room temperature. Then 50 µl of 1M iodoacetamide was added per 1 ml of protein conjugate and the sample was incubated for 1 hour at room temperature. In the case of lysozyme SDS was not added prior to the reaction since the SDS concentration of the lysozyme standard solution was already at 0.5%. 10 µl 400 mM TBP were added per 1 ml of protein conjugate and sample incubated for 30 minutes at room temperature. Then 50 µl of 1M iodoacetamide was added per 1 ml of protein conjugate and the sample was incubated for 1 hour at room temperature.

The unreacted reducing and alkylation reagents were removed from the labeled, alkylated proteins by gel filtration on Bio-Gel P-6 columns equilibrated with 0.1% SDS in 50 mM Tris pH=8.

Sephacryl Purification of the Labeled Proteins

In some cases a second purification of a standard protein was performed on Sephacryl column. Sephacryl 200-HR was used for proteins of 10 kDa to 30 kDa and Sephacryl 400-HR was used for proteins with molecular weight of 40 kDa to 260 kDa. The columns were washed with 50 mM Tris, 0.1% SDS and then the sample was loaded.

The column had a volume of at least 30 times the sample volume and length to internal diameter ratio of at least 20 (for example 100 cm×5 cm ID column can be used for the purification 100 ml sample. Fractions of 10 ml were collected and aliquots were run on a gel, and the purified protein fractions were pooled together.

Concentration

Standard proteins were concentrated on Vivaspin MWCO filters with suitable pore size: 100 kDa MWCO filter for 260 kDa, 160 kDa and 110 kDa standard proteins; 50 kDa MWCO filter for 80 kDa, 60 kDa and 50 kDa standard proteins; 30 kDa MWCO filter for 40 kDa and 30 kDa standard proteins; 10 kDa MWCO filter for 20 kDa, lysozyme, and 10 kDa standard proteins; 3 kDa MWCO filter for insulin b-chain.

EXAMPLE 10

Electrophoretic Migration

Each of the prestained proteins was loaded side by side with the corresponding unlabeled protein marker on gels. The samples were analyzed for migration on 8 cm×8 cm 4-12% BisTris/MES gels, 4-12% BisTris/MOPS gels, and 4-20% Tris Glycine gels. The gels were run at 200 V until the dye front reached the bottom of the gel (6.8 cm from the bottom of the sample wells). After electrophoresis the gel was stained with SimplyBlue™ Safe Stain Coomassie G-250® protein stain (Invitrogen Corp., Carlsbad, Calif.) according to the microwave protocol. The gels were destained for several hours to overnight with deionized water. The migration of the labeled proteins was measured on Alpha Imager 3000 imaging system. Pictures of the gels were taken with the Alpha Imager and the migration of the labeled proteins were analyzed relative to the same protein standard in unlabeled form. Point-to-point calibration was used to increase the accuracy of the measurement in calculating the molecular weights of the proteins based on their migration distances, in which a standard curve was generated by plotting the log of molecular weight versus migration distance for the two protein markers migrating closest to the protein whose molecular weight was being calculated (one that migrated a shorter distance than the protein standard whose weight was being calculated and the other that migrated a longer distance than the protein standard whose weight was being calculated.) The pre-labeled protein standards were observed to migrate substantially the same as their unlabeled counterparts when the molecular weights were calculated from the point-to-point calibration were within 10%. All of the labeled molecular weight marker proteins having molecular weights of 10 kDa or greater migrated within 4.5% of the migration of their unlabeled counterparts.

EXAMPLE 11

Sharp Pre-stained Standard Protein Blend Preparation

Twelve labeled proteins (insulin b-chain, 10 kDa BenchMark™ protein Standard, 20 kDa BenchMark™ protein Standard, 30 kDa NL protein Standard, 40 kDa NL protein Standard, 50 kDa NL protein Standard, 60 kDa BenchMark™ protein Standard, 80 kDa BenchMark™ protein Standard, 110 kDa NL protein Standard, 160 kDa NL protein Standard, and 260 kDa protein Standard) were blended to make a molecular weight standard set in which the molecular weights of the protein standards ranged from less than 3.5 kDa to greater than 250 kDa. The molecular weight standard set included proteins labeled with four different visually distinguishable dyes. The proteins were blended for consistent batch-to-batch intensity by comparing the intensity of the bands from each new preparation of labeled standard to a prior batch of standard to provide standards with no more than 20% variation in the band intensities from batch to batch. An appropriate amount of each protein standard was added to the blend and ultra pure water was added to 50% of the target final volume. Then 50% of the target final volume of 2× Sample Buffer (130 mM Tris pH=6.5, 4% SDS, 60% Glycerol, 0.01% Coomassie G 250) was added to the marker blend preparation.

An unlabeled standard set comprising the same proteins as the pre-labeled set was also formulated. The unlabeled standard set was formulated such that the 20 kDa and 80 kDa standard protein bands were more intense than the other protein bands when viewed on an electrophoresis gel, so that the user can orient the proteins readily by observation of the intense 20 kDa and 80 kD bands.

TABLE 4

Sharp Pre-stained Standard Proteins

| Protein Standard | Conjugated Dye | Visible Color | Molecular Weight to nearest 1 kDa | Actual Molecular Weight (kDa) |
|---|---|---|---|---|
| Insulin B-chain 3.5 kDa protein Standard | Uniblue A | Blue | 3 | 3.4 (seq) |
| BenchMark™ 10 kDa protein Standard | ANS-APVS (Red dye #1) | Red | 10 | 10.170 10.172 (ms) |
| Lysozyme 15 kDa protein Standard | Uniblue A | Blue | 14 | |
| BenchMark™ 20 kDa protein Standard | Bodipy 530/550 | Pink | 20 | 19.892 (seq) 19.906 (ms) |
| No-lysine 30 kDa protein Standard | Uniblue A | Blue | 30 | 30.012 29.979 (ms) |
| No-lysine 40 kDa protein Standard | Orange 16 | Orange | 40 | 40.123 (ms) |
| No-lysine 50 kDa protein Standard | Uniblue A | Blue | 50 | 50.253 (seq) 50.044 (ms) |
| BenchMark™ 60 kDa protein Standard | ANS-APVS (Red dye #1) | Red | 60 | 59.738 (ms) |
| BenchMark™ 80 kDa protein Standard | Bodipy 530/550 | Pink | 80 | 79.785 (ms) |
| No-lysine 110 kDa protein Standard | Uniblue A | Blue | 110 | 109.798 (ms) |
| No-lysine 160 kDa protein Standard | Orange 16 | Orange | 159 | 158.843 (ms) |
| 260 kDa protein Standard | Bodipy 530/550 | Pink | 262 | 262.379 (ms) |

EXAMPLE 12

Electophoresis of a Pre-labeled Protein Standard Set

Figures 14A, 14B:
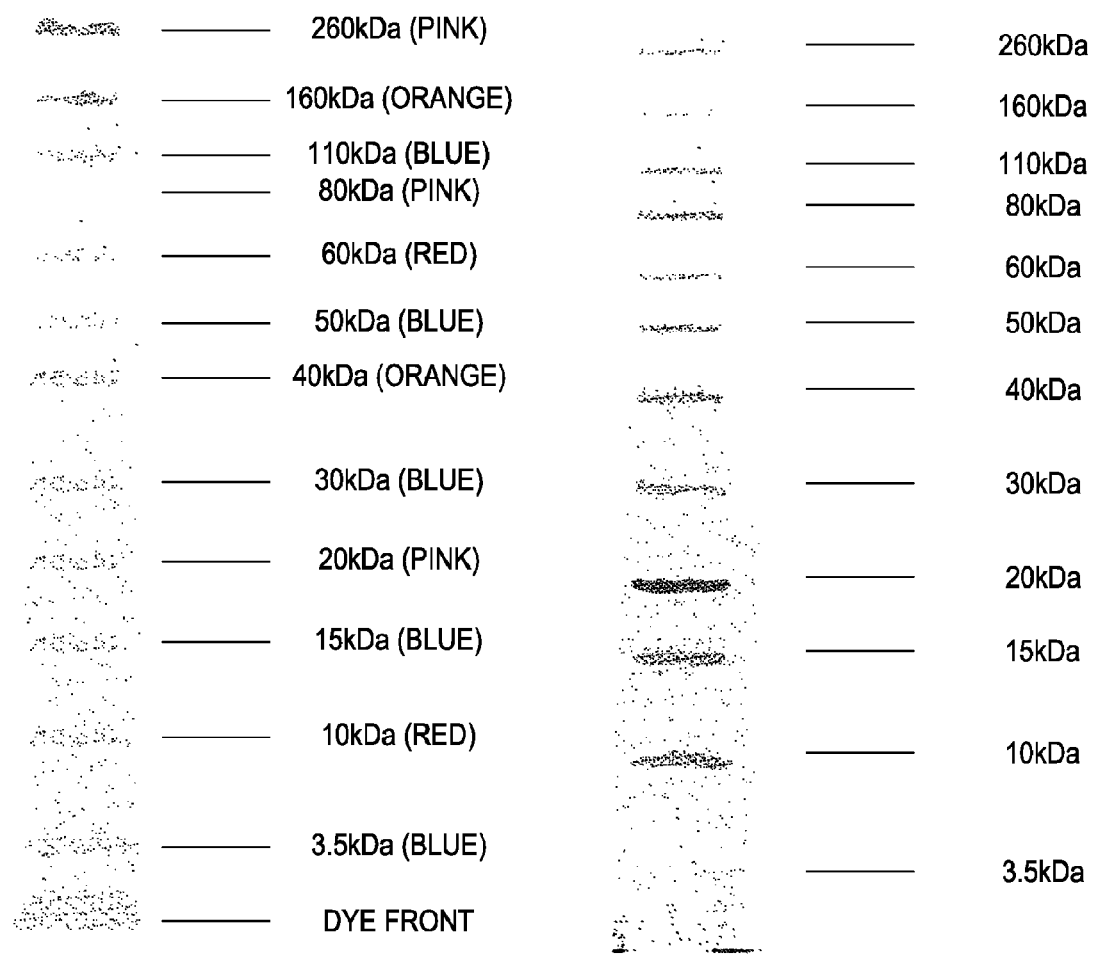
FIG. 14 A) shows a pre-labeled protein standard set of the invention electrophoresed on a 4-12% Bis-Tris gel with 1×MES running buffer. B) shows the same set of markers in unlabeled form electrophoresed on a 4-12% Bis-Tris gel with MES running buffer.
Figure 15A:
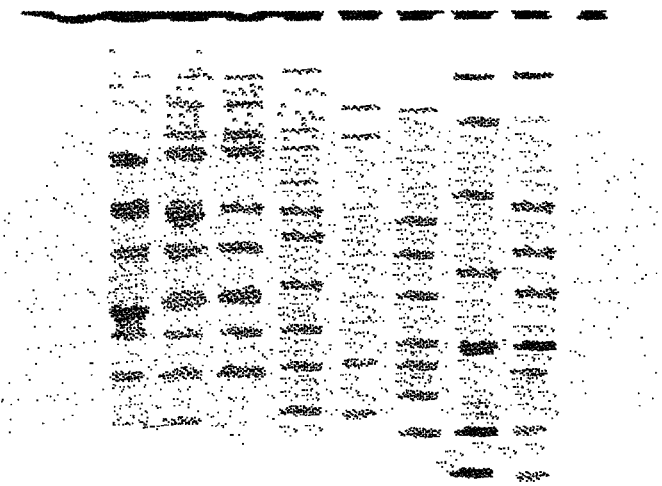
FIG. 15 A) shows a 4-12% Bis-Tris gel with 1×MES running buffer, B) shows a 4-12% Bis-Tris gel with 1×MOPS running buffer, and C) shows a 4-20% Tris-glycine gel on which a set of pre-labeled protein standards (Sharp Pre-stained Standard; lane 4) were electrophoresed alongside other commercially available pre-stained markers: 1—Precision Plus Blue (Bio-Rad); 2—Precision Plus Dual (Bio-Rad); 3—Precision Plus Kaleidoscope (Bio-Rad); 4—Sharp Pre-stained Standard (Invitrogen); 5—Rainbow (GE); 6—BenchMark™ prestain (Invitrogen); 7—Multi-Mark (Invitrogen); 8—SeeBlue+2 (Invitrogen).
Figure 15B:
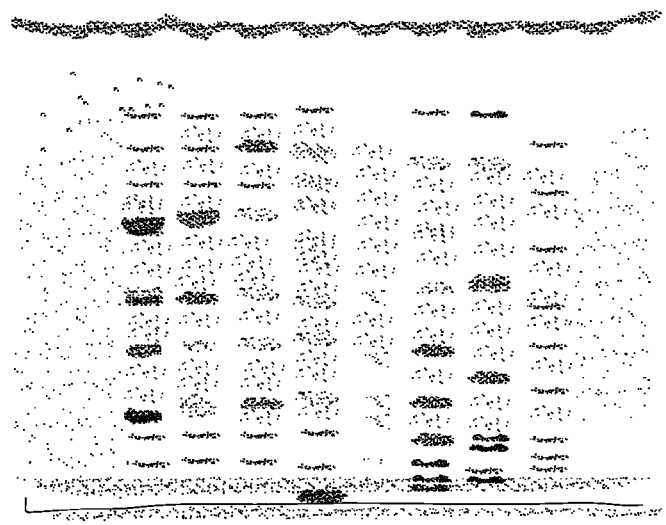
Figure 15C:
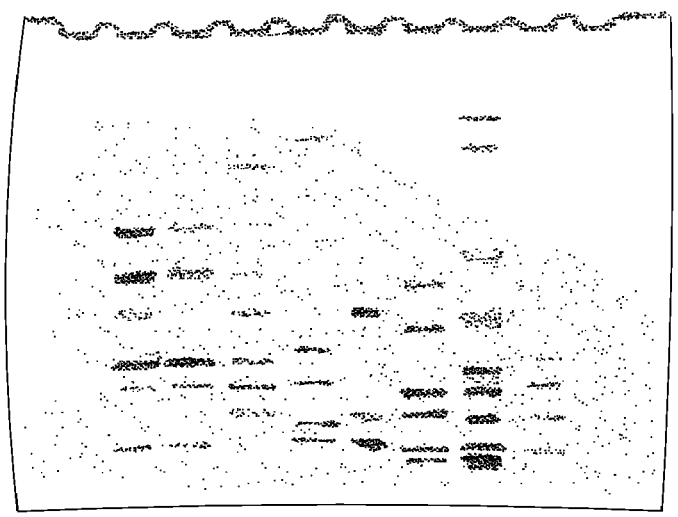

The pre-labeled marker set of Example 11 (10 microliters) was electrophoresed alongside the same set of proteins in unlabeled form (5 microliters) in a 4-12% Bis-Tris (NuPAGE® Novex®) acrylamide gel run with 1×MES buffer. FIG. 14 shows that the pre-labeled protein standard set that includes five proteins labeled on cysteine and lacking lysine has twelve bands that produce sharp bands that migrate substantially the same as their unlabeled counterparts. The pre-labeled marker set of Example 11 was also electrophoresed on a 4-12% Bis-Tris (NuPAGE® Novex®) acrylamide gel run with 1×MES buffer, a 4-12% Bis-Tris (NuPAGE® Novex®) acrylamide gel run with 1×MOPS buffer, and a 4-20% Tris-glycine (Novex®) gel (FIG. 15) alongside other commercially available markers (1, Precision Plus Blue (Bio-Rad); 2, Precision Plus Dual (Bio-Rad); 3, Precision Plus Kaleidoscope (Bio-Rad); 4, Sharp Pre-stained Standard (Invitrogen); 5—Rainbow (GE); 6—Bench-Mark™ prestain (Invitrogen); 7—MultiMark (Invitrogen); 8—SeeBlue+2 (Invitrogen). All gels were 8×8 cm "mini" gels from Invitrogen, Carlsbad, Calif., and electrophoresis conditions were those provided by the manufacturer.

TABLE 5

Migration of Pre-labeled Standard Set on BisTris Gels

| Band | 4-12% Gel/MES | 4-12% Gel/MOPS |
|---|---|---|
| 260 kDa | 0% | −2.1% |
| 160 kDa | −4.1% | −4.5% |
| 110 kDa | −3.7% | −2.7% |
| 80 kDa | +1.5% | +3.7% |
| 60 kDa | −0.4% | +0.6% |
| 50 kDa | −3.4% | −3.3% |
| 40 kDa | +1% | +0.3% |
| 30 kDa | −0.5% | −1.6% |
| 20 kDa | +2.2% | +0.5% |
| 15 kDa | 0% | −3.5% |
| 10 kDa | +1.2% | −0.1%* |
| 3.5 kDa | +10%** | |

TABLE 6

Migration of Pre-labeled Standard Set on 4-20% Tris glycine gel

| Bands | Percent difference |
|---|---|
| 260 kDa | 0% |
| 160 kDa | −1.2% |
| 110 kDa | −1.8% |
| 80 kDa | +4.3% |
| 60 kDa | −1% |
| 50 kDa | +0.3% |
| 40 kDa | +3.6 |
| 30 kDa | −0.6% |
| 20 kDa | 0% |
| 15 kDa | +1.3% |
| 10 kDa | 0% |

EXAMPLE 13

Figure 16A:
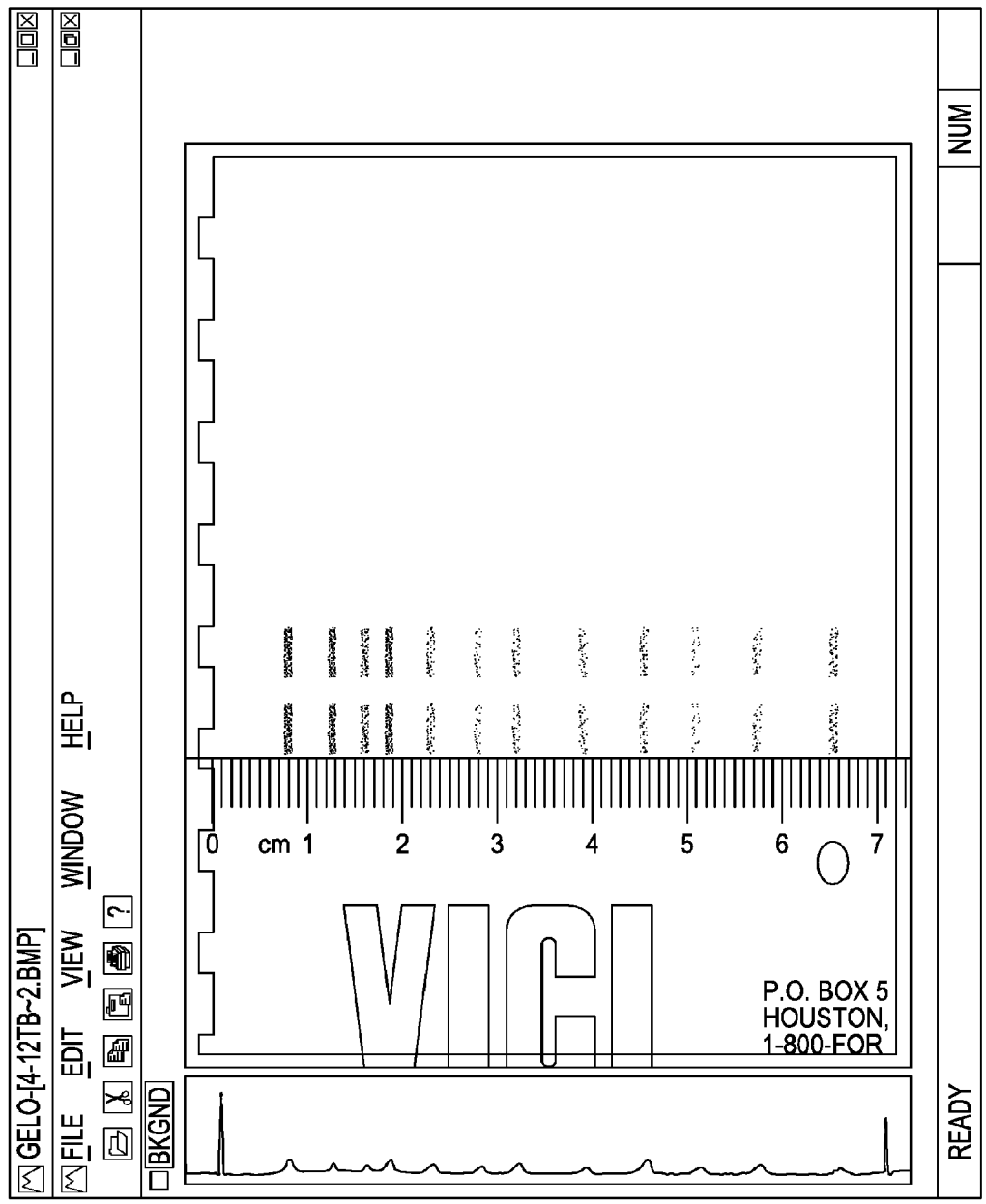
FIG. 16 A) depicts a ruler aligned with a gel on which pre-labeled protein standards of the invention were electrophoresed for determining band width of the pre-labeled standards. B) depicts a trace extracted from the gel image having peaks 2-13 corresponding to band intensity of the pre-labeled proteins.

Calculation of Band Widths of Electophoresed Proteins of a Pre-labeled Protein Standard Set 10 ul Sharp Pre-stained Protein Standard formulation of Example 11 was run on a 4-12% acrylamide gradient Bis-Tris NuPAGE® gel run with 1×MES running buffer (Invitrogen, Carlsbad, Calif.). After electrophoresis the gel was placed on a transparency having a copy of a measuring scale (FIG. 16A). The gel was then scanned at 300/300 dpi and saved as gray scale '.BMP' image.

The resolution of the gel was later decreased across the width (to make it compatible with Gelo.exe). The resulting gel image was loaded in Gelo.exe, a software program designed to measure dimensions of an image, and a trace was extracted of image intensity down the length of the gel.

Figure 16B:
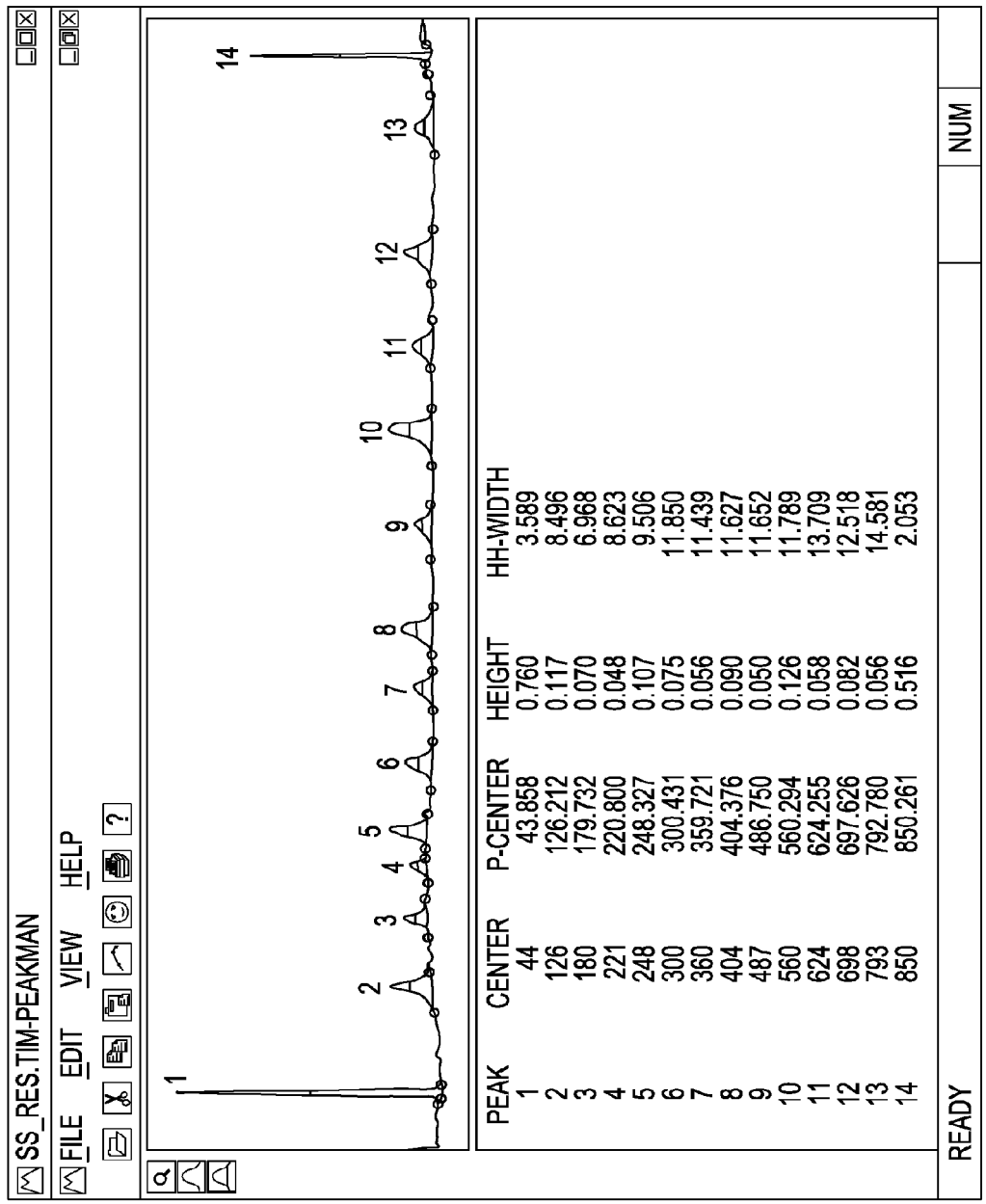

The extracted trace was loaded in Peakman.exe. The baseline was adjusted and peaks were selected. The Peakman.exe program measured the width of the bands where the intensity of the image was 50% or more of the maximum intensity peak height for (FIG. 16B). The data was loaded in Excel and the number of image units per 1 mm was calculated by dividing the length of the gel by the total number of image units for this length: Running length of the gel=68 mm; Length in image units=850−44=806; Number of image units per 1 mm=806/68=11.85. The width of each peak at half height was therefore divided by 11.85 to obtain the width in millimeters.

The widths of the bands produced by the electrophoreses protein standard (peaks 2-13, corresponding to pre-stained protein bands on the gel), are provided in Table 7. The width of bands visible to the naked eye from proteins having a molecular weight of greater than 3.5 kDa range in width from 0.59 mm to 1.16 mm, a difference of just under 2-fold. The width of bands visible to the naked eye from proteins having a molecular weight of at least 10 kDa to 110 kDa or less range in width from 0.73 mm to 1.16 mm, a difference of less than 1.5-fold. The width of bands visible to the naked eye from proteins having a molecular weight of at least 20 kDa to less than 100 kDa range in width from 0.99 mm to 1.16 mm, a difference of less than 20%. The markers include 6 proteins having a molecular weight of at least 20 kDa to less than 100 kDa, in which the width of the bands visible to the naked eye of the electrophoresed proteins differ by less than 20%.

TABLE 7

Band Widths of Sharp Pre-stained Standard Proteins

| Band | Peak Height | Half height-Width | Half-height Width (mm) |
|---|---|---|---|
| 260 kDa | 0.117 | 8.496 | 0.72 |
| 160 kDa | 0.070 | 6.968 | 0.59 |
| 110 kDa | 0.048 | 8.623 | 0.73 |
| 80 kDa | 0.107 | 9.506 | 0.80 |
| 60 kDa | 0.075 | 11.85 | 1.00 |
| 50 kDa | 0.056 | 11.439 | 0.97 |
| 40 kDa | 0.090 | 11.627 | 0.98 |
| 30 kDa | 0.050 | 11.652 | 0.98 |
| 20 kDa | 0.126 | 11.789 | 0.99 |
| 15 kDa | 0.058 | 13.709 | 1.16 |
| 10 kDa | 0.082 | 12.518 | 1.06 |
| 3.5 kDa | 0.056 | 14.581 | 1.23 |

The intensity of the bands, as seen by the Peak Height column, varies by no more than 2.5-fold among the proteins of the set.

Although various embodiments of the invention have been described and provided in the above examples, it will be understood that modifications and variations are encompassed within the spirit and scope of the invention. In particular, elements and features of embodiments described herein can be combined with elements and features of other embodiments described herein or known in the art to produce further embodiments within the scope of the invention. Headings have been provided solely for the convenience of the reader, and do not limit the scope of the invention.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A pre-labeled protein standard set comprising a plurality of labeled proteins, each protein having a known and different molecular weight ranging from 10 Da to 260 kDa, wherein one or more of said plurality of labeled proteins is a selectively labeled protein comprising a heterologous chromophore or a heterologous fluorophore label conjugated to a first amino acid, wherein said selectively labeled protein has fewer than one lysine residue per ten kilodalton (kDa) molecular weight of said selectively labeled protein, wherein at least a first selectively labeled protein comprises an amino acid sequence that has at least 80% sequence identity with the amino acid sequence of SEQ ID NO: 14.

2. The pre-labeled protein standard set of claim 1, wherein said selectively labeled protein lacks lysine residues.

3. The pre-labeled protein standard set of claim 1, wherein said selectively labeled protein comprises the heterologous chromophore.

4. The pre-labeled protein standard set of claim 1, further comprising one or more proteins comprising the amino acid sequence selected from the group consisting of: SEQ ID NO: 1, 2, 3, 4, 5, 6, 7, 8, 11, 12, 13, 15, 16, 17, 37, 38, 39, 40, and 41.

* * * * *